US009550010B2

(12) United States Patent
Schulz et al.

(10) Patent No.: US 9,550,010 B2
(45) Date of Patent: Jan. 24, 2017

(54) METHODS OF TREATING DEGENERATIVE BONE CONDITIONS

(75) Inventors: Olaf Schulz, Lakeland, TN (US); James Howe, Shelburne, VT (US); Rick Swaim, Lakeland, TN (US); Bryan Huber, Stowe, VT (US); Joel Batts, Lakeland, TN (US); David Harness, Eads, TN (US); Ryan Belaney, Oakland, TN (US)

(73) Assignee: Agnovos Healthcare, LLC, Rockville, MD (US)

( * ) Notice: Subject to any disclaimer, the term of this patent is extended or adjusted under 35 U.S.C. 154(b) by 0 days.

(21) Appl. No.: 13/173,701

(22) Filed: Jun. 30, 2011

(65) Prior Publication Data

US 2012/0004594 A1 Jan. 5, 2012

Related U.S. Application Data

(60) Provisional application No. 61/361,177, filed on Jul. 2, 2010.

(30) Foreign Application Priority Data

Jun. 29, 2011 (TW) ............................. 100122879 A

(51) Int. Cl.
*A61L 24/00* (2006.01)
*A61L 27/12* (2006.01)
*A61L 27/58* (2006.01)
*A61L 24/02* (2006.01)
*A61B 17/17* (2006.01)
*A61B 17/16* (2006.01)

(52) U.S. Cl.
CPC ............ *A61L 24/0042* (2013.01); *A61L 24/02* (2013.01); *A61L 27/12* (2013.01); *A61L 27/58* (2013.01); *A61B 17/16* (2013.01); *A61B 17/1668* (2013.01); *A61B 17/17* (2013.01); *A61L 2400/06* (2013.01); *A61L 2430/02* (2013.01)

(58) Field of Classification Search
CPC . A61B 17/16; A61B 17/1668; A61L 2400/06; A61L 2430/02; A61L 24/0042; A61L 24/02; A61L 27/12; A61L 27/58
See application file for complete search history.

(56) References Cited

U.S. PATENT DOCUMENTS

| | | |
|---|---|---|
| 2,730,101 A | 1/1956 | Hoffman |
| 2,816,552 A | 12/1957 | Hoffman |
| 3,030,951 A | 4/1962 | Mandarin |
| 3,181,533 A | 5/1965 | Heath |
| 3,320,957 A | 5/1967 | Sokolik |
| 3,557,794 A | 1/1971 | Van Patten |
| 3,670,732 A | 6/1972 | Robinson |
| 3,702,611 A | 11/1972 | Fishbein |
| 3,875,595 A | 4/1975 | Froning |
| 3,938,530 A | 2/1976 | Santomieri |
| 4,440,750 A | 4/1984 | Glowacki et al. |
| 4,596,243 A | 6/1986 | Bray |
| 4,611,594 A | 9/1986 | Grayhack et al. |
| 4,743,229 A | 5/1988 | Chu |
| 4,751,922 A | 6/1988 | DiPetropolo |
| 4,755,184 A | 7/1988 | Silverberg |
| 4,880,610 A | 11/1989 | Constantz |
| RE33,258 E | 7/1990 | Onik et al. |
| 4,961,740 A | 10/1990 | Ray et al. |
| 4,969,888 A | 11/1990 | Scholten et al. |
| 5,015,255 A | 5/1991 | Kuslich |
| 5,026,373 A | 6/1991 | Ray et al. |
| 5,030,201 A | 7/1991 | Palestrant |
| 5,041,119 A | 8/1991 | Frigg et al. |
| 5,047,031 A | 9/1991 | Constantz |
| 5,053,212 A | 10/1991 | Constantz et al. |
| 5,055,104 A | 10/1991 | Ray |
| 5,059,193 A | 10/1991 | Kuslich |
| 5,062,845 A | 11/1991 | Kuslich et al. |
| 5,071,424 A | 12/1991 | Reger |
| 5,085,861 A | 2/1992 | Gerhart et al. |
| 5,108,402 A | 4/1992 | Chin |
| 5,108,404 A | 4/1992 | Scholten et al. |

(Continued)

FOREIGN PATENT DOCUMENTS

| | | |
|---|---|---|
| CN | 1449262 | 10/2003 |
| EP | 1 155 704 A1 | 11/2001 |
| EP | 1 372 748 B1 | 4/2009 |
| JP | 62-268562 | 11/1987 |
| JP | 2003-335686 | 11/2003 |
| KR | 20090016085 A * | 2/2009 |
| WO | WO 95/27518 | 10/1995 |
| WO | WO 00/09024 | 2/2000 |
| WO | WO 02/17794 | 3/2002 |
| WO | WO 2004/049961 | 6/2004 |
| WO | WO 2005/072128 A2 | 8/2005 |
| WO | WO 2006/082442 A1 | 8/2006 |
| WO | WO 2007/030616 | 3/2007 |
| WO | WO 2008/128342 A1 | 10/2008 |
| WO | WO 2009/129316 | 10/2009 |

OTHER PUBLICATIONS

Tabata et al. (Biomaterials, 1998, vol. 19, pp. 807-815).*

(Continued)

*Primary Examiner* — Brian-Yong Kwon
(74) *Attorney, Agent, or Firm* — Wolf, Greenfield & Sacks, P.C.

(57) ABSTRACT

Methods and articles of manufacture for treating patients with degenerative bone are provided. The methods are useful to improve bone quality in a localized area of a degenerative bone (e.g., osteopenic or osteoporotic bone), such as by improving BMD to be substantially similar to BMD in an average, healthy individual at the age of peak BMD. The methods can comprise forming a void in a localized area of the degenerative bone and filling the void with a bone regenerative material that causes generation of new, healthy, natural bone material. The articles of manufacture can comprise kits formed of various materials useful in the inventive methods for improving bone quality.

43 Claims, 19 Drawing Sheets

(56) References Cited

U.S. PATENT DOCUMENTS

| | | |
|---|---|---|
| 5,129,905 A | 7/1992 | Constantz |
| 5,156,610 A | 10/1992 | Reger |
| 5,158,564 A | 10/1992 | Schnepp-Pesch et al. |
| 5,178,845 A | 1/1993 | Constantz et al. |
| 5,224,488 A | 7/1993 | Neuffer |
| 5,242,461 A | 9/1993 | Kortenbach et al. |
| 5,263,953 A | 11/1993 | Bagby |
| 5,376,100 A | 12/1994 | Lefebvre |
| 5,403,317 A | 4/1995 | Bonutti |
| 5,431,671 A | 7/1995 | Nallakrishnan |
| 5,445,639 A | 8/1995 | Kuslich et al. |
| 5,489,307 A | 2/1996 | Kuslich et al. |
| 5,489,308 A | 2/1996 | Kuslich et al. |
| 5,508,342 A | 4/1996 | Antonucci et al. |
| 5,554,163 A | 9/1996 | Shturman |
| 5,556,429 A | 9/1996 | Felt |
| 5,568,337 A | 10/1996 | Eguchi et al. |
| 5,609,636 A | 3/1997 | Kohrs et al. |
| 5,618,549 A | 4/1997 | Patat et al. |
| 5,658,310 A | 8/1997 | Berger |
| 5,693,011 A | 12/1997 | Onik |
| 5,695,513 A | 12/1997 | Johnson et al. |
| 5,700,291 A | 12/1997 | Kuslich et al. |
| 5,709,683 A | 1/1998 | Bagby |
| 5,720,748 A | 2/1998 | Kuslich et al. |
| 5,720,749 A | 2/1998 | Rupp |
| 5,782,971 A | 7/1998 | Constantz et al. |
| 5,827,289 A | 10/1998 | Reiley et al. |
| 5,843,103 A | 12/1998 | Wulfman |
| 5,888,220 A | 3/1999 | Felt et al. |
| 5,925,056 A | 7/1999 | Thomas et al. |
| 5,928,239 A | 7/1999 | Mirza |
| 5,935,131 A | 8/1999 | Bonutti |
| 5,972,015 A | 10/1999 | Scribner et al. |
| 6,005,162 A | 12/1999 | Constantz |
| 6,022,362 A | 2/2000 | Lee et al. |
| 6,066,154 A | 5/2000 | Reiley et al. |
| 6,071,284 A | 6/2000 | Fox |
| 6,083,229 A | 7/2000 | Constantz et al. |
| 6,139,509 A | 10/2000 | Yuan et al. |
| 6,140,452 A | 10/2000 | Felt et al. |
| 6,149,655 A | 11/2000 | Constantz et al. |
| 6,171,312 B1 | 1/2001 | Beaty |
| 6,224,604 B1 | 5/2001 | Suddaby |
| 6,235,043 B1 | 5/2001 | Reiley et al. |
| 6,238,391 B1 | 5/2001 | Olsen et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,273,916 B1 | 8/2001 | Murphy |
| 6,296,639 B1 | 10/2001 | Truckai et al. |
| 6,319,255 B1 | 11/2001 | Grundei et al. |
| 6,383,188 B2 | 5/2002 | Kuslich et al. |
| 6,425,923 B1 | 7/2002 | Staloop et al. |
| 6,440,138 B1 | 8/2002 | Reiley et al. |
| 6,537,589 B1 * | 3/2003 | Chae et al. ............... 424/602 |
| 6,652,887 B1 | 11/2003 | Richelsoph et al. |
| 6,679,886 B2 | 1/2004 | Weikel et al. |
| 6,679,890 B2 | 1/2004 | Margulies et al. |
| 6,740,090 B1 | 5/2004 | Cragg et al. |
| 6,746,451 B2 | 6/2004 | Middleton et al. |
| 6,814,734 B2 | 11/2004 | Chappuis et al. |
| 6,827,720 B2 | 12/2004 | Leali |
| 7,211,266 B2 | 5/2007 | Cole et al |
| 7,229,971 B2 | 6/2007 | Tanaka et al. |
| 7,250,550 B2 | 7/2007 | Overby et al. |
| 7,252,672 B2 | 8/2007 | Yetkinler et al. |
| 7,261,717 B2 | 8/2007 | Yetkinler et al. |
| 7,261,718 B2 | 8/2007 | Constantz et al. |
| 7,291,179 B2 | 11/2007 | Miller et al. |
| 7,371,408 B1 | 5/2008 | Peterson et al. |
| 7,371,409 B2 | 5/2008 | Peterson et al. |
| 7,371,410 B2 | 5/2008 | Peterson |
| 7,413,753 B2 | 8/2008 | Li et al. |
| 7,419,680 B2 | 9/2008 | LeGeros |
| 7,507,257 B2 | 3/2009 | Cole et al. |
| 7,563,265 B1 | 7/2009 | Murphy |
| 7,621,952 B2 | 11/2009 | Truckai et al. |
| 7,622,139 B2 | 11/2009 | Li et al. |
| 7,658,768 B2 | 2/2010 | Miller et al. |
| 7,682,378 B2 | 3/2010 | Truckai et al. |
| 7,717,918 B2 | 5/2010 | Truckai et al. |
| 7,722,620 B2 | 5/2010 | Truckai et al. |
| 7,935,121 B2 | 5/2011 | Lidgren et al. |
| 2001/0034527 A1 | 10/2001 | Scribner et al. |
| 2002/0022856 A1 | 2/2002 | Johnson et al. |
| 2002/0120240 A1 | 8/2002 | Bagga et al. |
| 2003/0135214 A1 | 7/2003 | Fetto et al. |
| 2004/0267269 A1 | 12/2004 | Middleton et al. |
| 2005/0059979 A1 | 3/2005 | Yetkinler et al. |
| 2005/0070914 A1 | 3/2005 | Constantz et al. |
| 2005/0244451 A1 | 11/2005 | Diaz et al. |
| 2005/0244499 A1 | 11/2005 | Diaz et al. |
| 2006/0085009 A1 | 4/2006 | Truckai et al. |
| 2006/0085081 A1 | 4/2006 | Shadduck et al. |
| 2006/0089715 A1 | 4/2006 | Truckai et al. |
| 2006/0100706 A1 | 5/2006 | Shadduck et al. |
| 2006/0106459 A1 | 5/2006 | Truckai et al. |
| 2006/0149268 A1 | 7/2006 | Truckai et al. |
| 2006/0190000 A1 | 8/2006 | Schutz et al. |
| 2006/0229625 A1 | 10/2006 | Truckai et al. |
| 2006/0229628 A1 | 10/2006 | Truckai et al. |
| 2006/0264965 A1 | 11/2006 | Shadduck et al. |
| 2007/0118144 A1 | 5/2007 | Truckai et al. |
| 2007/0128248 A1 * | 6/2007 | Moseley et al. ............... 424/423 |
| 2007/0162043 A1 | 7/2007 | Truckai et al. |
| 2007/0191858 A1 | 8/2007 | Truckai et al. |
| 2007/0233148 A1 | 10/2007 | Truckai et al. |
| 2007/0259019 A1 * | 11/2007 | McKay ................ A61L 27/227 424/426 |
| 2007/0299453 A1 | 12/2007 | Constantz et al. |
| 2007/0299454 A1 | 12/2007 | Yetkinler et al. |
| 2008/0114364 A1 | 5/2008 | Goldin et al. |
| 2008/0132899 A1 | 6/2008 | Shadduck et al. |
| 2008/0172058 A1 | 7/2008 | Trieu et al. |
| 2008/0172059 A1 | 7/2008 | Trieu et al. |
| 2008/0172131 A1 | 7/2008 | Trieu et al. |
| 2008/0300603 A1 | 12/2008 | Gisep et al. |
| 2008/0317807 A1 | 12/2008 | Lu et al. |
| 2009/0112263 A1 | 4/2009 | Pool et al. |
| 2009/0149954 A1 * | 6/2009 | Hu et al. .................... 623/16.11 |
| 2010/0068239 A1 * | 3/2010 | Ripamonti .................... 424/423 |
| 2010/0076503 A1 | 3/2010 | Beyar et al. |
| 2010/0094302 A1 | 4/2010 | Pool et al. |
| 2010/0094303 A1 | 4/2010 | Chang et al. |
| 2010/0094304 A1 | 4/2010 | Pool |
| 2010/0094305 A1 | 4/2010 | Chang et al. |
| 2010/0094306 A1 | 4/2010 | Chang et al. |
| 2010/0137986 A1 | 6/2010 | Truckai et al. |
| 2011/0082417 A1 | 4/2011 | Lidgren et al. |
| 2011/0087161 A1 | 4/2011 | Lidgren et al. |

OTHER PUBLICATIONS

Bone density (Washington.edu, World Health Organization definitions, site updated on Jun. 18, 2008).*
Gauthier et al. (Biomaterials, Sep. 2005, vol. 26, pp. 5444-5453).*
Vani et al, (Journal of Material Science: Materials in Medicine, Published online Jun. 17, 2008, vol. 20, pp. S43-S48).*
Rotter et al (Spine, 2007, vol. 32, pp. 1400-1405).*
Wright Medical Technology, Inc., "Pro-Dense Delivers, Immediate Intra-Operative Strength and Predictable Bone Regeneration," SK267-707, 2007, 2 pages.*
Blum, (Pro-Dense Injectable Regenerative Graft: In Vitro and In Vivo observations, and a Proposed Mechanism of Action, Aug. 2008 (see Rev 8.08), Wright Medical Technology).*
Ripamonti et al (Biomaterials, 2014, vol. 35, pp. 9407-9422).*
PCT/US2011/042607 International Preliminary Report on Patentability issued Jan. 8, 2013.
Rotter et al., "Biomechanical In Vitro Testing of Human Osteoporotic Lumbar Vertebrae Following Prophylactic

(56) References Cited

OTHER PUBLICATIONS

Kyphosplasty with Different Candidate Materials," Spine (2007), vol. 32, No. 13, pp. 1400-1405.
Spivak et al., "Use of Hydroxyapitite in Spine Surgery," Eur Spine J (2001) 10:S19-S204.
Beckmann et al., "Femoroplasty—Augmentation of the Proximal Femur with a Composite Bone Cement—Feasibility, Biomechanical Properties and Osteosynthesis Potential," Med. Engineering & Physics (2007), pp. 755-764.
Urban et al., "Increased Bone Formation Using a Calcium Sulfate and Calcium Phosphate Composite Graft," Clinical Orthopaedics and Related Research, Lippincott Williams & Wilkins (2007), No. 000, pp. 000-000, 8 pages.
Gitelis et al., "Early Radiological Results with a Bio-Engineered Degradable Bone Graft Substitute for Bone Tumors," Presented at Musculoskeletal Tumor Society, May 10-12, 2007, St. Louis, MO.
Urban et al., Increased Amount and Strength of Restored Bone using a Slower-Resorbing Tri-Phasic $CASO_4$-Based Cement Compared to Conventional $CASO_4$ Pellets, Presented at the European Orthopaedic Research Society Annual Meeting, 2006, 3 pages.
Moseley et al., "In Vitro and In Vivo Evaluation of a Slower Resorbing Calcium Sulfate Cement," Presented at the Orthopaedic Research Society Annual Meeting, 2006, 1 page.
McCanless et al., In Vitro and In Vivo Evaluation of a Slower Resorbing Calcium Sulfate Cement, Presented at the European Society for Biomaterials Annual Meeting, 2005, 1 page.
Wright Medical Technology, Inc., 510(K) Summary of Safety and Effectiveness, Mar. 29, 2007, 5 pages.
Wright Medical Technology, Inc., "Pro-Dense Delivers, Predictable Bone Regeneration," SK373-708, 2008, 2 pages.
Wright Medical Technology, Inc., "Pro-Dense Case Studies and Surgical Techniques," (prior to Jul. 2, 2010), 29 pages.
Ripamonti, Ugo, "Soluble and Insoluble Signals Sculpt Osteogenesis in Angiogenesis," *World Journal of Biological Chemistry*, vol. 1, issue 5, pp. 109-132, May 26, 2010.
Patent Examination Report No. 2 from corresponding Australian Patent Application No. 2011272815 dated Jun. 18, 2014, 4 pages.
Amendment in Response to Patent Examination Report No. 2 from corresponding Australian Patent Application No. 2011272815 dated Sep. 5, 2014, 11 pages.
Notice of Acceptance from corresponding Australian Patent Application No. 2011272815 dated Oct. 15, 2014, 6 pages.
Application No. 2013-518715, Office Action mailed Apr. 8, 2014, 4 pgs.
Panchbhavi, MD, et al., "The Use of Calcium Sulfate and Calcium Phosphate Composite Graft to Augment Screw Purchase in Osteoporotic Ankles," Foot & Ankle International, 2008, 9 pgs.
"Change of Bone Mineral Density After Fixation of Tibial Defect with Calcium Sulfate Cement in Osteoporotic Rats," Academic Journal of Second Military Medical University, May 2008, vol. 29, No. 5, 3 pgs.
Communication Pursuant to Article 94(3) EPC mailed Nov. 29, 2013, Application No. 117342115.4, 6 pgs.
Ripamonti et al., "Induction of Bone Formation by Transforming Grown factor-$\beta_2$ in the Non-Human Primate *Papio ursinus* and its Modulation by Skeletal Muscle Responding Stem Cells," *Cell Proliferation*, 2010, 43, 207-218.
Office Action for Japanese Application No. 2015-137638 mailed Jul. 7, 2016.
Office Action for Taiwanese Application No. 100122879 dated May 25, 2016.
Australian Examination Report for Application No. 2011272815 dated May 28, 2013.
Australian Notice of Acceptance for Application No. 2015200464 dated Nov. 12, 2015.
Canadian Office Action for Application No. 2803373 dated Jan. 15, 2014.
Canadian Office Action for Application No. 2803373 dated Feb. 19, 2015.
Canadian Office Action for Application No. 2803373 dated Dec. 22, 2015.
Chinese Office Action for Application No. 201180038621.3 dated Apr. 1, 2014.
Chinese Office Action for Application No. 201180038621.3 dated Dec. 3, 2014.
Chinese Office Action for Application No. 201180038621.3 dated Jun. 30, 2015.
Chinese Notification on Grant for Application No. 201180038621.3 dated Dec. 7, 2015.
European Office Action for Application No. 11734215.4 dated Jul. 11, 2014.
Extended European Search Report for Application No. 15187629.9 dated Jan. 22, 2016.
Japanese Decision of Rejection for Application No. 2013-518715 dated Mar. 10, 2015.
Japanese Decision to Grant for Application No. 2013-518715 dated Oct. 13, 2015.
Korean Notice of Preliminary Rejection for Application No. 1020137002739 dated Jan. 1, 2014.
Korean Notice of Final Rejection for Application No. 10-2013-7002739 dated Nov. 19, 2014.
Korean Notice of Second Final Rejection for Application No. 10-2013-7002739 dated Mar. 16, 2015.
Korean Notice of Preliminary Rejection for Application No. 10-2015-7015910 dated Jul. 6, 2015.
Korean Notice of Final Rejection for Application No. 10-2015-7015910 dated Feb. 16, 2016.
Mexican Office Action for Application No. MX/a/2013/000205 dated Mar. 26, 2014.
Mexican Office Action for Application No. MX/a/2013/000205 dated Dec. 5, 2014.
Mexican Office Action for Application No. MX/a/2013/000205 dated Jul. 9, 2015.
Mexican Notice of Allowance for Application No. MX/a/2013/000205 dated Feb. 5, 2016.
Russian Office Action for Application No. 2013104512 dated Dec. 6, 2013.
Russian Office Action for Application No. 2013104512 dated Jun. 3, 2014.
Russian Office Action for Application No. 2013104512 dated Dec. 5, 2014.
Russian Minutes of the Examiner's interview for Application No. 2013104512 dated Aug. 5, 2015.
Russian Decision to Grant for Application No. 2013104512 dated Dec. 25, 2015.
International Search Report for Application No. PCT/US2011/042607 mailed Nov. 16, 2011.
South African Notice of Acceptance for Application No. 2013/00424 dated Jul. 29, 2014.

\* cited by examiner

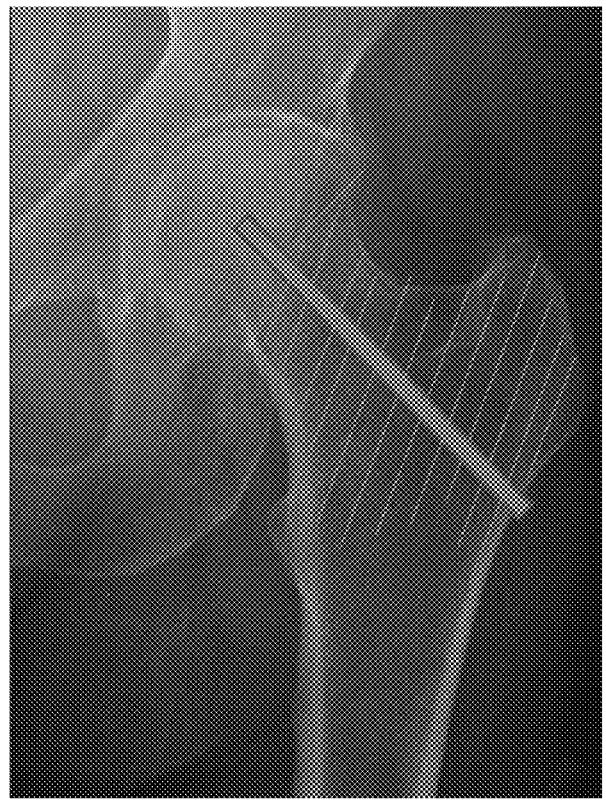
FIG. 4
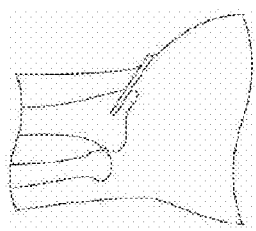 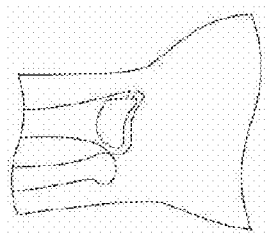 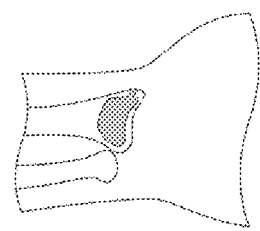
FIG. 5a     FIG. 5b     FIG. 5c

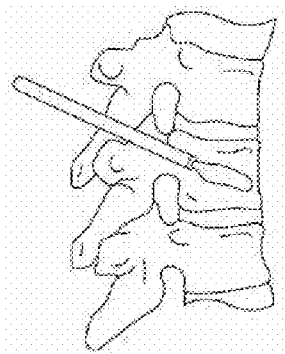
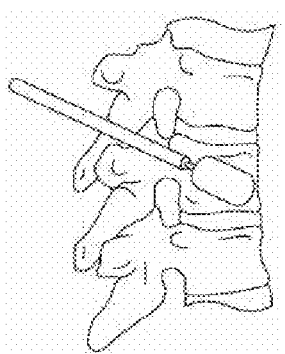
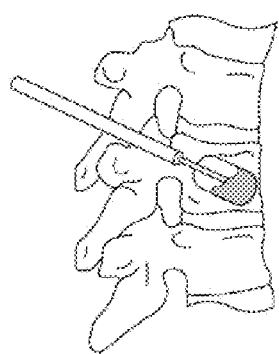
FIG. 6a      FIG. 6b      Fig. 6c
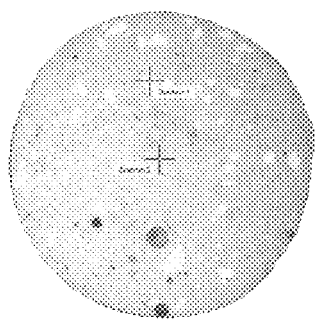
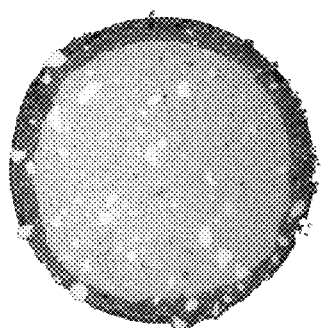
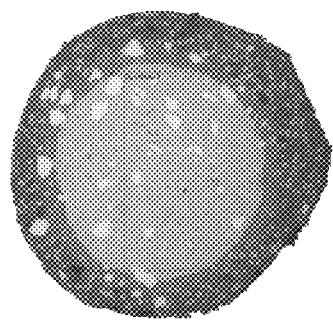
FIG. 7a      FIG. 7b      FIG. 7c
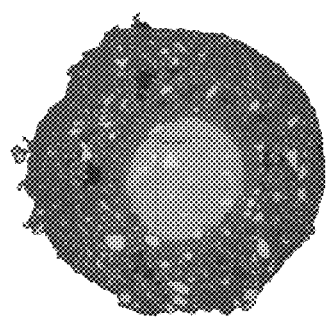
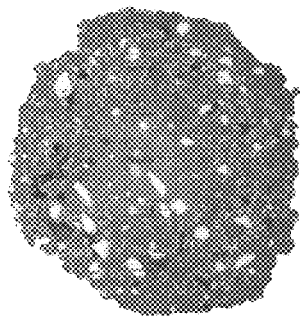
FIG. 7d      FIG. 7e

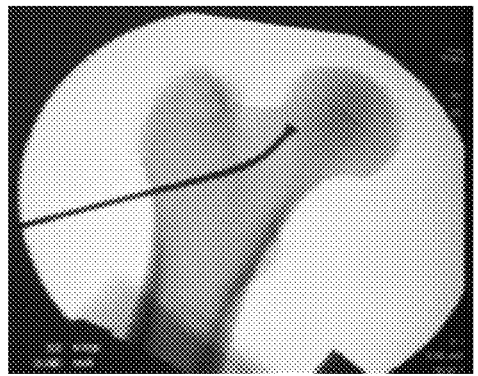
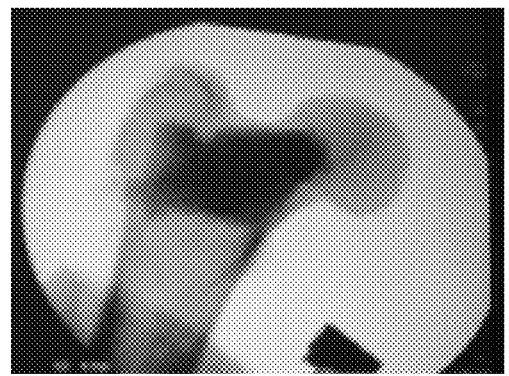
*FIG. 20*          *FIG. 21*
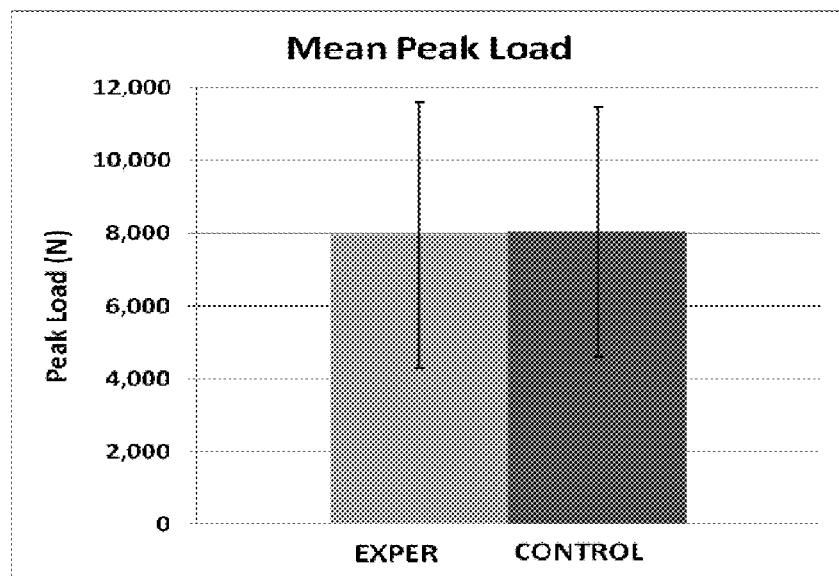
*FIG. 22*

METHODS OF TREATING DEGENERATIVE BONE CONDITIONS

CROSS-REFERENCE TO RELATED APPLICATIONS

The present patent application claims priority to Taiwan Patent Application 100122879, filed Jun. 29, 2011 which claims the benefit of U.S. Provisional Patent Application No. 61/361,177, filed Jul. 2, 2010, both of which are incorporated herein by reference in their entirety.

FIELD OF THE INVENTION

The present invention relates to methods of treating patients suffering from bone degeneration, such as osteopenia and osteoporosis. More particularly, the invention provides methods of treating patients suffering from bone degeneration by replacing at least a portion of the degenerated bone material.

BACKGROUND

Bone mineral density (BMD) is a term that is commonly recognized as relating to the amount of calcified matter present per square centimeter of bone. It is understood that the term does not refer to a true density (as in mass per volume of material) but rather is used to communicate information about the strength of the bone and the susceptibility of the bone to fracture. Typically, BMD is evaluated using methods, such as Dual Energy X-ray Absorptiometry (or DEXA scan), ultrasound, and Quantitative Computed Tomography (QCT). Of the foregoing, DEXA scan often is considered to be the most reliable evaluation of BMD. For example, ultrasound is generally limited to evaluation of the calcaneus bone and is not useful for directly measuring sites common to osteoporotic fracture, such as the hip and spine. QCT typically is used with the spine and must be done following strict protocols in laboratories to provide acceptable reproducibility. Further test methods for evaluating BMD include single photon absorptiometry (SPA), dual photon absorptiometry (DPA), digital X-ray radiogammetry (DXR), and single energy X-ray absorptiometry (SEXA).

BMD is a highly important physical characteristic since it can be a direct indicator of susceptibility to fracture. In most adult populations, BMD peaks around the age of 30-35 and tends to slowly decline thereafter. The reduction in BMD arises from a decline in new bone cell production such that the resorption of existing bone cells by the body exceeds the rate of new bone cell production. FIG. 1 (which is available online at http://courses.washington.edu/bonephys/opbmd.html) illustrates the typical decline in BMD (shown in mg/cm$^2$) for adults and shows how the decline can vary based upon both race and gender. Menopause in women is a highly significant event in relation to BMD as the decrease in BMD sharply accelerates for a period of time after menopause. Thus, post-menopausal women typically are encouraged to have BMD testing regularly to assess if treatment is required and what type of treatment should be pursued. The National Osteoporosis Foundation recommends BMD testing for the following individuals: all women aged 65 and older regardless of risk factors; younger postmenopausal women with one or more risk factors; postmenopausal women who present with fractures (to confirm the diagnosis and determine disease severity); estrogen deficient women at clinical risk for osteoporosis; individuals with vertebral abnormalities; individuals receiving, or planning to receive, long-term glucocorticoid (steroid) therapy; individuals with primary hyperparathyroidism; individuals being monitored to assess the response or efficacy of an approved osteoporosis drug therapy; and individuals with a history of eating disorders.

Reduced BMD commonly is recognized in relation to the conditions of osteopenia and osteoporosis, and the existence of these conditions is defined upon a patient's score from a BMD test, particularly the T-score from a DEXA scan. The T-score from a DEXA scan is a normalized value that indicates how a patient's BMD compares to the average of a young adult at peak BMD. The normalized value is expressed in standard deviations from the average. Thus, a T-score of 0 indicates no difference in BMD compared to the average young adult, a negative T-score indicates BMD below the average, and a positive T-score indicates BMD above the average. T-score is a normalized value because the average value varies depending upon race and gender. T-score also can vary from one bone to another in the same individual. Generally, a bone with a T-score of greater than −1 is considered to be within the normal range (although the negative score still indicates BMD below the normalized average). The condition of osteopenia typically is considered to exist for bone with a T-score of −1 to −2.5. The condition of osteoporosis typically is considered to exist for bone with a T-score of less than −2.5.

BMD can be correlated to bone strength and thus can be a predictor of risk for bone fracture. In general, the risk for bone fracture is expected to increase with every standard deviation below normal. In the elderly, bone fracture (particularly hip or vertebral fractures) can be correlated to increased mortality. Thus, improving BMD can be a goal of medical intervention in osteopenic and/or osteoporotic patients since BMD can be correlated to increased risk for fracture. While several interventions have been tried, there still remains a need in the art for treatments that can effectively increase BMD.

Treatment and prophylaxis of bone degeneration (i.e., loss of BMD) can take on many faces. Prevention typically starts in childhood with exercise and proper nutrition that includes sufficient calcium and vitamin D as both exercise and nutrition have been shown to be necessary for maximum BMD development. This is important because decrease in BMD with age has been shown to be slower when actual BMD at the peak age is greater.

When conditions of osteopenia and osteoporosis are present, many different therapies are available. Estrogen treatment of postmenopausal women may slow onset and/or progression of bone degeneration. Similarly, Selective Estrogen Receptor Modulators (SERM's), such as raloxefine, may be used to simulate increased estrogen in the body and thus slow bone loss. Calcitonin may be prescribed and is a material that is naturally produced by cells in the thyroid gland. Calcitonin acts directly on osteoclasts (via receptors on the cell surface for calcitonin) to modify the osteoclasts and thus stop bone resorption. Bisphosphonates, such as etidronate (DIDRONEL®), pamidronate (AREDIA®), alendronate (FOSAMAX®), risedronate (ACTONEL®), zoledronate (ZOMETA® or RECLAST®), and ibandronate (BONIVA®), can increase bone strength through increased mineralization density and decrease bone resorption. The bisphosphonates are all related to pyrophosphate, which is a byproduct of cellular metabolism and is a natural circulating inhibitor of mineralization in the blood and urine. Although pyrophosphates cannot enter bones (i.e., because the cell lining destroys pyrophosphate with alkaline phosphatase), bisphosphonates can enter the bone (and attach very strongly) due to chemical substitution in the compounds. Although such drugs may provide some level of usefulness, recent studies have suggested that long-term use of bisphosphonates can increase the risk of spontaneous subtrochanteric and femoral shaft fractures (i.e., atypical fractures). Denosumab (PROLIA®) is another pharmaceutical that was recently approved by the U.S. Food and Drug Administration for twice-a-year injections in osteoporotic patients with high fracture risk or patients that cannot tolerate other treatments. Denosumab is a fully human, monoclonal antibody that binds the RANK ligand and alters the body's natural bone remodeling process. Although long-term effects of the use of this antibody are not yet known, doctors have been warned to monitor patients for adverse reactions, such as osteonecrosis of the jaw, atypical fractures, and delayed fracture healing. Further, since the antibody alters the body's immune system, there has been evidence that use of the antibody can increase risk of serious infection in the patient. Yet another treatment, teriparatide (FORTEO®), is a recombinant parathyroid hormone (rPTH) that has the paradoxical effect of increasing bone mass by altering the pattern of exposure to the body's natural parathyroid hormone (PTH) and thus altering the skeletal effect of chronic PTH elevation, which can result in increased bone breakdown, a loss of calcium, and osteoporosis. Through activation of various bone metabolic pathways, the rPTH increases the number of active osteoblasts, decreases the naturally programmed death of osteoblast cells, and recruits bone-lining cells as osteoblasts. The drug appears to act largely upon the bone-building osteoblast cells and stimulating them to over activity. Safety studies in rats indicated a possibly increased risk of osteosarcoma associated with use of rPTH. Thus, there remains a need in the art for treatments that do not require long-term medication use with possible effects that, although unintended, may still be harmful.

Non-pharmaceutical treatments typically are used only after a fracture occurs. For example, fractures (particularly vertebral) may be treated by instant fixation wherein poly (methyl methacrylate) cement (typically referred to as "bone cement") or a similar non-resorbable material, is inserted into the fracture to permanently harden and "fix" the bone in place. Although such treatments can attend to the presenting fracture, the unnatural physical properties (i.e., hardness, modulus, etc.) of the bone after the treatment are believed to increase the possibility of fracture of adjacent bone, particularly where the adjacent bone is in an advanced state of osteoporosis. Moreover, such treatments do not result in formation of natural bone in the fracture but rather function as non-resorbable bone replacements.

Despite the presence of pharmaceutical and surgical treatments for bone degeneration and fracture, there remains a need in the art for further treatments that can increase BMD in key areas to reduce risk of fractures and concomitant health risks, including death. Particularly, it would be useful to have means for treatments that target specific areas of the skeleton at high fracture risk by actually forming new, healthy (i.e., normal) bone material. Such treatments would not be subject to the current limitations of the art.

SUMMARY OF THE INVENTION

The present invention provides for improvement of bone structure in patients suffering from a degenerative bone condition, such as osteopenia or osteoporosis. Specifically, the invention allows for selective replacement of degenerated bone material in localized areas of bones with a bone regenerative material that is resorbed by the body over time and replaced by newly generated bone material. Beneficially, the newly formed bone material is bone material that is natural to the patient in that it is not a bone transplant (e.g., cadaver bone) or a non-resorbable bone replacement (e.g., bone cement). Moreover, the newly formed bone material is not degenerative in nature but is healthy bone material in the sense that the bone material (which can include the immediately surrounding portions of the bone) exhibits characteristics, such as BMD and compressive strength, that make the newly formed bone material, in certain embodiments, substantially similar to bone material in an average, healthy, 30 year old individual (i.e., at the age where BMD is typically at its peak). In other embodiments, the newly generated bone can be characterized as being improved in relation to osteopenic bone or osteoporotic bone. The improvement further may be characterized in relation to a specific scale, such at in relation to T-score from DEXA scans.

In certain embodiments, the invention thus can be directed to a method of treating a patient suffering from a degenerative bone condition. Specifically, the method can comprise forming a void in a localized area of a bone, such as by mechanical debridement of the degenerated bone material or otherwise breaking apart the degenerated bone material to form the void. Optionally, a portion of the degenerated bone material can be removed from the formed void. In some embodiments, the degenerated bone material may remain in the void but, because of the degenerated state of the bone material, the material does not take up a significant volume of the formed void. The method further can comprise at least partially filling the formed void with a bone regenerative material.

In certain embodiments, the degenerative bone condition specifically can be selected from the group consisting of osteopenia and osteoporosis. While the patient to be treated can be suffering from any condition that causes bone degeneration, the terms osteopenia and osteoporosis may be considered to generally encompass patients suffering from any condition that causes a reduction in BMD to the extent that a T-score calculated by DEXA scan is below a certain threshold. For example, since osteopenia technically is defined as being present when a T-score for the area of bone scanned is less than −1.0, and since osteoporosis technically is defined as being present when a T-score for the area of bone scanned is less than −2.5, these clinical terms (and the present methods of treatment thereof) can be considered applicable to treating bone degeneration regardless of the underlying condition from which the bone loss arises (whether it be from natural bone loss with aging or as a side effect of a specific underlying disease or medical treatment (e.g., steroid treatments).

In specific embodiments, the bone regenerative material used according to the invention can comprise an osteoinductive material, osteoconductive material, osteogenic material, osteopromotive material, or osteophilic material. Preferably, the bone regenerative material comprises calcium sulfate. In further embodiments, the bone regenerative material may comprise calcium phosphate. In other embodiments, the bone regenerative material may comprise tricalcium phosphate granules. In specific embodiments, the bone regenerative material may comprise a combination of all three types of materials. In some embodiments, the bone regenerative material can comprise a material exhibiting a tri-phasic resorption profile in vivo.

The bone regenerative material may be characterized as being a material that causes formation of new, non-degenerated bone material in the formed void. Specifically, the non-degenerated bone material may have a density that is substantially identical to normal bone (i.e., bone from a typical, healthy 30 year old individual), particularly bone from the same generalized area. Specifically, this may be characterized in relation to a T-score measured by Dual Energy X-ray Absorptiometry (DEXA). Preferably, the portion of the bone including the newly formed bone material has a T-score that is greater than −1.0, greater than −0.5, or is at least 0.

In certain embodiments, the bone regenerative material may be characterized as promoting remodeling of the localized area of the bone over time to be substantially identical to normal bone. Specifically, the remodeling may be indicated by the localized area of the bone (after implantation of the bone regenerative material into the void) initially having a T-score that is greater than 2.0, the T-score gradually reducing over time to have a T-score that is about 0 to about 2. Preferably, the remodeled, localized area of the bone maintains a T-score of greater than about 0 for a time of at least 1 year measured from the time of new bone material formation.

In further embodiments, the bone regenerative material may be characterized as promoting formation of new bone material of substantially normal BMD in the area of the bone adjacent the formed void. This can be described as a gradient effect, which is discussed further herein.

The bone for void formation can be any bone that is degenerative in nature and would be a desirable area for treatment according to the invention (e.g., to prevent future fractures). In some embodiments, the bone can be selected from the group consisting of hip, femur, vertebrae, radius, ulna, humerus, tibia, and fibula.

In further embodiments, the invention specifically can be characterized as providing a method of increasing BMD in a localized area of a bone. The method can comprise forming a void in the localized area of the bone and optionally removing a content of the cleared bone material. The method further can comprise at least partially filling the formed void with a bone regenerative material such that new bone material is generated within the void, the density of the generated bone material being greater than the density of the bone material that was originally present in the void space. Preferably, the increase in BMD is indicated by the generated bone material having a T-score that is at least 0.5 units greater than the T-score of the native bone material prior to being removed to form the void. Even greater improvements in T-score can be seen, as described further herein. In specific embodiments, the T-score of the native bone material prior to being removed to form the void can be less than about −1.0 and the generated bone material can have a T-score that is greater than −1.0 or that is at least about −0.5. The invention further is beneficial in that the increase in BMD may be maintained for a time of at least about 1 year measured from the time of new bone material generation.

In still further embodiments, the invention may be characterized as providing a method of creating a defined BMD profile in a localized area of a bone. As further described herein, the methods of the invention surprisingly not only improve bone quality in the localized area of the bone treated, but also can provide a specific BMD profile wherein BMD in the localized area is dramatically improved and is followed by a gradual return to a substantially normal density. The inventive method can comprise forming a void in the localized area of the bone and at least partially filling the formed void with a bone regenerative material such that new bone material is generated within the void over time and at least a portion of the bone regenerative material is resorbed. Preferably, a majority of the bone regenerative material is resorbed. The BMD profile in the localized area of the bone can be such that T-score increases from an initial score of less than −1, as measured prior to forming the void, to a maximum score of at least about 5 within a defined time from the time of filling the void with the bone regenerative material. Thereafter, the T-score in the localized area of the bone can decrease over time to a score of about −0.5 to about 2.0 (i.e., a substantially normal range).

In yet further embodiments, the present invention can be characterized as providing methods of remodeling a localized area of degenerative bone to be substantially identical to normal bone. Similar to the above, the inventive methods surprisingly can function to essentially reset the bone quality in the localized area of the bone treated. In other words, the bone that is in a degenerative state is replaced with a bone regenerative material, and the in-growth of new, natural bone material is not degenerated bone material but is substantially normal bone material. Thus, the bone in the localized area can be characterized as being remodeled from degenerated bone material to normal bone material. As more fully described below, the remodeling does not refer to a natural process spontaneously occurring in the body but refers to a manipulated restoration of bone quality through carrying out of the inventive methods. Specifically, the method can comprise forming a void in the localized area of the bone and at least partially filling the formed void with a bone regenerative material thereby generating in-growth of new bone material in the formed void. Preferably, the bone material in the localized area before forming the void has a T-score of less than −1 indicating bone degeneration, and wherein new bone material present after remodeling has a T-score of greater than −1.0 (more preferably greater than about 0) indicating the bone in the localized area has been remodeled to be substantially identical to normal bone.

In still further embodiments, the invention can be characterized as providing methods of restoring vertebral body height or correcting angular deformity in a fractured vertebra (particularly an osteopenic or osteoporotic vertebra) by causing in-growth of new bone material that is substantially identical to normal bone. The method can comprise forming a void in the area of the fracture, which can include mechanically increasing the space in the fracture and optionally removing a content of the bone material in the area of the fracture. The method further can comprise at least partially filling the formed void with a bone regenerative material such that new bone material is generated within the void over time. Preferably, the new bone material has a T-score indicating the new bone material is substantially identical to normal bone (e.g., a T-score of at least −0.5 or at least 0).

In even further embodiments, the present invention can be characterized as providing methods of improving bone quality at a localized area of a bone. As described herein, bone quality can be described in relation to measurable characteristics, such as BMD, compressive strength, and resistance to fracture. Thus, the methods of improving bone quality can be evidenced by an increase in one or both of these characteristics (as well as other measurable characteristics that may be useful for defining bone quality). In some embodiments, the method can comprise replacing a volume of degenerated bone material from a localized area of bone having a T-score of less than −1.0 with newly formed, natural bone material such that the same localized area of the bone has a T-score of greater than −1.0 (preferably at least −0.5 or at least 0). In further preferred embodiments, the T-score of the localized area of bone after the inventive procedure can exceed the T-score of the degenerated bone by at least 1.0 unit. In specific embodiments, the replacing of the degenerated bone material can comprise forming a void in the localized area of the bone and at least partially filling the formed void with a bone regenerative material thereby generating in-growth of new, natural bone material in the formed void.

In other aspects, the invention can provide various materials for use in methods of treating degenerated bone material. Such materials specifically may be provided in a combination, such as a kit, to facilitating ease of carrying out the various inventive methods. Thus, the invention may be characterized as providing a kit for use in replacing degenerated bone material in a localized area of a bone with a bone regenerative material that promotes generation of new bone material that is substantially identical to normal bone.

In some embodiments, a kit according to the invention can comprise one or more of a cannulated drill bit, a guide wire, a working cannula, a debridement probe, an amount of the bone regenerative material suitable for filling a void in the localized area of the bone, and an injection device for delivering the bone regenerative material. In further embodiments, a kit according to the invention may comprise an instrument bender suitable for adjusting the geometry of a probe (i.e., any device that may function to break away bone material or otherwise debride or to tamp or pack a material into a void) to accommodate the anatomy of the void in the localized area of the bone. Specifically, the probe device may comprise a head that is shaped to accommodate the anatomy of the void in the localized area of the bone. In other words, the probe may be pre-bent to a defined angle (or multiple angles formed by multiple bends). In further embodiments, a kit according to the invention may comprise one or more of a tissue protector, cannulated obdurator, guidewire, drill, flexible working cannula, working cannula obdurator, debridement probe, and suction/irrigation device. A kit further may include an instruction set in any form suitable to teach, illustrate, describe, or otherwise show how to use the various components of the kit to treat a patient suffering from a degenerative bone condition.

BRIEF DESCRIPTION OF THE DRAWINGS

Having thus generally described the invention, reference is made herein to the various drawings presented herewith, wherein:

FIG. 4 is an enhanced radiograph of a proximal femur illustrating embodiments of the invention wherein filled voids of varying shapes and dimensions may be made for filling with a bone regenerative material;

FIGS. 5a-5c are illustrations showing defined steps of a surgical technique for replacing degenerated bone material in the distal radius of a patient according to one embodiment of the invention;

FIGS. 6a-6c illustrate defined steps of a surgical technique for replacing degenerated bone material in the vertebra of a patient according to one embodiment of the invention;

FIGS. 7a-7e are scanning electron microscopy images showing changes over time in a bone regenerative material used as an implant according to one embodiment of the invention, such changes facilitating controlled in-growth of new bone material;

FIG. 20 is a radiograph showing insertion of a debridement probe used in creation of a void in a proximal femur according to one embodiment of the invention;

FIG. 21 is a radiograph showing a graft material in situ filling a formed void according to one embodiment of the invention;

FIG. 22 is a graph showing the mean peak load observed across pairs of matched cadaver femurs tested for fracture resistance after void formation and filling with a bone regenerative material according to one embodiment of the invention;

DETAILED DESCRIPTION OF THE INVENTION

Figure 1:
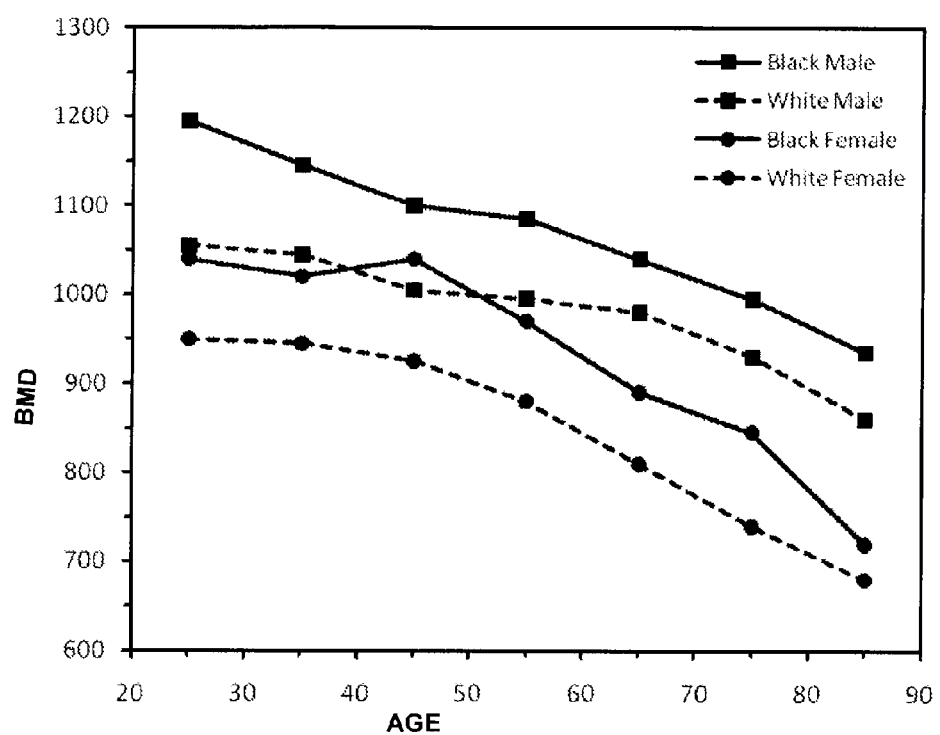
FIG. 1 is a graph showing the typical decline in BMD (mg/cm$^2$) of the total hip in relation to age, gender, and ethnicity.

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention arises from the recognition of the ability to use various bone regenerative materials in replacement therapy for degenerative bone material. Particularly, it has been found that when degenerated bone material in a localized area of a bone is replaced by certain bone regenerative materials, new bone material is generated in the localized area of the bone as the bone regenerative materials are resorbed by the body. Surprisingly, it has been found that even when existing bone is in an advanced state of degeneration (e.g., osteoporosis), the body's ability to form new, healthy bone material that is substantially identical to normal bone is retained.

As used herein, the term "normal bone" or "normal bone material" is intended to refer to bone or bone material exhibiting the characteristics of healthy bone for a person (preferably of the same gender and race as the patient being treated) at the age when BMD typically is at its peak (i.e., around 30-35 years of age). In other words, according to one embodiment, it has been found that when an osteoporotic, elderly, Caucasian woman is treated according to the present invention, it is possible to grow new bone that is not osteoporotic but is substantially identical (i.e., in relation to BMD and/or compressive strength) to bone in the average Caucasian woman of age 30-35. Of course, such effects can be seen in both genders and across all races. Thus, the present invention provides the ability to locally change bone quality. More specifically, it is possible according to the invention to upgrade bone quality in a localized area from a degenerative state to a less degenerative state, preferably from a degenerative state to a substantially normal state. In other words, it is possible to upgrade bone quality in a localized area such that the bone material has a density that is substantially identical to the BMD of a person of the same race and gender at the average age of peak BMD (i.e., about 30-35 years old). Such localized area can include the newly formed bone as well as surrounding portions of the bone that were not replaced according to the invention.

As described above, there are multiple methods in the art for evaluating BMD, and any suitable method capable of quantifying BMD in a meaningful manner to identify states of normalcy and degeneration could be used in relation to the present invention. For ease of understanding, the effectiveness of the inventive methods is described throughout the present disclosure in relation to T-score as evaluated by Dual Energy X-ray Absorptiometry (DEXA) scanning. This is a well-recognized method of evaluating BMD. Moreover, since common conditions of bone degeneration can actually be defined by a patient's T-score, DEXA scan results provide a meaningful way for quantifying the results of the present invention in relation to improvements in BMD. DEXA scanning machines typically report BMD in units of $g/cm^2$. Because of differences in machine manufacturers, however, reports of BMD in units of $g/cm^2$ are not standardized. To assist in standardization, T-score can be equated to BMD in $mg/cm^2$ according to the following equation:

$$T\text{-score} = (BMD - \text{reference BMD})/SD$$

wherein reference BMD and standard deviation (SD) are referenced to an average patient of age 30-35 where BMD is expected to be at its peak, and wherein BMD and SD both are provided in units of $mg/cm^2$. The resulting T-score provides a consistent, reproducible evaluation of BMD that can be used to provide evidence of changes in BMD. In the U.S., T-score typically is calculated using a reference of the same race and gender. According to World Health Organization (WHO) standards, T-score is evaluated based on reference values for Caucasian females. For ease of reference, T-scores discussed herein were obtained by DEXA scans using a Hologic Delphi™ Bone Densitometer (available from Hologic, Inc., Danbury Conn.). Another means for characterizing scan data is Z-score, which is the number of standard deviations away from the mean for persons of the same age, gender, and ethnicity as the tested patient. The invention also encompasses, however, further methods for evaluating increases in bone quality—e.g., BMD, compressive strength, or resistance to fracture—such as could be achieved using one or more alternative testing methods—e.g., ultrasound, QCT, SPA, DPA, DXR, or SEXA.

In specific embodiments, the benefits of the invention can be characterized based on the relative improvement in BMD after employing one or more of the inventive methods. By "relative improvement" is meant the improvement in the bone quality factor (e.g., BMD, compressive strength, or resistance to fracture) in relation to the condition of the localized area of the bone prior to onset of treatment according to the invention. This manner of characterizing the invention can be independent of achieving a standard intended to define normal bone conditions in young, healthy adults. For example, relative improvement specifically may take into consideration the improvement in bone quality for the individual patient and the effect on quality of life. For example, a patient with an extremely poor BMD in the proximal femur (e.g., −3 T-score) could have a significantly improved quality of life through improvement in the T-score of perhaps 1.5 units. The ending T-score of −1.5 would still indicate an osteopenic state, but the relative improvement in the bone quality in the area of the proximal femur could be sufficiently significant to be indicative of an effective treatment regardless of whether the defined, normal BMD is achieved. In some embodiments, however, effective treatment can be expressly related to the ability to achieve a normal BMD for the localized area of the bone treated.

In some embodiments, the methods of the present invention can be described in relation to increases in BMD as evidenced by increases in T-score (either of the specific bone material that is replaced and new bone material that is generated or of the localized area of the bone generally), which can be reproduced by one of skill in the art using the methods already described herein. Thus, the benefits of the invention can be described in relation to an improved T-score, which can be correlated to a lessened state of degeneration (i.e., a relative improvement in BMD) or to a change in BMD such that the bone is categorized as normal (i.e., non-degenerative) or greater. In some embodiments, T-score may be improved by at least 0.25 units, at least 0.5 units, at least 0.75 units, at least 1.0 unit, at least 1.25 units, at least 1.5 units, at least 1.75 units, at least 2.0 units, at least 2.25 units, at least 2.5 units, at least 2.75 units, or at least 3.0 units. In other embodiments, BMD may be increased such that the T-score is at least at a minimum level. For example, BMD may be increased such that T-score is at least −1, at least −0.75, at least −0.5, at least −0.25, at least 0, at least 0.25, at least 0.5, at least 0.75, at least 1.0, at least 1.25, at least 1.5, at least 1.75, at least 2.0, at least 2.5, at least 3.0, at least 4.0, or at least 5.0. In other embodiments, T-score may be defined as being greater than −1, which can be indicative of BMD falling within an accepted normal range. In other embodiment, T-score may be about −1.0 to about 2.0, about −1.0 to about 1.0, about −1.0 to about 0.5, about −1.0 to about 0, about −0.5 to about 2.0, about −0.5 to about 1.5, about −0.5 to about 1.0, about −0.5 to about 0.5, about 0 to about 2.0, about 0 to about 1.5, or about 0 to about 1.0. Moreover, degenerated bone material according to the invention may be described as bone having a T-score of less than −1.0, less than about −1.5, less than −2.0, less than −2.5, or less than −3.0. The importance of the above values are more readily evident from the further description of the invention provided below.

The invention as described herein could find use with virtually any bone in a patient's body where improved BMD is desired. In specific embodiments, the replacement methods are expected to be used only in localized areas of bone. In other words, entire lengths of bone are not replaced or regenerated, but only discrete or localized sections or areas of a particular bone are replaced. The methods preferably are used in localized areas of a bone because the methods make use of the body's natural ability to resorb the bone regenerative materials that are used and replace the materials with newly generated bone. In specific embodiments, it has been found that such bone regeneration can take place by in-growth of bone material from the surrounding bone material. For clarity, it is understood that, in certain embodiments, the words "bone" and "bone material" can take on independent meanings. Specifically, "bone" may refer to the general, overall anatomical structure (e.g., the femur or a vertebra) while "bone material" may refer to a plurality of bone cells and calcified extracellular matrices that are present (or generated) in and around a discrete, localized area of a greater bone structure. Thus, where bone material is removed, the overall bone remains. Moreover, where a void is formed in a bone, new bone material can be generated therein.

In some embodiments, the methods of the invention particularly may be carried out in bones that are particularly subject to possible fracture in a patient suffering from a bone degenerative condition. Such bone degenerative condition can refer to any condition that is characterized by a loss of BMD. In specific embodiments, the bone degenerative condition can refer to osteopenia or osteoporosis. Since these conditions can be defined in relation to a T-score within a defined range, the terms can be used herein to refer to bone degeneration generally regardless of whether the degeneration arises from natural bone cell resorption that is not sufficiently countered by new bone cell production or whether the degeneration arises from a separate condition that causes bone degeneration as a symptom or side effect.

In specific embodiments, the inventive methods may be carried out on bone associated with the hip joint. This particularly may encompass the bone structures recognized generally as the hip bone, innominate bone, or coxal bone (i.e., the ischium, ilium, and pubis), as well as the proximal portion of the femur and the subtrochanteric portion of the femur (although the femur in general is encompassed by the invention). Portions of the femur particularly of interest according to the invention are the head, the neck, the greater trochanter, and the lesser trochanter, as well as the area recognized as "Ward's area" (or "Ward's triangle"). Such areas of the bone particularly are subject to fracture associated with falls in the elderly or atypical fractures.

Other bones that may be treated according to the present invention include the vertebrae and other major bones associated with the legs and arms, such as the radius, ulna, humerus, tibia, and fibula. Of particular interest, in addition to the bones of the hip area, are the vertebrae, the distal radius, and specific bone segments that may be subject to atypical fracture.

The invention makes use of specific bone regenerative materials. This term can include various materials that can be useful in regenerating bone or bone material, particularly materials that also may be filled into a void and promote in-growth of new bone material into the filled void. Thus, in some embodiments, the bone regenerative material may be characterized as a bone filler material. Preferably, the bone regenerative material includes a substantial proportion of material that is resorbable by the mammalian body. For example, the bone regenerative material may comprise at least 40%, at least 50% by weight, at least 60% by weight, at least 70% by weight, at least 80% by weight, or at least 90% by weight of materials that are resorbable by the mammalian body. Further, it is preferable for the material to resorb at a rate substantially similar to the rate of in-growth of new bone material. In some embodiments, the bone regenerative material may include a content of material that is not readily resorbable but that is otherwise compatible with formation of new bone material (e.g., that may be taken up into the structure of the bone including the newly generated bone material).

In certain embodiments, the bone regenerative material may be a material that is recognized as an osteoconductive or osteoinductive material. By "osteoinductive" is meant materials that lead to a mitogenesis of undifferentiated perivascular mesenchymal cells leading to the formation of osteoprogenitor cells (i.e., cells with the capacity to form new bone or bone material). By "osteoconductive" is meant materials that facilitate blood vessel incursion and new bone or bone material formation into a defined passive trellis structure. Various compounds, minerals, proteins, and the like are known to exhibit osteoinductive, osteoconductive, osteogenic, osteopromotive, or osteophilic activity. Accordingly, such materials can be useful according to the present invention.

In particular, the following are non-limiting examples of materials that may be used for their osteoinductive or osteoconductive ability according to the present invention: demineralized bone matrix (DBM), bone morphogenetic proteins (BMPs), transforming growth factors (TGFs), fibroblast growth factors (FGFs), insulin-like growth factors (IGFs), platelet-derived growth factors (PDGFs), epidermal growth factors (EGFs), vascular endothelial growth factors (VEGFs), peptides, anorganic bone mineral (ABM), vascular permeability factors (VPFs), cell adhesion molecules (CAMs), calcium aluminate, hydroxyapatite, coralline hydroxyapatite, alumina, zirconia, aluminum silicates, calcium phosphate, tricalcium phosphate, brushite (dicalcium phosphate dihydrate), tetracalcium phosphate, octacalciumphosphate, calcium sulfate, polypropylene fumarate, pyrolytic carbon, bioactive glass, porous titanium, porous nickel-titanium alloy, porous tantalum, sintered cobalt-chrome beads, ceramics, collagen, autologous bone, allogenic bone, xenogenic bone, coralline, and derivates or combinations thereof, or other biologically produced composite materials containing calcium or hydroxyapatite structural elements. The foregoing may be used as the bone regenerative material or as an additive in a specific bone regenerative material composition.

In specific embodiments, the bone regenerative material used in the present invention particularly can be a material comprising calcium sulfate and may comprise additional ingredients as desired. The calcium sulfate specifically can be α-calcium sulfate hemihydrate, β-calcium sulfate hemihydrate, calcium sulfate dihydrate, or mixtures thereof. In some embodiments, particularly where calcium sulfate is combined with further materials, the calcium sulfate composition may be provided as an aqueous solution or slurry, which can include water and, optionally, one or more additives selected from the group consisting of inorganic salts and surface active agents such as sodium chloride, potassium chloride, sodium sulfate, potassium sulfate, EDTA, ammonium sulfate, ammonium acetate, and sodium acetate. The calcium sulfate further may include additional ingredients, including any of the osteoinductive and osteoconductive materials described herein, as well as accelerants useful to accelerate the reaction of calcium sulfate hemihydrate to calcium sulfate dihydrate, plasticizers, or biologically active agents.

In some embodiments, the bone regenerative material specifically may include calcium phosphate. Particularly, the material may comprise calcium sulfate and calcium phosphate. The calcium phosphate may be in the form of a bioceramic material described has having a specific geometry or shape, such as pellets, granules, wedges, blocks, or disks of various sizes. Non-limiting examples of calcium phosphate that may be used according to the invention include hydroxyapatite, tricalcium phosphate (e.g., α-tricalcium phosphate, β-tricalcium phosphate), tetracalcium phosphate, anhydrous dicalcium phosphate, monocalcium phosphate monohydrate, dicalcium phosphate dihydrate, heptacalcium phosphate, octocalcium phosphate, calcium pyrophosphate, oxyapatite, calcium metaphosphate, carbonatoapatite, dahlite, and combinations or mixtures thereof. In specific embodiments, the calcium phosphate is α-tricalcium phosphate, β-tricalcium phosphate, or a mixture thereof. In some embodiments, it can be useful for the calcium phosphate to be present in two or more forms that can lead to formation of brushite, such as tricalcium phosphate and calcium phosphate monohydrate.

In certain preferred embodiments, the bone regenerative material used in the present invention may comprise calcium sulfate, calcium phosphate, and a particulate material, such as tricalcium phosphate granules or a further particularized osteoinductive or osteoconductive material, such as demineralized bone matrix (DBM). Specific examples of materials that can be particularly useful according to the invention are the materials commercially available under the trade names PRO-DENSE® and PRO-STIM® (Wright Medical Technology, Inc., Arlington, Tenn.). Although such materials are particularly useful for carrying out the invention, other materials that are useful in bone applications may be useful in certain embodiments of the invention. Although not wishing to be bound by theory, it is believed that materials exhibiting bone regenerative properties can provide more advantageous results in various embodiments, particularly materials exhibiting a multi-phasic profile, as otherwise described herein. Examples of further materials that may be useful in certain embodiments of the invention include those known under the names OSTEOSET®, MIIG® X3, CELLPLEX®, ALLOMATRIX®, ALLOMATRIX® RCS, IGNITE®, ACTIFUSE®, CEM-OSTETIC®, GENEX®, PROOSTEON® 500R, BONEPLAST®, CERAMENT®, α-BSM®, CONDUIT® TCP, γ-BSM®, β-BSM®, EQUIVABONE®, CARRIGEN®, MASTERGRAFT®, NOVABONE®, PERIOGLAS®, Chondromimetic, VITOSS®, PLEXUR® Bone Void Filler, BONESOURCE® BVF, HYDROSET®, NORIAN® SRS® Fast Set Putty, NORIAN® CRS® Fast Set Putty, ALLOFUSE®, INTERGRO® DBM Putty, OPTEFORM®, OPTEFIL®, OPTECURE®, ACCELL® 100, ACCELL® CONNEXUS®, ACCELL® EVO3®, OPTIUM DBM®, PROGENIX® DBM Putty, OSTEOFIL® DBM, DBX®, GRAFTON®, GRAFTON PLUS®, PUROS® Demineralized Bone Matrix, INFUSE® Bone Graft, OP-1®, OSTEOCEL®, TRINITY™ Matrix, and TRINITY REVOLUTION™. Various embodiments of bone regenerative materials that may be useful according to the invention are those described in U.S. Pat. No. 6,652,887; U.S. Pat. No. 7,211,266; U.S. Pat. No. 7,250,550; U.S. Pat. No. 7,371,408; U.S. Pat. No. 7,371,409; U.S. Pat. No. 7,371,410; U.S. Pat. No. 7,507,257; U.S. Pat. No. 7,658,768; and U.S. Pat. App. Pub. No. 2007/0059281, the disclosures of which are incorporated by reference herein in their entireties.

In some embodiments, the bone regenerative material may be in the form of a particulate composition that hardens or sets upon mixing with an aqueous solution. Such compositions may include one or more forms of calcium sulfate and one or more forms of calcium phosphate. Preferably, the composition may include at least one form of calcium sulfate and at least two forms of calcium phosphate. Specifically, the composition may include a calcium sulfate hemihydrate (hereinafter "CSH") powder and a brushite-forming calcium phosphate mixture comprising monocalcium phosphate monohydrate (hereinafter "MCPM") powder and a β-tricalcium phosphate (hereinafter "β-TCP") powder.

Such particulate composition can be useful for forming a bone regenerative material comprising calcium sulfate dihydrate (hereinafter "CSD"), which is the product of the reaction between CSH and water. The CSD component can confer good mechanical strength to the bone regenerative material, stimulate bone growth, and provides a relatively fast resorption rate in vivo, such that a porous structure in the bone regenerative material is quickly created upon implantation. Thus, the CSD component can be rapidly replaced with bone tissue in-growth into the implant site.

The two calcium phosphate components can react to form brushite upon mixing with an aqueous solution. The presence of the brushite in the bone regenerative material can slow the resorption rate of the bone regenerative material as compared to a composition comprising CSD only. Thus, the use of such a biphasic bone regenerative material can provide a dual resorption rate defined by the CSD component and the brushite component.

In addition to a slower resorption rate, the use of such a particulate composition as a bone regenerative material in the present invention can provide high mechanical strength, good handling characteristics, and a reasonable setting time. Additionally, such bone regenerative material is particularly useful for producing high quality bone when used according to the invention.

In some embodiments, the CSH powder can have a bimodal particle distribution—i.e., a particle distribution characterized by two peaks in a plot of particle size vs. the volume percentage of particles of each size, although other particle distributions are contemplated by the invention. For example, the bimodal particle distribution of the CSH powder can be characterized by about 30 to about 60 volume percent of particles having a mode of about 1.0 to about 3.0 microns and about 40 to about 70 volume percent of particles having a mode of about 20 to about 30 microns, based on the total volume of the CSH powder. In yet another embodiment, the bimodal particle distribution comprises about 40 to about 60 volume percent of particles having a mode of about 1.0 to about 2.0 microns and about 40 to about 60 volume percent of particles having a mode of about 20 to about 25 microns. The median particle size of the CSH powder is preferably about 5 to about 20 microns, more preferably about 8 to about 15 microns, and most preferably about 10 to about 15 microns.

A particulate composition useful in a bone regenerative material useful according to the invention preferably comprises a CSH powder in an amount of at least 50 weight percent based on the total weight of the particulate composition. In further embodiments, a bone regenerative material useful according to the invention may comprises a CSH powder in an amount of at least 60 weight percent, at least 65 weight percent, at least 70 weight percent, at least 75 weight percent, at least 80 weight percent, at least 85 weight percent, or at least 90 weight percent. In other embodiments, the CSH powder can be present in an amount of about 50 weight percent to about 99 weight percent, about 60 weight percent to about 98 weight percent, about 65 weight percent to about 95 weight percent, about 70 weight percent to about 95 weight percent, or about 70 weight percent to about 90 weight percent.

The CSH is preferably α-calcium sulfate hemihydrate, which exhibits higher mechanical strength as compared to the beta form upon setting to form CSD. The presence of CSD in the bone regenerative material used in the invention can contribute to rapid generation of bone material. The CSH powder can be made by the process disclosed in U.S. Pat. No. 2,616,789, which is incorporated entirely herein by reference in its entirety. The CSH powder may include further components, such as an accelerant capable of accelerating the conversion of CSH to the dihydrate form, thereby causing the bone regenerative material made therefrom to set more quickly. Exemplary accelerants include calcium sulfate dihydrate crystals (available from U.S. Gypsum), particularly CSD coated with sucrose (available from VWR Scientific Products). A process of stabilizing the dihydrate crystals by coating with sucrose is described in U.S. Pat. No. 3,573,947, which is hereby incorporated by reference in its entirety. Other non-limiting examples of accelerants that could be used include alkali metal sulfates and sulfides (e.g., potassium sulfate, sodium sulfate, and calcium sulfide—including hydrates thereof). The accelerant may be present in an amount of up to 1.0 weight percent, based on the total weight of the particulate composition. In some embodiments, the particulate composition includes about 0.001 to about 0.5 weight percent of the accelerant, more typically about 0.01 to about 0.3 weight percent. Mixtures of two or more accelerants can be used.

The calcium phosphate portion of the particulate composition useful in a bone regenerative material according to the invention can comprise a MCPM powder ($Ca(H_2PO_4)_2H_2O$) and a β-TCP powder ($Ca_3(PO_4)_2$). As understood in the art, the main reaction product of MCPM, β-TCP, and water is brushite, otherwise known as dicalcium phosphate dihydrate ($CaHPO_4.2H_2O$) (DCPD). The brushite-forming powders may also participate in other reactions that would result in the formation of certain calcium phosphates with a greater thermodynamic stability than DCPD, such as hydroxyapatite, octacalcium phosphate, and the like. A certain amount of the β-TCP powder may also remain unreacted. The β-TCP powder can have a median particle size of less than about 20 microns. Typically the β-TCP powder will have a median particle size of about 10 microns to about 20 microns. The β-TCP powder portion of the particulate composition can have a bimodal particle size distribution characterized by about 30 to about 70 volume percent of particles having a mode of about 2.0 to about 6.0 microns and about 30 to about 70 volume percent of particles having a mode of about 40 to about 70 microns based on the total volume of the β-tricalcium phosphate powder. In one embodiment, the β-TCP powder has a bimodal particle size distribution characterized by about 50 to about 65 volume percent of particles having a mode of about 4.0 to about 5.5 microns and about 35 to about 50 volume percent of particles having a mode of about 60 to about 70 microns based on the total volume of the β-tricalcium phosphate powder.

Reference to MCPM is intended to encompass monocalcium phosphate (MCP), which is simply the anhydrous form of MCPM that releases the same number of calcium and phosphoric acid ions in solution. However, if MCP is used in place of MCPM, the amount of water used to form the bone regenerative material may need to be increased to account for the water molecule missing from MCP (if it is desired to produce precisely the same dissolution product as formed when using MCPM).

The presence of the brushite component can slow the in vivo resorption of the bone regenerative material as compared to a calcium sulfate. In turn, the slower resorption rate may enable the bone regenerative material to provide structural support for longer periods of time.

A bone regenerative material as described above can be particularly useful according to the invention as it can become a highly porous matrix of calcium phosphate material after being administered in vivo due to the relatively quick resorption of the calcium sulfate component of the mixture. The remaining porous matrix of calcium phosphate provides excellent scaffolding for bone in-growth during the natural healing process.

The amount of MCPM powder and β-TCP powder present in the particulate composition can vary and depends primarily on the amount of brushite desired in the bone graft substitute cement. The brushite-forming calcium phosphate composition (i.e., the combined amount of MCPM and β-TCP powders) can be present at a concentration of about 3 to about 30 weight percent based on the total weight of the particulate composition. In further embodiments, the brushite-forming calcium phosphate composition can be present at a concentration of about 5 to about 25 weight percent, about 10 to about 20 weight percent, about 12 to about 18 weight percent, or about 15 weight percent. The relative amounts of MCPM and β-TCP can be selected based on their equimolar, stoichiometric relationship in the brushite-forming reaction. In one embodiment, the MCPM powder can be present at a concentration of about 3 to about 7 weight percent, based on the total weight of the particulate composition, and the β-TCP can be present in an amount of about 3.72 to about 8.67 weight percent.

The particulate composition also may include a granule, particle, or powder content as otherwise described herein. In specific embodiments, the composition may include a plurality of β-TCP granules having a median particle size greater than the median particle size of the β-TCP powder. The β-TCP granules typically have a median particle size of about 75 to about 1,000 microns, about 100 to about 400 microns, or about 180 to about 240 microns. The granules serve to further reduce the resorption rate of the bone graft substitute cement and contribute to scaffold formation. The β-TCP granules can be present at a concentration of up to 20 weight percent, based on the total weight of the particulate composition. In other embodiments, the β-TCP granules can be present at a concentration of up to 15 weight percent or up to 12 weight percent based on the total weight of the composition. The granules particularly are useful to provide a third phase (as more fully described herein in relation to tri-phasic materials) that exhibits slower resorption than the remaining materials used in the bone regenerative composition (e.g., in comparison to the calcium sulfate phase and the brushite phase describe above).

The aqueous component that is mixed with the particulate composition to form a bone regenerative material useful according to the invention can be selected in order to provide the composition with a desired consistency and hardening or setting time. Typically, the aqueous solution is provided in an amount necessary to achieve a liquid to powder mass ratio (L/P) of at least 0.2, at least 0.21, or at least 0.23. A preferred L/P ratio range is about 0.2 to about 0.3 or about 0.2 to about 0.25. Examples of suitable aqueous components include water (e.g., sterile water) and solutions thereof.

Optionally, a bone regenerative material according to the invention may include one or more additives selected from the group consisting of sodium chloride, potassium chloride, sodium sulfate, potassium sulfate, EDTA, ammonium sulfate, ammonium acetate, and sodium acetate. In one preferred embodiment, the aqueous mixing solution used is a saline solution or a phosphate buffered saline solution. An exemplary aqueous solution is 0.9% NaCl saline solution available from Baxter International (Deerfield, Ill.) and others. The aqueous solution may include one or more organic or inorganic carboxylic acid-containing compounds (hereinafter carboxylic acids or carboxylic acid compounds) which may or may not contain a hydroxyl group on the alpha carbon, optionally titrated to a neutral pH using a suitable base (e.g., neutralized to a pH of about 6.5 to about 7.5 using an alkali metal base such as sodium hydroxide or potassium hydroxide), which can alter water demand, flowability, and/or viscosity of the bone regenerative material upon mixing. Exemplary carboxylic acids include glycolic acid and lactic acid. Preferred carboxylic acids have a single carboxylic acid group, 1 to 10 total carbon atoms (e.g., 1, 2, 3, 4, 5, 6, 7, 8, 9, or 10 carbon atoms including the carbonyl carbon), and 0-5 hydroxyl groups (e.g., 0, 1, 2, 3, 4, or 5) attached to the carbon chain. In one embodiment, the mixing solution is a 0.6M solution of glycolic acid neutralized to a pH of 7.0 using NaOH. Reference to the carboxylic acid compound herein encompasses both the free acid and salt forms. The carboxylic acid may be neutralized to a pH of about 6.5 to about 7.5 in solution using, for example, an alkali metal base, and then isolated as a crystalline powder by evaporation of the solvent (e.g., water). The crystalline powder is typically isolated in a salt form, such as an alkali metal salt form (e.g., lithium, sodium, or potassium salts). Exemplary dry crystalline powders of a carboxylic acid, in salt form, include sodium glycolate, potassium glycolate, sodium lactate, and potassium lactate. The powdered carboxylic acid salt can be added to any of the other powder ingredients that together form the particulate portion of the bone regenerative material, such as the CSH component or either of the calcium phosphate components. However, in certain embodiments, the powdered carboxylic acid is stored in a separate container so that it can be reconstituted with the aqueous solution prior to mixing the solution with the remaining particulate components of the composition.

A bone regenerative material useful according to the invention may include one or more additives that may be selected from any of the individual materials described herein. The additives can be in a powder, liquid, or solid form and can be mixed or encapsulated by the bone regenerative material. Exemplary additives suitable for use in the invention include accelerants (such as sucrose-coated calcium sulfate dihydrate particles), cancellous bone chips, salts (e.g., chloride, potassium chloride, sodium sulfate, potassium sulfate, EDTA, ammonium sulfate, ammonium acetate, and sodium acetate), plasticizers that may alter the consistency and setting time of the composition (e.g., glycerol and other polyols, vinyl alcohol, stearic acid, hyaluronic acid, cellulose derivatives and mixtures thereof, including alkyl celluloses, such as methylhydroxypropylcellulose, methylcellulose, ethylcellulose, hydroxyethylcellulose, hydroxypropylcellulose, hydroxypropylmethylcellulose, carboxymethylcellulose, cellulose acetate butyrate, and mixtures or salts thereof), and any "biologically active agent" (i.e., any agent, drug, compound, composition of matter or mixture that provides some pharmacologic affect that can be demonstrated in vivo or in vitro), particularly any agent recognized as being an anti-osteopenic or anti-osteoporotic agent. Specific pharmacologic agents can include medicaments to treat osteoporosis, such as bisphosphonates, RANKL inhibitors, proton pump inhibitors, hormone therapies, and SERMs, teriparatide, and rPTH. Further examples of biologically active agents include, but are not limited to, peptides, proteins, enzymes, small molecule drugs, dyes, lipids, nucleosides, oligonucleotides, polynucleotides, nucleic acids, cells, viruses, liposomes, microparticles, and micelles. It includes agents that produce a localized or systemic effect in a patient. Further examples of biologically active agents include antibiotics, chemotherapeutic agents, pesticides (e.g., antifungal agents and antiparasitic agents), antivirals, anti-inflammatory agents, and analgesics. Exemplary antibiotics include ciprofloxacin, tetracycline, oxytetracycline, chlorotetracycline, cephalosporins, aminoglycocides (e.g., tobramycin, kanamycin, neomycin, erithromycin, vancomycin, gentamycin, and streptomycin), bacitracin, rifampicin, N-dimethylrifampicin, chloromycetin, and derivatives thereof. Exemplary chemotherapeutic agents include cis-platinum, 5-fluorouracil (5-FU), taxol and/or taxotere, ifosfamide, methotrexate, and doxorubicin hydrochloride. Exemplary analgesics include lidocaine hydrochloride, bipivacaine and non-steroidal anti-inflammatory drugs such as ketorolac tromethamine. Exemplary antivirals include gangcyclovir, zidovudine, amantidine, vidarabine, ribaravin, trifluridine, acyclovir, dideoxyuridine, antibodies to viral components or gene products, cytokines, and interleukins. An exemplary antiparasitic agent is pentamidine. Exemplary anti-inflammatory agents include .alpha.-1-anti-trypsin and .alpha.-1-antichymotrypsin. Useful antifungal agents include diflucan, ketaconizole, nystatin, griseofulvin, mycostatin, miconazole and its derivatives as described in U.S. Pat. No. 3,717,655, the entire teachings of which are incorporated herein by reference; bisdiguanides such as chlorhexidine; and more particularly quaternary ammonium compounds such as domiphen bromide, domiphen chloride, domiphen fluoride, benzalkonium chloride, cetyl pyridinium chloride, dequalinium chloride, the cis isomer of 1-(3-chlorallyl)-3,5,7-triaza-1-azoniaadamantane chloride (available commercially from the Dow Chemical Company under the trademark Dowicil 200) and its analogues as described in U.S. Pat. No. 3,228,828, the entire teachings of which are incorporated herein by reference, cetyl trimethyl ammonium bromide as well as benzethonium chloride and methylbenzethonium chloride such as described in U.S. Pat. Nos. 2,170,111; 2,115,250; and 2,229,024, the entire teachings of which are incorporated herein by reference; the carbanilides and salicylanilides such 3,4,4'-trichlorocarbanilide, and 3,4,5-tribromosalicylanilide; the hydroxydiphenyls such as dichlorophene, tetrachlorophene, hexachlorophene, and 2,4,4'-trichloro-2'-hydroxydiphenylether; and organometallic and halogen antiseptics such as sinc pyrithione, silver sulfadiazone, silver uracil, iodine, and the iodophores derived from non-ionic surface active agents such as described in U.S. Pat. Nos. 2,710,277 and 2,977,315, the entire teachings of which are incorporated herein by reference, and from polyvinylpyrrolidone such as described in U.S. Pat. Nos. 2,706,701, 2,826,532 and 2,900,305, the entire teachings of which are incorporated herein by reference. Useful growth factors include any cellular product that modulates the growth or differentiation of other cells, particularly connective tissue progenitor cells. The growth factors that may be used in accordance with the present invention include, but are not limited to, fibroblast growth factors (e.g., FGF-1, FGF-2, FGF-4); platelet-derived growth factor (PDGF) including PDGF-AB, PDGF-BB and PDGF-AA; bone morphogenic proteins (BMPs) such as any of BMP-1 to BMP-18; osteogenic proteins (e.g., OP-1, OP-2, or OP-3); transforming growth factor-.alpha., transforming growth factor-β (e.g., β1, β2, or β3); LIM mineralization proteins (LMPs); osteoid-inducing factor (OIF); angiogenin(s); endothelins; growth differentiation factors (GDF's); ADMP-1; endothelins; hepatocyte growth factor and keratinocyte growth factor; osteogenin (bone morphogenetic protein-3); heparin-binding growth factors (HBGFs) such as HBGF-1 and HBGF-2; the hedgehog family of proteins including indian, sonic, and desert hedgehog; interleukins (IL) including IL-1 thru -6; colony-stimulating factors (CSF) including CSF-1, G-CSF, and GM-CSF; epithelial growth factors (EGFs); and insulin-like growth factors (e.g., IGF-I and -II); demineralized bone matrix (DBM); cytokines; osteopontin; and osteonectin, including any isoforms of the above proteins. The biologically active agent may also be an antibody. Suitable antibodies, include by way of example, STRO-1, SH-2, SH-3, SH-4, SB-10, SB-20, and antibodies to alkaline phosphatase. Such antibodies are described in Haynesworth et al., Bone (1992), 13:69-80; Bruder, S. et al., Trans Ortho Res Soc (1996), 21:574; Haynesworth, S. E., et al., Bone (1992), 13:69-80; Stewart, K., et al, J Bone Miner Res (1996), 11(Suppl.):S142; Flemming J E, et al., in "Embryonic Human Skin. Developmental Dynamics," 212:119-132, (1998); and Bruder S P, et al., Bone (1997), 21(3): 225-235, the entire teachings of which are incorporated herein by reference. Other examples of biologically active agents include bone marrow aspirate, platelet concentrate, blood, allograft bone, cancellous bone chips, synthetically derived or naturally derived chips of minerals such as calcium phosphate or calcium carbonate, mesenchymal stem cells, and chunks, shards, and/or pellets of calcium sulfate. Additives, particularly pharmacological additives, more particularly anti-osteoporotic additives, can be present in a solid form that is mixed into the bone regenerative material or placed into the bone void and encapsulated by the bone regenerative material. The pharmacologic therapies can be eluting, dissolving, disintegrating, or evaporating from the bone regenerative material.

A bone regenerative material useful in the methods of the present invention can be formed by a variety of methods depending upon the exact nature of the composition. In some embodiments, the bone regenerative material may be in a particulate form that could be packed into a formed void in a bone. In other embodiments, the bone regenerative material can be an injectable, flowable form that may be prepared by mixing a particulate composition, such as described above, with an aqueous solution as described herein using manual or mechanical mixing techniques and apparatus known in the art. Specifically, the components can be mixed at atmospheric pressure or below (e.g., under vacuum) and at a temperature that will not result in freezing of the aqueous component of the mixture or significant evaporation. Following mixing, the homogenous composition typically has an injectable, paste-like consistency, although the viscosity and flowability of the mixture can vary depending on the additives therein. The bone regenerative material can be transferred to a delivery device, such as a syringe, and injected into the created void. In some embodiments, the material can be injected through an 11 to 16-gauge needle up to, for example, 10 cm long.

In certain embodiments, the nature of the bone regenerative material may be characterized in relation to injection force ranges in which the material can be injected. In various embodiments, the material may have an injection force of up to 1,200 N, up to 1,000 N, up to 800 N, up to 600 N, up to 500 N, or up to 400 N. In other embodiments, injection force ranges may be about 1 N to about 1,200 N, about 2 N to about 1,000 N, about 3 N to about 800 N, about 4 N to about 700 N, about 5 N to about 660 N, about 10 N to about 660 N, or about 10 N to about 330 N.

In specific embodiments, a bone regenerative material useful according to the invention can be one that will generally set, as defined by the Vicat needle drop test set forth below, in about 3 to about 25 minutes, more preferably about 10 to about 20 minutes. The bone regenerative material preferably will reach a hardness comparable to or greater than bone within about 30 to about 60 minutes. Setting of the material can occur in a variety of environments, including air, water, in vivo, and under any number of in vitro conditions.

A hardened bone regenerative material useful according to the invention preferably exhibits complex dissolution with a self-forming porous scaffold and certain mechanical strength properties, particularly as characterized by diametral tensile strength and compressive strength. For example, the material may exhibit a diametral tensile strength of at least 4 MPa after curing for one hour in ambient air following preparation of the material to be a state for delivery, more preferably a diametral tensile strength of at least 5 MPa, most preferably at least 6 MPa. Further, the bone regenerative material may exhibit a diametral tensile strength of at least 8 MPa after curing for 24 hours in ambient air following preparation of the material for delivery, more preferably a diametral tensile strength of at least 9 MPa after curing for 24 hours, and most preferably at least 10 MPa.

A bone regenerative material useful in the present invention also exhibits a high level of compressive strength, such as a compressive strength of at least 15 MPa after curing for one hour in ambient air following preparation of the material for delivery, more preferably a compressive strength of at least 40 MPa. Further, preferred embodiments of the bone regenerative material may exhibit a compressive strength of at least 50 MPa after curing for 24 hours in ambient air following preparation of the material for delivery, more preferably a compressive strength of at least 80 MPa.

In certain embodiments, the strength of the hardened bone regenerative material may be increased though addition of various materials. Although the invention encompasses any material recognized in the art for increasing one or both of tensile strength and compressive strength, particular useful can be embodiments that incorporate one or more fibrous materials. Thus, the invention specifically encompasses fiber composites of the bone regenerative material.

The fiber composites useful in the invention particularly can include biodegradable polymer fibers. Such fibers not only can provide for increased strength properties for the bone regenerative material but also can provide for sustained delivery of one or more of the biologically active agents disclosed above (e.g., growth factors, antibiotics, etc.) since the active agent may be mixed with the polymer prior to fiber formation, and the active agent will be slowly released in vivo as the fibers biodegrade. In further embodiments, non-biodegradable fibers also may be used, although it is preferable for any non-biodegradable fibers to be inert in nature. Non-limiting examples of materials that have been shown to be useful as fibers for increasing the strength of a bone regenerative material include poly(L-lactic acid) (PLLA), polyethylene terephthalate (PET) (e.g., MERSILENE® sutures), polyethylene, polyester (e.g., FIBERWIRE®), poliglecaprone (e.g., MONOCRYL®), polyglycolic acid, and polypropylene. Of course, one of skill in the art with the benefit of the present disclosure would be able to recognize even further material that could be provided in fiber form or otherwise to increase the strength of the bone regenerative material used according to the present invention.

Fibers used for increasing the strength of the bone regenerative material may have various sizes. Preferably, fibers used in various embodiments can have an average diameter of about 1 μm to about 100 μm, about 2 μm to about 75 μm, about 3 μm to about 50 μm, about 4 μm to about 40 μm, or about 5 μm to about 25 μm. Such fibers further preferably have an average length of about 100 μm to about 1,000 μm, about 150 μm to about 900 μm, about 200 μm to about 800 μm, or about 250 μm to about 750 μm.

Fibers used for increasing the strength of the bone regenerative material also may be included in varying concentrations. Specifically, the fibers may comprise about 0.1% to about 10%, about 0.25% to about 9%, about 0.5% to about 8%, about 0.75% to about 7%, about 1% to about 6%, or about 1.5% to about 5% by weight of the bone regenerative material.

Preferably, the fibers are added in a concentration so as to appreciably increase the strength of the bone regenerative material as compared to the material without any fiber additive. Specifically, the fibers may be added in an amount to increase the tensile strength of the bone regenerative material by at least 5%, at least 10%, at least 15%, at least 20%, or at least 25%. Similarly, addition of the fiber component may increase compressive strength by at least 10%, at least 15%, at least 20%, at least 25%, or at least 30%.

In some embodiments, addition of the fiber component may cause the bone regenerative material to increase in viscosity, which may reduce injectability of the material. To overcome this increase in viscosity, it may be useful to inject the material using a syringe with a tapered nozzle. Such nozzle configuration can lower the force needed to inject the more viscous paste through a needle.

In preparation, the fibers may be added to a dry mixture of the materials used in the bone regenerative material. The combined materials may be wetted to form a paste. It further can be useful to include additional processing steps to improve mixing of the fibers into the bone regenerative material and to reduce the presence of fused fiber groups. For example, the cut fibers may undergo ultrasonic agitation for a defined time (e.g., 30-60 minutes), and such agitation may be carried out with the fibers in a liquid medium in which the fiber polymer is insoluble (e.g., isopropyl alcohol). The sonicated fibers can then be added to the dry ingredients used for the bone regenerative material and blended (e.g., by stirring). The combination is then filtered and dried under vacuum. The combined materials may then be wetted for forming the paste material for use.

The methods of the present invention generally comprise replacing a defined volume of degenerated bone material (optionally in an area having a defined shape) with a bone regenerative material that causes generation of new bone material of greater density (or other bone quality measure as described herein) than the replaced, degenerated bone material. The term "degenerative bone material" or "degenerated bone material" can mean bone material that is clinically categorized as osteopenic or osteoporotic. The terms more specifically can mean bone having a T-score of less than −1, less than −1.5, less than −2, less than −2.5, or less than −3. Such degenerated bone material typically will exist within a bone that generally also is categorized as osteopenic or osteoporotic.

The inventive methods generally can be described as methods for improving bone quality of a localized area of a bone. Specifically, bone quality can correspond directly to BMD but also may refer to the general strength of the bone (including compressive strength) and the ability of the bone to resist fracture in and around the localized area of the bone. This ability to improve bone quality in part arises from the recognition that the localized areas of the bone can in effect be reset to a healthier bone quality—that of normal bone or the bone quality of a similar patient under conditions where BMD is recognized to be at its peak. Surprisingly, it has been found that degenerative bone material in a localized area of a bone, such as from a patient suffering from osteoporosis, can be replaced by using a bone regenerative material that causes generation of new bone material in the localized area. What is particularly surprising is that the newly generated bone material is not of osteoporotic quality. This is unexpected because one would expect that when a patient suffers systemically from osteoporosis, any new bone material formed in such patient would be of reduced quality (i.e., would be osteoporotic and exhibit low density). The present invention, however, has shown that after implantation of the bone regenerative material into the osteopenic or osteoporotic bone, the material is resorbing at a predicable rate and is not negatively affected by the systemic disease. Subsequent generation of dense, new bone material at the localized area of the bone improves bone quality and BMD as measured by T-score on DEXA. Specifically, the T-scores indicate the newly generated bone material is substantially similar to normal bone in that it exhibits a density that is at least at a level that would be expected to be seen in patients at their peak BMD (e.g., a T-score in the range of about −1 to about 1) and not in an osteopenic or osteoporotic state. In further embodiments, the newly generated bone material can exhibit a compressive strength that is substantially similar to (or exceeds) the compressive strength of normal bone. Such characteristics may be related to the newly formed bone material, specifically to the localized area of the bone in general (i.e., the newly formed bone material and the existing bone material in the immediately surrounding area).

In certain embodiments, the methods of the invention can comprise active steps for forming a void within a bone in a patient. Specifically, the methods can comprise forming a void in a localized area of a bone. Any methods useful for forming such void can be used according to the invention. In some embodiments, the methods can comprise chemically dissolving or otherwise eliminating bone material within a defined area of the bone to form a void. In other embodiments, liquid lavage may be used create a void within a bone, such as the methods described in U.S. Pat. Pub. No. 2008/0300603, which is incorporated herein by reference. In further embodiments, sonication could be used to clear bone material in a localized area. In other embodiments, a void may be created through use of an inflatable or expandable device (e.g., a balloon or an in situ expandable reamer). Expandable meshes also could be used. In specific embodiments, the methods can comprise any mechanical means for creating a void within a localized area of a bone.

In some embodiments, the methods can comprise drilling or otherwise channeling (e.g., by stabbing with a cannulated or solid needle, probe, or the like) into the interior of the localized area of the bone. In some embodiments, the channel formed in this manner may provide the void desired for a specific method of treatment. In other, preferred embodiments, the drilling or channeling can be characterized as means for forming access to the interior of the localized area of the bone to be treated so that a void of dimensions greater than the channel can be formed. Using the channel to access the area of the bone to be treated, a void of a predetermined shape and size can be formed by any means useful for creating a void, including any of the methods described above. Depending upon the degenerative state of the bone (i.e., the progression of the osteopenia or osteoporosis), formation of a void may include removal of at least a portion of the degenerated bone material.

Figure 2A:
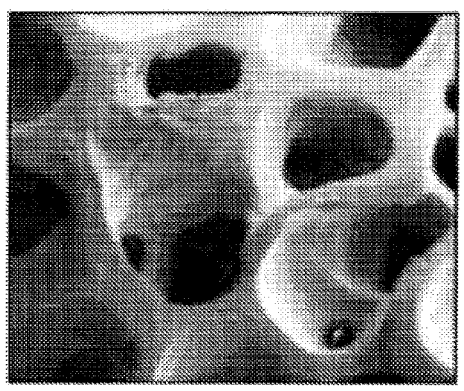
FIG. 2a is a scanning electron micrograph of normal bone.
Figure 2B:
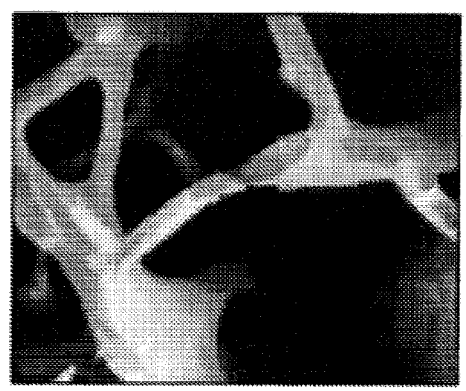
FIG. 2b is a scanning electron micrograph of osteoporotic bone.

FIG. 2a and FIG. 2b show scanning electron micrographs of normal bone and osteoporotic bone, respectively. As seen therein, the normal bone shows a pattern of strong interconnected plates of bone material. Much of this material is lost in osteoporosis, and the remaining bone has a weaker, rod-like structure, some of the rods being completely disconnected. Such disconnected bone may be measured as bone mass but contribute nothing to bone strength. In some embodiments, the void may be formed simply by breaking apart the degenerated bone material, such as by scraping, drilling, or the use of specialized materials for reaming out the bone to form the void. Such clearing may be otherwise described as breaking, crumbling, crushing, pulverizing, reaming, expanding, or otherwise dismantling or pushing or moving aside the bone material within the area for void formation. In some embodiments, this may be referred to as debridement of the bone in the localized area, insufflation, or snaking. Preferably, the area of debridement conforms to the predetermined shape and size of the desired void.

Because of the loss of BMD, the degenerated bone material that is broken apart to form the void may simply be left as remnant material in the formed void. In other embodiments, it may be desirable to remove some or all of the degenerated bone material that is cleared to form the void. Thus, void formation according to the invention may be characterized as breaking apart the degenerated bone material in the localized area and removing at least a portion of the material, or void formation may be characterized simply as the breaking apart step. In some embodiments, the active steps for forming a void in a bone may be referred to as clearing damaged and/or degenerated bone material from the localized area of the bone. Clearing thus can encompass the complete or partial destruction of the degenerated bone material and/or removal of all or part of the degenerated bone material from the void. In specific embodiments, the invention can be characterized as removing damaged and/or degenerated bone material from a localized area of a bone to form a void of predetermined shape and size. In other embodiments, the method can be characterized as forming an amorphous void of defined volume.

The methods further can comprise at least partially filling the formed void with a bone regenerative material, such as described herein. The amount of bone regenerative material used can depend upon the volume of the void formed in the preceding step. In various embodiments, the volume of bone regenerative material used can range from about 1 $cm^3$ to about 200 $cm^3$, about 2 $cm^3$ to about 150 $cm^3$, about 2 $cm^3$ to about 100 $cm^3$, about 2 $cm^3$ to about 75 $cm^3$, about 5 $cm^3$ to about 50 $cm^3$, about 10 $cm^3$ to about 40 $cm^3$, or about 15 $cm^3$ to about 35 $cm^3$. The foregoing volumes thus can be representative of the actual volume of the void formed in the bone, as described above. In specific embodiments, volumes can be specifically related to the bone and the area being treated. For example, in relation to the distal radius, volume may be about 1 $cm^3$ to about 10 $cm^3$, about 1 $cm^3$ to about 8 $cm^3$, or about 1 $cm^3$ to about 5 $cm^3$. In relation to a vertebral body, volume may be about 1 $cm^3$ to about 30 $cm^3$, about 2 $cm^3$ to about 25 $cm^3$, or about 2 $cm^3$ to about 20 $cm^3$.

In relation to the proximal femur, volume may be about 5 cm$^3$ to about 100 cm$^3$, about 5 cm$^3$ to about 80 cm$^3$, or about 10 cm$^3$ to about 50 cm$^3$. In relation to the proximal humerus, volume may be about 5 cm$^3$ to about 200 cm$^3$, about 5 cm$^3$ to about 150 cm$^3$, about 5 cm$^3$ to about 100 cm$^3$, or about 10 cm$^3$ to about 80 cm$^3$.

The shape of the void formed in the bone can vary depending upon the bone being treated. In some embodiments, the shape of the formed void may substantially correspond to the shape of the area in the proximal femur known as Ward's area. In some embodiments, the shape of the void may substantially conform to the shape of the localized area of the bone being treated. For example, in relation to treatment of the distal radius, the void may substantially conform to the shape of the distal 1-5 cm of the bone. In specific embodiments, the shape of the formed void may not be critical to the success of the method; however, the invention is intended to encompass formation of voids of defined shape and size that may be desirable in the specific bone being treated.

In certain embodiments, specifically in treating patients exhibiting particularly advanced stages of bone degeneration, at least some degree of treatment may be achieved without creating a void prior to injection of the bone regenerative material. As discussed previously, the effect of bone loss related to osteoporosis is a reduction in the density of the bone material, or formation of larger, more pronounced spaces within the bone. In advanced osteoporosis, cavitation of the bone make allow for injecting a bone regenerative material directly into a localized area of a bone exhibiting such increased porosity. In specific embodiments, the force of injecting the bone regenerative material itself may artificially enlarge the space within the bone and thus may in effect form a void that is immediately filled. In other embodiments, the injected bone regenerative material may simple permeate the degenerated bone of increased porosity and thus substantially fill pore volume in the localized area of the bone being treated. Accordingly, in certain embodiments, the invention encompasses simultaneously creating and filling a void in a localized area of a bone. Although such embodiments may occur, it is expected that most effective results are achieved by at least forming a channel into the area of the degenerated bone to be filled with the bone regenerative material. More preferably, a void will be formed as otherwise described above.

Any means useful for inserting the bone regenerative material into the formed void may be used. For example, when the bone regenerative material is in a flowable form, the material may be injected into the formed void, such as by using a syringe. Thus, in particular embodiments, it can be useful for the bone regenerative material to be introduced into the void in a substantially flowable state and then harden in vivo. In other embodiments, it may be useful to substantially harden the bone regenerative material outside the body and then pack the hardened material into the void. Still further, the bone regenerative material may take on further physical conditions, such as a putty-like consistency. In some embodiments, the bone regenerative material may be in a particulate form of varying sizes that can be packed into the void. Moreover, the bone regenerative material may be filled into the void in addition to one or more additional materials that can assist in filling the void and may provide one or more further beneficial functions, such as providing temporary or permanent support to the localized area. In specific embodiments, an eluting substrate, such as BMP or a peptide soaked expanding sponge, could be inserted into the void prior to insertion of the bone regenerative material.

In some embodiments, the bone regenerative material may be inserted into the created void in connection with an additional reinforcing agent (e.g., a screw or other cylindrical body or a hollow-core material—e.g., coating the reinforcing agent or included within a hollow core of the reinforcing agent). Beneficially, however, the methods of the present invention allow for filling of the formed void without the need for any further reinforcing agent (whether the reinforcing agent is resorbable or non-resorbable). In specific embodiments, the bone regenerative material used in the invention can be a material that hardens to immediately provide the localized area of the treated bone with sufficient strength such that the treated area of the bone has a fracture resistance that is at least equivalent to the fracture resistance of the bone prior to treatment. Such advantage is more particularly described in the Examples below. As also described herein, the need for reinforcing agents is further negated by the substantial increase in bone strength established by the in-growth of new bone material that is substantially identical in characteristics to natural, healthy bone. Such increases in bone qualities begin to be seen relatively soon (e.g., within a time of less than one week up to a time of about 16 weeks).

In some embodiments, the invention particularly can provide a method of treating a patient suffering from a degenerative bone condition. Particularly, the patient may be suffering from and/or diagnosed as having a condition of osteopenia or a condition of osteoporosis. Alternately, the patient may be suffering from any other condition having the effect of causing bone degeneration, particularly a loss of BMD and/or bone strength.

The invention particularly is useful in that the formation of the void clears the localized area of the degenerated bone material so that the bone regenerative material can be provided therein. Preferably, the bone regenerative material promotes formation of new, non-degenerated bone material in the void. Advantageously, the newly formed bone material is natural to the patient. Preferably, the newly formed bone material has a density that is substantially identical to or exceeds that of normal bone. In other words, the newly formed bone material has a density that is substantially identical to the density of bone in a person (preferably of the same race and gender) at an age of about 30-35 years. In particular embodiments, this can mean that the newly formed bone material has a T-score when measured by DEXA that is greater than −1, preferably is at least −0.5 or at least 0. In other embodiments, T-score for the newly formed bone material may be In other embodiment, T-score may be about −1.0 to about 2.0, about −1.0 to about 1.0, about −1.0 to about 0.5, about −1.0 to about 0, about −0.5 to about 2.0, about −0.5 to about 1.5, about −0.5 to about 1.0, about −0.5 to about 0.5, about 0 to about 2.0, about 0 to about 1.5, or about 0 to about 1.0. In other embodiment, the newly formed bone material may have a BMD that sufficiently exceeds the BMD prior to treatment (as indicated by improved T-score) such that the patient is viewed as having a significant relative improvement in BMD. The newly formed bone also can have a compressive strength that is substantially identical to or exceeds that of normal bone.

The inventive methods are particularly beneficial in that the treated, localized area of the bone can effectively be remodeled over time to be substantially identical to normal bone (i.e., exhibiting normal BMD, and/or normal compressive strength, and/or normal resistance to fracture). Moreover, in some embodiments, the effects of the bone regenerative material for generating new, natural bone growth can actually extend outside the bounds of the formed void.

Particularly, it has been found according to the invention that a gradient effect may be provided in that new, natural bone material of improved density may be formed within the originally formed void, but new bone material also can be generated in the area of the bone adjacent the formed void. This is particularly beneficial in that the areas of the bone adjacent the formed void also are strengthened such that the incidence of adjacent fractures is reduced.

As previously noted, the methods of the invention can be practiced in a variety of bones in the mammalian body. In a particularly useful embodiment, the inventive methods may used in a bone in the hip area of a patient. For example, following is an exemplary method for treating a patient suffering from a degenerative bone condition by replacing bone material in a localized area of the patient's femur, specifically the proximal femur. The surgical technique uses a lateral approach similar to a standard core decompression or hip screw. One distinction in the technique is the creation of the geometry of the defect or void to receive the graft (i.e., the bone regenerative material), which will subsequently regenerate dense, new, natural bone to augment the bone quality in the localized area of the bone, strengthen the femoral neck and Ward's Triangle, and decrease risk of insufficiency fracture. The following procedure (varying in geometry) may be utilized in other areas of metaphyseal bone, such as the vertebral body, distal radius, proximal humerus, and tibia.

Figures 3A, 3B, 3C, 3D:
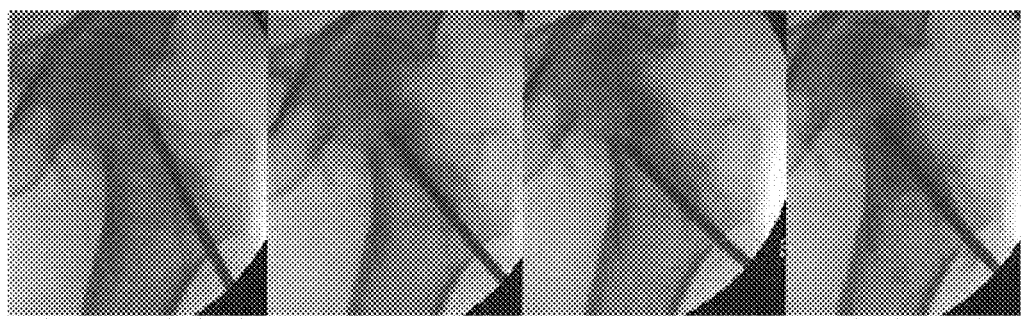
FIGS. 3a-3i are radiographic images showing the injection of a bone regenerative material into a void created in the proximal femur of a patient in a medial to lateral fashion according to one embodiment of the invention.
Figures 3E, 3F, 3G, 3H, 3I:

To carry out the technique, the patient may be positioned on a radiolucent table in the supine position. Radiology support can be provided by C-arm equipment and an x-ray technician to provide x-ray navigation during the procedure. As noted above, the lateral approach to the proximal femur can be used. In other embodiments, a greater trochanter approach also could be used. A small incision can be made just distal to the greater trochanter, and a guidewire can be introduced into the proximal femur under fluoroscopic guidance in anterioposterior (AP) and lateral views. A cannulated 5.3 mm drill can be introduced over the guidewire up to the femoral head, and a channel can be formed up to (and alternately through) the site for void formation. This channel can be referred to as a core. In alternate embodiments, any means for breaking away the weak, osteoporotic bone material may be employed, such as using a countersink drill, or a cortical punch and blunt obdurator to create the space. The drill and guidewire can be removed, and a working cannula can be introduced into the core to form the surgically-created defect, or void. A debridement probe can be used to create space within the localized area of the femur for implantation of the bone regenerative material. Specifically, the probe may have a precisely angled head for accommodating the endosteal anatomy of the femoral neck and Ward's Triangle. Creating this geometry to allow a complete fill of the neck and Ward's Triangle offers the greatest potential for complete regeneration and higher ultimate bone strength. The surgically-created defect (or void) preferably is washed and aspirated before proceeding. The bone regenerative material is prepared if necessary and injected through a long cannula into the surgically-created defect. Injection through the cannula eliminates pressurization as well as a self-venting potential down the medullary canal. After injection of the bone regenerative material, the incision is closed in standard fashion. Beneficially, such procedure can be performed with minimal down-time for the patient and preferably requires no over-night hospitalization (e.g., requiring only up to about 6-8 hours total time in a clinic, hospital, or other medical facility). FIGS. 3a-3i provide radiographic images of injection of the bone regenerative material, PRO-DENSE® (available from Wright Medical, Arlington, Tenn.), into a void that was created in the proximal femur of a patient just prior to injection of the bone regenerative material. As seen in the images, the bone regenerative material is filled into the void through a long cannula, which is initially inserted up to the femoral head (FIG. 3a), maneuvered to completely fill the void (FIG. 3b-FIG. 3h), and removed once back-filling is complete (FIG. 3i).

Multiple variations of the above procedure could be practiced within the scope of the invention. For example, FIG. 4 provides an enhanced radiograph of a proximal femur illustrating the target fill area, any portion of which could be filled, with or without initial debridement of the area. The figure also illustrates the approximate area and size of the initial channel that could be formed from a lateral approach. Specifically, FIG. 4 illustrates the channel extending laterally through the proximal femur to the femoral head, and hatching is provided to illustrate an exemplary area in the proximal femur, any portion of which may be targeted as a candidate for removal of bone material and filling with a bone regenerative material. As further, non-limiting examples, one or more "struts" can be formed in the proximal femur as branches from the initial channel and then filled with a bone regenerative material. Still further, one or more struts could have one or more portions that are significantly enlarged to increase the amount of bone regenerative material that is placed into a defined area of the bone. Yet further, a generalized, larger area of the proximal femur could be debrided and filled. Further, similar embodiments also could be envisioned in light of the present disclosure.

A further surgical technique that may be used according to the present invention is described below in relation to an impending atypical femoral fracture. Such fractures most commonly occur in the proximal one-third of the femoral shaft, but they may occur anywhere along the femoral diaphysis from just distal to the lesser trochanter to proximal to the supracondylar flare to the distal femoral metaphysis. The fracture is atypical in that it usually occurs as a result of no trauma or minimal trauma, equivalent to a fall from a standing height or less. The fracture may be complete, extending across the entire femoral shaft, often with the formation of a medial spike, or incomplete, manifested by a transverse radiolucent line in the lateral cortex.

The following specifically describes a technique for introducing a bone regenerative material into the femoral body of a patient, particularly a patient subject to an impending atypical fracture, e.g., osteopenic or osteoporotic patients, by creating a void in an intact femoral body prior to occurrence of an atypical femoral fracture. The initial step—guide pin placement—includes formation of a skin incision (e.g., 1 cm) proximal to the tip of the greater trochanter. A serrated tissue protector sleeve with cannulated centering guide and guide pin is inserted to the cortex of the greater trochanter. The guide pin is advanced through the cortex of the greater trochanter and is continued to the region of impending fracture in the femoral shaft. The depth and position of the guide pin can be confirmed by fluoroscopy in both planes.

Next, a defect is created and prepared for injection of the bone regenerative material. Specifically, while maintaining the serrated tissue protector in place, the cannulated centering guide is removed, and a 5.3 mm cannulated drill is inserted and advanced through the trochanter. The drill is then removed, leaving the guide pin in place, and a flexible reamer is introduced. The reamer is advanced over the guide wire and through the trochanter, and the guide pin is then removed. The reamer is then advanced to the region of impending fracture and removed. The working cannula with insertion trocar is inserted through the serrated tissue protector and seated inside the cortex (i.e., provided with a "snug" fit). The serrated tissue protector and insertion trocar are then removed. The injection cannula can be placed through the working cannula and advanced to the region of the femoral fracture, and the cannula can be used with suction to remove any created particulates in the femur. The bone regenerative material is then injected, preferably while monitoring (e.g., by fluoroscopy). The working time for injection typically is approximately 2-4 minutes for optimal fill results. The injection cannula and the working cannula can then be removed. The soft tissue then can be irrigated, and the skin is closed with appropriate means (e.g., sutures).

Another description of a surgical technique that may be used according to the present invention is described below in relation to the distal radius. The following specifically describes a technique for introducing a bone regenerative material into the distal radius of osteopenic or osteoporotic patients by creating a void in an intact distal radius prior to any fragility fracture. To carry out the technique, the patient may be positioned with the arm on a radiolucent table with the palm of the hand facing upward. Radiology support can be provided by C-arm equipment and an x-ray technician to provide x-ray navigation during the procedure. To form an injection portal, a 1 cm incision is made centered over the radial styloid, and the subcutaneous tissue is bluntly dissected down to the periosteum between the first and second dorsal extensor compartments. A k-wire is inserted under fluoroscopic guidance 3-4 mm proximal to the radioscaphoid joint line and centered (dorsal to volar) in the radial styloid. A cannulated drill is used to drill into the metaphysis of the distal radius. A debridement probe can be used to create space within the localized area of the distal radius for implantation of the bone regenerative material. Specifically, the probe may have a precisely angled head for accommodating the endosteal anatomy of the distal radius. The surgically-created defect preferably is washed and aspirated before proceeding. The bone regenerative material is prepared if necessary and injected through a cannula into the surgically-created defect. After injection of the bone regenerative material, the incision is closed in standard fashion. Such surgical technique would not be expected to require hospitalization of the patient, which allows for a beneficial treatment for bone degeneration with minimal down-time for the patient. FIGS. 5a-5c provide illustrations of specific steps in the above-described surgical technique. FIG. 5a shows formation of access to the distal radius metaphysis. FIG. 5b shows the mechanically formed void in the distal radius. FIG. 5c shows the localized area of the radius after filling of the void with a bone regenerative material.

Another description of a surgical technique that may be used according to the present invention is described below in relation to the vertebrae. The following technique utilizes an inflatable tamp (or balloon tamp) such as those available from Kyphon, Inc. (now a subsidiary of Medtronic, Inc.). Thus, as further described herein, some methods according to the present invention may be improvements on a kyphoplasty technique. In other embodiments, however, techniques for replacing degenerative bone in vertebrae may be substantially similar in nature to the techniques described above in relation to the proximal femur and the distal radius. A substantial distinction over known techniques for treating vertebral fractures is that the methods of the present invention would be carried out on a vertebra before the vertebra was affected by an osteoporotic compression fracture (or any other type of fracture).

In the exemplary surgical technique for replacing degenerative bone in a vertebra, the patient may be positioned on a radiolucent table in the prone position. Radiology support can be provided by C-arm equipment and an x-ray technician to provide x-ray navigation during the procedure. After confining the vertebra and its corresponding pedicles to be treated with the radiological tube in an antero-posterior projection, a small cutaneous incision (approximately 1 cm) can be made in the dorsal or lumbar area into which a bone biopsy need of 11/13 gauge is introduced through the posterior portion of the pedicles, sloping anteriorly, medially, and caudally. The approach in this exemplary method is bilateral. Once the exact position of the needle is verified, a Kirshner wire is introduced. A drill tip is advanced into the wall a few millimeters from the anterior cortex margin to form an intravertebral bone channel for successive passage of the balloon tamp.

Successively, under fluoroscopic guidance in a lateral projection, the probe is carefully pushed forward and placed in the anterior two-thirds of the vertebra. It can have a range of length comprised between 15 and 20 mm, with a maximum volume respectively of 4 and 6 mL. Once the exact position of the balloons in the two hemivertebrae is verified with the aid of two radiopaque markers located at the extremities (proximal and distal), the balloons are distended with a liquid containing 60% contrast medium, achieving a lifting of the superior vertebral end-plates and creating a cavity internally through compression of the surrounding cancellous bone. The inflation stops when the space is created, there is contact with the cortical somatic surface, or when the maximum pressure (220 PSI) or dilation of the balloon is achieved. The surgically created void can then be washed and aspirated.

The bone regenerative material can be prepared as necessary. The bone regenerative material then is loaded into dedicated cannulas and moved forward through the working cannula until correspondence with the anterior third of the void. Immediately after, the bone regenerative material is pushed with slight pressure using a plunger stylet under continuous fluoroscopic guidance. The filling volume is usually 1-2 mL greater than that which is obtained with the balloon, which allows the bone regenerative material to distribute itself effectively. To complete the procedure, all cannulas are extracted, the cutaneous incisions are sutured, and the patient may be instructed to remain in bed for the next few hours. The length of the procedure for each vertebra treated typically is around 35-45 minutes. A traditional radiographic inspection can be performed after the procedure to evaluate the results obtained. FIGS. 6a-6c illustrate specific steps from the exemplary procedure for replacing bone in a vertebra. FIG. 6a shows insertion of a balloon tamp bilaterally in the vertebra being treated. FIG. 6b shows inflation of the balloon to mechanically form a void in the vertebra. FIG. 6c shows removal of the balloons while backfilling the formed void in the vertebra with a bone regenerative material.

Although the inventive methods may be characterized in terms of treating a patient suffering from a degenerative bone condition (such as osteopenia or osteoporosis), the invention further may be characterized in relation to the ability to specifically alter localized areas of bone, such as by improving BMD, improving bone quality, improving bone strength, improving natural bone structure, and the like. The invention also can be characterized in relation to the ability to remodel localized areas of bone, including providing the localized area of the bone with an exceedingly increased density that gradually reduces to normal BMD.

In certain embodiments, the invention can be characterized as providing various methods of improving bone quality at a localized area of a bone. Bone quality can be characterized specifically in relation to BMD, which can be evaluated in relation the T-score from a DEXA scan. Bone quality also may relate more generally to the overall structure of the bone material in relation to the bone scaffolding. Further, bone quality may specifically relate to bone strength—i.e., compressive strength.

The specific mechanical strength of bone, whether it be in relation to natural bone material or bone material regenerated in surgically created defects (including those of osteopenic or osteoporotic patients), presently cannot be directly measured in living subjects because such testing currently requires removal of significant segments of bone. Thus, direct measurement of bone mechanical strength can only be measured through post-mortem clinical retrieval studies. Nevertheless, research indicates that a substantial increase in strength would be expected in association with concurrent increases in BMD, as discussed herein. It further would be expected to achieve further increased bone properties, such as bone volume, trabecular thickness, trabecular number, separation of trabeculae, measurements of interconnectivity, and cortical wall thickness. Supportive evidence of such increases in mechanical strength is provided in the appended Examples in relation to a canine study in which both compressive strength and the amount of calcified bone were directly measured on explanted specimens of regenerated bone at both 13 and 26 weeks after undergoing a cavitation and filling procedure according to the present invention. At 13 weeks, the bone segments including the regenerated bone material exhibited a substantial 172% increase in calcified bone compared to normal bone taken from the same anatomic location, as measured by quantitative histology. The corresponding increase in compressive strength for the bone with the regenerated bone material over the compressive strength of natural bone was 283%. At 26 weeks post-op, the newly regenerated bone material had undergone remodeling, resulting in a gradual return towards normal bone architecture and properties. The 24% increase in calcified bone from histological analysis (again, compared to natural bone) corresponded to a compressive strength that was 59% higher than normal controls. It also is notable that increases in radiographic density were seen, which correlated to the quantitative results from histology.

Clinical evidence of BMD increases in human subjects is provided in the appended Examples and is believed to support the conclusion that increases in BMD can reasonably correlate to increases in bone mechanical strength, particularly compressive strength. Briefly, a study was performed using 12 human patients, all of whom were deemed to be osteoporotic according to the World Health Organization (WHO) definition. Each patient underwent treatment according to the present invention in one hip with the contralateral side remaining untreated for the purpose of comparison. BMD was measured in both hips via DEXA prior to treatment (baseline), and at pre-determined intervals including 6, 12, and 24 weeks. Mean femoral neck BMD increased 120%, 96% and 74%, respectively, at each interval compared to baseline. Mean Ward's area BMD increased 350%, 286% and 189%, respectively, at each interval compared to baseline. Two patients were further evaluated at a 24 month study endpoint. These two patients demonstrated mean BMD increases of 35% (femoral neck region) and 133% (Ward's area) at endpoint. Percent values at this level suggest the graft material was resorbed and replaced by new bone material as was observed in the canine study. There were no appreciable changes in BMD measurements from baseline in the untreated sides.

There are no known studies to date indicating that increased BMD and increased strength in a human osteoporotic bone can be precisely correlated to such values measured in healthy canine subjects. Nevertheless, the large increase in both properties in the canine study, together with the increase in BMD measured in the clinical trial, are strong evidence of a corresponding increase in bone strength for human osteoporotic bone that is treated according to the presently described methods.

Bone quality may also relate to the ability of the bone to resist fracture. Thus, embodiments of the invention that can be characterized as relating to increasing bone quality may specifically encompass improving the bone structure in a manner such that the treated area of the bone has a reduced risk of fracture in comparison to the risk of fracture prior to treatment (e.g., when the patient is in an osteopenic or osteoporotic condition).

Low BMD is among the strongest risk factors for fragility fracture. In addition, the deterioration of cancellous bone architecture is a contributory factor to bone fragility. So, while osteoporosis has traditionally been defined as a disease characterized by a lack of bone strength, it should be further defined as a disease of low bone density and the deterioration of bone quality. Although measurement of BMD is a powerful clinical tool and the "gold standard" for identifying bone mass, bone quality also is largely defined by bone turnover and microarchitecture. When these aspects of bone deteriorate (e.g., thinning trabeculae and loss of connectivity), there is a corresponding increase in bone fragility and fracture risk.

Various non-invasive methods can be employed to measure microarchitecture including, but not limited to, high-resolution peripheral quantitative computed tomography (pQCT), micro computed tomography (uCT), and functional magnetic resonance imaging (fMRI). Images obtained with such methods can be used to distinguish between cortical and cancellous bone and visualize fine details of trabecular microarchitecture previously only measured with an invasive biopsy. Scans from CT (and likely MRI) can be modeled computationally by microstructure finite element analysis (FEA) to assess bone stiffness. Each of these methods can be used to assess the architecture of bone. These architecture measurements include bone volume, trabecular thickness, trabecular number, separation of trabeculae, measurements of interconnectivity, and cortical wall thickness.

As technology has improved, so too has the outcome measurements of the computerized software. In combination, pQCT and FEA can be used to predict fracture initiation point and fracture potential under a specific load. This analysis is also known as biomechanical computation tomography (BCT). Used in conjunction with traditional studies, such as a comprehensive healthy animal study, an osteoporotic animal study, or a cadaveric biomechanical study, BCT can be used to predict the fracture potential of a patient—including the risk of a fracture during a fall—and provide information to assess bone quality improvement for a living patient without the need for an invasive biopsy. Because of its quantitative assessment, BCT can limit the inclusion/exclusion criteria for any study as the spectrum of patient bone quality is focused. Additionally, the duration of any study could potentially be reduced since only specific subsets of "at risk" as opposed to "estimated at risk" patients would be needed. Additionally, BCT can reduce the need for a finite endpoint, such as an actual hip fracture, which has a high association with mortality, to determine the benefit of a provided treatment.

Therefore, in certain embodiments, evidence of bone quality improvement according to the invention can be achieved by applying BCT analysis to an implanted bone matrix, as described above, in conjunction with other established scientific bone quality assessments. The combined results can be useful to analyze the change in bone density and bone quality over time and therefore demonstrate the overall fracture risk reduction after treatment according to the invention as compared to the condition of the natural bone prior to treatment (i.e., while the bone was in an osteopenic or osteoporotic condition). Using such methods, it thus can be possible to quantify fracture risk before treatment and after treatment according to the invention and, based upon the quantified data, illustrate the ability of the invention to reduce fracture susceptibility, or increase resistance to fracture. For example, fracture potential may be scaled similarly to T-score in BMD analysis such that a score of about 0 indicates the fracture potential is similar to the potential for an average, healthy adult of about age 30 (perhaps even including gender, race, and/or nationality data if evidence suggests such factors should be considered). A negative score could indicate a fracture potential that is greater than in the average, healthy adult with the potential increasing with more negative values (e.g., as score of −2 indicating a greater fracture potential than a score of −1). A positive score could indicate that fracture potential is less than in the average, healthy adult with the potential decreasing with more positive numbers (e.g., a score of 2 indicating a lesser fracture potential than a score of 1).

In specific embodiments, a method of improving bone quality at a localized area of a bone can comprise replacing a volume of degenerated bone having a T-score of less than −1.0 with newly formed, natural bone material having a T-score of greater than −1.0. Preferably, the T-score of the bone with the newly formed, natural bone material is at least −0.5, at least 0, at least 0.5, or at least 1.0. In certain embodiments, the T-score of the treated bone can exceed the T-score of the degenerated bone by at least 0.5 units, at least 1.0 unit, at least 1.5 units, at least 2.0 units, at least 2.5 units, or at least 3.0 units. In embodiments where the T-score of the treated bone exceeds the T-score of the degenerated bone by at least a certain amount, it may not be necessary for the T-score to also be greater than a defined minimum so long as the increase in BMD evidenced by the increase in T-score represents a sufficiently significant improvement in bone quality to be of use for the patient (e.g., transforming the bone in the localized area from a severely osteoporotic condition to a mildly osteoporotic condition or from an osteoporotic condition to an osteopenic condition).

In the method of improving bone quality, the replacing step can comprise forming a void in the localized area of the bone by clearing degenerative bone material in the area and optionally removing a content of the degenerative bone material. The method further can comprise at least partially filling the formed void with a bone regenerative material, thereby generating in-growth of new, natural bone material in the formed void.

In some embodiments, the ability to replace degenerative bone material with bone material of improved quality particularly can arise from the beneficial qualities of the bone regenerative material that is used to fill the formed void in the bone. Preferably, the bone regenerative material is a material as described herein that provides for reliable, consistent resorption by the body at a rate significantly consistent with the rate of new bone material generation by the body. For example, it can be particularly useful to utilize a material as described herein that provides multi-phasic resorption profile in vivo that can optimize the in-growth of new bone. Such materials can be bi-phasic (i.e., including at least two different materials that resorb at a different rate in vivo), tri-phasic (i.e., including at least three different materials that resorb at a different rate in vivo), or can include an even greater number of different materials that resorb at different rates in vivo.

In specific embodiments, the bone regenerative material may comprise calcium sulfate as a first phase component that is resorbed quickly, typically through simple dissolution, a brushite ($CaPO_4$) second phase component that undergoes osteoclastic resorption (as well as simple dissolution), and a tricalcium phosphate third phase that undergoes primarily osteoclastic resorption. Any material that exhibits such tri-phasic resorption profile could be used according to the invention. The changes over time in a bone regenerative material having this kind of structure that can facilitate controlled in-growth of new bone material are illustrated in FIGS. 7a-7e. Said figures illustrate graft dissolution in an accelerated in vitro model that is approximately six times faster than the resorption seen in vivo in a canine model. A more detailed discussion of the resorption profile of the bone regenerative material in relation to FIGS. 7a-7e is provided in the Examples below.

While all phases in a multi-phasic material may begin some degree of resorption shortly after graft placement, a multi-phasic resorbing material can be described as one wherein the first phase is dominated by resorption of the first material (e.g., a calcium sulfate material) until most of the first phase is gone, the second phase is dominated by resorption of the second material (e.g., brushite), and any further phases can be described as the time when the remaining graft material(s) (e.g., granular TCP) are resorbed. Specific times for complete resorption of each phase can depend upon the specific materials used and the defect size.

Angiogenesis is a key early event during first phase resorption because, as the calcium sulfate material resorbs, the porous second phase is revealed and is conducive to vascular infiltration. The porous second phase also can bind free proteins, such as VEGF and BMP-2, at the implant/ defect interface. Resorption of the second phase then can release bound proteins, which can recruit cells to the implant surface. The growth factors in the interface region can stimulate proliferation and differentiation of mesenchymal stem cells. Thereafter, differentiated osteoblasts lay down osteoid, which then mineralizes to become newly woven bone. The principles of Wolff's Law then can drive remodeling of the newly formed bone material. This is further beneficial to the patient in that strengthening of areas, such as the hip, that are prone to debilitating fracture can promote confidence in the patient that leads to greater movement and exercise, which in turn can have a positive effect on total bone quality and overall health.

In further embodiments, the invention provides methods for increasing BMD in a localized area of a bone. The method can comprise forming a void in the localized area of the bone, such as by clearing native, degenerated bone material in the localized area according to a suitable method, such as those described herein. The cleared, native bone material optionally can be removed from the formed void. The formed void then is at least partially filled with a bone regenerative material as described herein. The bone regenerative material filling the void can cause generation of new bone material within the void, the density of the newly generated bone material being greater than the density of the degenerated, native bone material that was cleared to form the void in the bone.

The increase in BMD can be indicated through comparison of BMD scans of the localized area of the bone prior to removal of the degenerated, native bone material and after generation of the new bone material within the formed void. For example, when using a DEXA scan, it is preferable for the density of the generated bone material within the void to have a T-score that is at least 0.5 units greater than the T-score of the degenerated, native bone material prior to being cleared to form the void. In further embodiments, the T-score may be increased by at least 0.75 units, at least 1.0 unit, at least 1.25 units, at least 1.5 units, at least 1.75 units, at least 2.0 units, at least 2.25 units, at least 2.5 units, at least 2.75 units, or at least 3.0 units. In other embodiments, T-score of the degenerated, native bone prior to formation of the void in the localized area of the bone specifically may be in a range indicating the presence of osteopenia or osteoporosis, and the increase in BMD may be sufficient so that the localized area of the bone no longer would be characterized as being osteopenic or osteoporotic. For example, prior to formation of the void, BMD in the localized area of the bone may be less than −1.0, less than −1.5, less than −2.0, less than −2.5, less than −3.0, less than −3.5, or less than −4.0. In such embodiments, BMD may be increased such that the T-score is at least at a minimum level. For example, BMD may be increased such that T-score is greater than −1.0 or is at least −0.75, at least −0.5, at least −0.25, at least 0, at least 0.25, at least 0.5, at least 0.75, or at least 1.0. In further embodiments, BMD in the localized area of the bone may be increased such that the T-score at the localized area of the bone can be in a range that is indicative of BMD falling within an accepted normal range. For example, T-score may be within the range of greater than −1 to about 2.0, about −0.5 to about 2.0, about 0 to about 2.0, about −1.0 to about 1.0, about −0.5 to about 1.0, about −0.5 to about 0.5, or about 0 to about 1.0. In specific embodiments, the T-score of the native bone material prior to being cleared for void formation can be less than −1.0, and the generated bone material in the formed void can have a T-score of at least −0.5 or at least 0, Such would indicate that the localized area of the bone prior to treatment would be considered to be at least osteopenic and that the localized area of the bone after generation of the new bone in the void would be considered to have a BMD that is substantially identical to normal BMD for a person of the same gender and race at the age of peak BMD. As previously described, the increase in BMD can be simply sufficient to evidence a relative improvement in BMD at the localized area.

In addition to the ability to cause formation of new, natural bone that is of a normal density, the invention beneficially allows for maintenance of the improved BMD for an extended period of time. As described above, it was surprising to find according to the present invention that newly formed bone material in an osteoporotic patient was not of osteoporotic quality but was substantially of the quality expected to be seen in a patient of the same gender and race at the age of peak BMD. Thus, the inventive methods have been found to be useful for essentially re-setting the bone quality in the localized area that is treated to the peak state (or to the normal state). Moreover, this re-setting of the localized area of the bone does not appear to be affected by the patient's overall osteoporotic status. In other words, the improved BMD is not a temporary phenomenon such that the newly formed bone material quickly degenerates to an osteoporotic state commensurate with the patient's overall status. On the contrary, the newly formed bone material appears to take on the full characteristics of the re-set status in that the newly formed bone material progresses along the natural decline in BMD, such as illustrated in FIG. 1. For example, as seen in FIG. 1, a 70 year old Caucasian female under a typical decline in BMD could have a localized hip BMD of about 775 mg/cm$^2$. After treatment according to the present invention, a localized area of hip bone could be re-set to a normal BMD—e.g., about 950 mg/cm$^2$ (or the typical BMD at 30 years of age). After 10 years of additional, typical decline in BMD, the same patient would be expected to have an average BMD of around 700 mg/cm$^2$ (i.e., the decline in typical BMD between 70 and 80 years of age). The bone material in the localized area of the hip treated according to the invention, however, would be expected to be about 930 mg/cm$^2$ (i.e., the decline in typical BMD between 30 and 40 years of age). Of course, it is understood that the foregoing is only an exemplary characterization based on average values, and it is expected that actual values could vary between patients. Thus, it is evident that the inventive methods are not temporary solutions but can provide long-term increases in BMD since the bone material generated by the inventive methods is in effect re-set to a peak state and then continues through the typical, natural decline in density that accompanies aging (i.e., does not decline at an accelerated rate to "catch-up" to the systemic osteoporotic state of the patient).

In light of this characteristic of the invention, certain embodiments may encompass maintenance of the increased BMD for a defined period of time. For example, the increase in BMD in the localized area of the bone may be maintained for a time of at least 6 months, at least 1 year, at least 18 months, at least 2 years, at least 3 years, at least 4 years, at least 5 years, or even longer. Measurement of the time may be calculated from the time new bone material is generated in the formed void. Preferably, maintenance of the increased BMD includes maintaining a T-score that is greater than −1.0, greater than −0.5, greater 0, or greater than 0.5. In other embodiments, maintenance of the increased BMD includes maintaining a T-score that is in the range of greater than −1.0 to 1.0, −0.5 to 1.0, or −0.5 to about 0.5. Similarly, the increase may be characterized as a percentage increase in relation to untreated bone. Thus, the treated bone may exhibit an increase in BMD for any of the time periods noted above, such increase in BMD being at least 10% greater, at least 15% greater, at least 20% greater, at least 25% greater, at least 30% greater, at least 35% greater, at least 40% greater, at least 45% greater, at least 50 greater, at least 60% greater, at least 70% greater, at least 80% greater, or at least 90% greater than the reference, untreated bone in the same subject.

Figure 8:
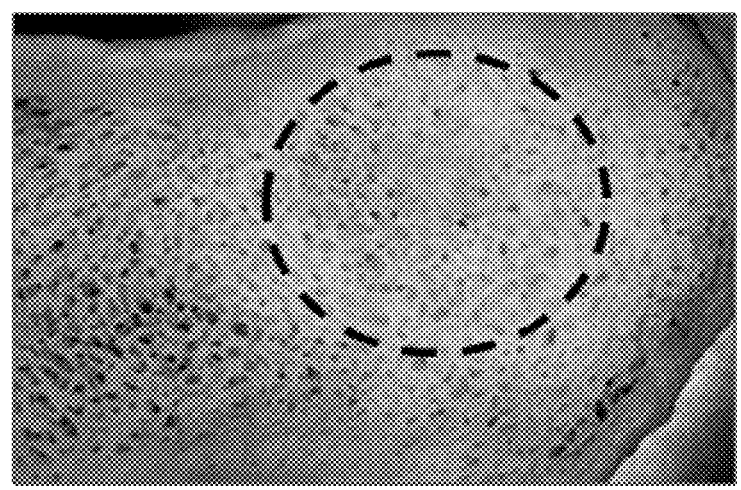
FIG. 8 shows a 13-week gross specimen in the canine proximal humerus after insertion of a graft formed of a bone regenerative material according to the present invention and shows formation of dense, cancellous bone, even beyond the margins of the original defect.

The methods of increasing BMD further are beneficial in that the increase in BMD in the localized area of the bone may extend beyond the borders of the void created in the bone. As seen in FIG. 2a and FIG. 2b, bone material is porous in nature being essentially of a series of interpenetrating networks of scaffolding material formed of bone cells. In healthy bone, the network is tightly formed for dense, strong scaffolding material. In osteoporotic bone, the network begins to degrade, the scaffolding thins, weakens, and even falls apart, and the porosity of the bone increases. Although not wishing to be bound by theory, it is believed that because of this nature in osteoporotic bone, the filling of the void formed in a bone according to the present invention can cause the bone regenerative material to fill portions of the bone in the areas adjacent the formed void. Thus, while new, normal bone material is generated within the formed void as the bone regenerative material is resorbed by the body, such new, normal bone material also is generated in the areas of the bone adjacent the formed void as a result of the bone regenerative material extending beyond the borders of the filled void. Moreover, such formation of new, healthy bone material exterior to the formed void can arise from increased biological activity, such as involving growth factors and cytokines at the interface that boost the biological activity outside of the void margins. In some embodiments, this can even lead to a gradient effect wherein the density of the bone material in the localized area of the bone that is treated according to the invention is at its lowest outside of the void and away from any location where the bone regenerative material may have entered, and the density of the bone material gradually increases moving toward the area of the formed void. A gradient effect thus may be elicited as per the following example for an osteoporotic bone: the bone material immediately in the area where the void was formed may have a normal or greater density (e.g., T-score of around 0 to 1); the bone material immediately adjacent the area of the formed void may also have a substantially normal density, albeit less than inside the area where the void was formed (e.g., a T-score of around −0.5 to 0.5); the bone material somewhat further away from the formed void may also exhibit an increased density, albeit less than bone material immediately adjacent the formed void (e.g., a T-score of around −2 to −1); and the bone material further away from the formed void may retain its original, osteoporotic density (e.g., a T-score of less than −2.5). Of course, the foregoing is merely exemplary of the gradient effect, and actual T-scores and the extent of the effect in relation to effective distance away from the formed void may vary depending upon the actual density of the bone at the time of the procedure, the type of bone regenerative material used, and the force with which the bone regenerative material is placed into the formed void and thus may extend beyond the borders thereof. This is further illustrated in FIG. 8, which shows a 13-week gross specimen in the canine proximal humerus after insertion of a graft formed of a bone regenerative material according to the present invention. The figure illustrates formation of dense, cancellous bone at the graft site and new bone material extending even beyond the margins of the original defect indicated by the dashed line.

In further embodiments, the methods of the invention can be characterized in relation to a specific BMD profile elicited in a localized area of a bone. As noted above, the inventive methods have been found to not only re-set the newly formed bone material to a normal density, but the methods also can cause the density in the localized area of the bone to dramatically increase prior to attaining a substantially normal density. This can be characterized as a remodeling of the bone in the localized area according to a specific density profile.

In some embodiments, the methods of creating a defined BMD profile in a localized area of a bone can comprise forming a void in the localized area of the bone by clearing degenerated bone material in the area, and optionally removing a content of the cleared, degenerated bone material. Although is not required for the bone material to be removed from the void during or after void formation, it may be desirable in some embodiments to partially or completely remove the degenerated bone material from the void to maximize the amount of the bone regenerative material that may be placed within the void. Accordingly, after void formation, the methods may further comprise at least partially filling the formed void with a bone regenerative material such that new bone material is generated within the void over time.

As the new bone material is generated within the void, part or all of the bone regenerative material may be resorbed by the body. Specifically, new bone in-growth may proceed, particularly in an outside to inside manner in reference to the formed void, at a rate substantially similar to the rate of resorption of the bone regenerative material by the body.

Importantly, the newly generated bone material in the formed void can be accurately characterized as being natural bone material (in reference to the patient) in that the formed bone material arises from influx of osteocytes from the treated patient and is not allogenic bone or xenogenic bone. Thus, there is no little or no opportunity for the bone regenerative material to elicit an immune response that could limit the effectiveness of the bone replacement treatment.

Figure 9:
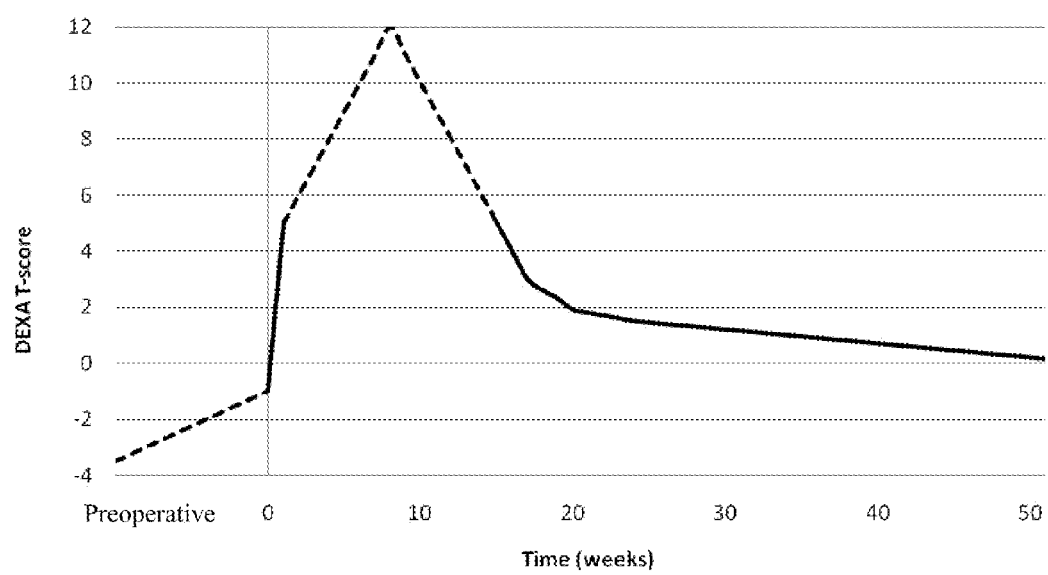
FIG. 9 is a graphical representation of an exemplary BMD profile that can be elicited in a localized area of a bone according to one embodiment of the invention.

Regarding the defined BMD profile, successive BMD evaluations over time, such as successive DEXA scans, can provide a time-lapse profile of BMD in the localized area of the bone arising from the implantation of the bone regenerative material. The BMD profile provided according to the present invention is particularly unexpected because the use of the bone regenerative material in a surgically created void elicits a change in the localized area of the bone such that BMD initially spikes to be significantly denser than normal bone and then remodels over time with in-growth of new bone material such that the density of the localized area of bone treated according to the present invention approaches a substantially normal value. The nature of a BMD profile achieved according to certain embodiments of the present invention is shown in FIG. 9, wherein BMD reported as a DEXA scan T-score is charted as a function of time, where time 0 is the time of void formation and implantation of the bone regenerative material. FIG. 9 illustrates a profile wherein the localized BMD of the bone to be treated according to the invention is such that the bone would be considered to be osteopenic or osteoporotic (i.e., a T-score of less than −1 or less than −2.5). The broken line shown before time 0 indicates that the actual BMD, as characterized by T-score, can be any value below the defined threshold (e.g., less than −1, less than about −2.5, etc.). Upon replacement (at time zero) of the degenerated bone in the localized area with the bone regenerative material, the BMD in the localized area begins to sharply increase to reach a maximum density. As illustrated in the representative graph of FIG. 9, a maximum density corresponding to a T-score of greater than about 5 is achieved within a time of about 1 week to about 13 weeks. The solid line in FIG. 9 illustrates this sharp increase in BMD, and the dashed line above a T-score of 5 indicates that the maximum T-score achieved can be some value in excess of 5 and can typically occur at some time in the range covered by the dashed line. In specific embodiments, the maximum T-score achieved according to the defined BMD profile is at least 2.0, at least 3.0, at least 4.0, at least 5.0, at least 6.0, at least 7.0, at least 8.0, at least 9.0, or at least 10.0. The time after implantation to achieving maximum density (i.e., maximum T-score) can be in the range of about 1 week to about 6 weeks, about 1 week to about 10 weeks, about 1 week to about 13 weeks, about 1 week to about 18 weeks, about 2 weeks to about 10 weeks, about 2 weeks to about 13 weeks, about 2 weeks to about 18 weeks, about 3 weeks to about 10 weeks, about 3 weeks to about 13 weeks, about 3 weeks to about 18 weeks, about 4 weeks to about 10 weeks, about 4 weeks to about 13 weeks, about 4 weeks to about 18 weeks, about 6 weeks to about 10 weeks, about 6 weeks to about 13 weeks, or about 6 weeks to about 18 weeks. After reaching a maximum density, the density of the localized area of the bone begins to decrease for a time of up to about 6 months, up to about 9 months, up to about 12 months, up to about 18 months, up to about 24 months, from about 6 weeks to about 24 months, from about 13 weeks to about 18 months, or from about 18 weeks to about 12 months. Thereafter, the BMD of the localized area of the bone stabilizes in a substantially normal range about −1.0 to about 2.0, about −1.0 to about 1.0, about −1.0 to about 0.5, about −1.0 to about 0, about −0.5 to about 2.0, about −0.5 to about 1.5, about −0.5 to about 1.0, about −0.5 to about 0.5, about 0 to about 2.0, about 0 to about 1.5, or about 0 to about 1.0. With the foregoing values in mind, further graphs similar to that shown in FIG. 9 could be prepared providing representative BMD profiles encompassed by the invention that differ only in the maximum BMD achieved and/or the time to achieving maximum BMD, and/or the time after achieving maximum BMD until BMD decreases to the substantially normal range. Actual embodiments of BMD profiles achieved in test subjects are described in the Examples shown below.

In further embodiments, the BMD may be substantially maintained such that the defined BMD profile may be extended for a prolonged period. In other words, BMD corresponding to a T-score of about −1.0 to about 2.0, about −1.0 to about 1.0, about −1.0 to about 0.5, about −1.0 to about 0, about −0.5 to about 2.0, about −0.5 to about 1.5, about −0.5 to about 1.0, about −0.5 to about 0.5, about 0 to about 2.0, about 0 to about 1.5, or about 0 to about 1.0 may be maintained for an additional year or more (i.e., the BMD profile in the localized area of the bone may be such that BMD as reported by a T-score within the noted ranges may be established and maintained for a time of at least 1 year, at least 2 years, at least 3 years, at least 4 years, at least 5 years, or even more).

In further methods, the present invention may be characterized in relation to the effect previously described above in relation to remodeling of a localized area of degenerative bone to be substantially identical to normal bone. In certain embodiments, the invention particularly may be directed to methods of remodeling a localized area of degenerative bone comprising the following steps: forming a void in the localized area of the bone by clearing degenerative bone material in the area and optionally removing a content of the degenerative bone material; and at least partially filling the formed void with a bone regenerative material thereby generating in-growth of new bone material in the formed void. Specifically, the remodeling of the localized area of the bone can be evidenced by the ability to cause the growth of new, natural bone material in an area of the bone that was previously osteopenic or osteoporotic (i.e., was bone that was considered to be degenerated or otherwise viewed as being diseased and/or of low quality, strength, and/or density).

In certain embodiments, the bone material in the localized area treated according to the invention (i.e., before forming the void) has a T-score of less than −1.0, which indicates bone degeneration beyond what typically is considered a normal level, and the new bone material present after remodeling has a T-score of greater than −1.0, which indicates that the bone in the localized area has been remodeled to be substantially identical to normal bone. In such embodiments, the bone may be considered to have been remodeled in the localized area because that area of the bone has effectively been changed so that is no longer is considered to be degenerated bone, osteopenic bone, osteoporotic bone, or the like, but is rather considered to be in a state that is significantly similar to bone of normal density for a person of the same gender and race at peak BMD (i.e., normal bone). In other words, the bone is remodeled from natural bone of low density to natural bone of normal density.

This is not an effect that would have been expected prior to the present invention. Osteoporosis (i.e., significant loss of BMD) is typically seen as a systemic condition. Although actual T-score may vary from site to site in the same patient, generally when osteoporosis is present, the condition persists throughout the body (e.g., a T-score of −2.8 in the distal radius versus a T-score of −3 in the hip). As described above, it has been found according to the present invention that although osteoporosis progresses systemically, it is possible to locally re-set the body's bone quality. In other words, a localized area of bone can be remodeled away from an osteoporotic state to a normal state. This is unexpected because osteoporosis is understood to arise from the body's decreased ability to form new bone cells such that the rate of bone cell resorption exceeds new cell formation. One would assume that newly formed bone growing into an injury site would simply be an extension of the surrounding bone—i.e., bone of low quality would beget bone of low quality. The present invention shows the opposite is true. By systematically removing defined volumes of bone material in localized areas of bone and replacing the material with a bone regenerative material as described herein, the overall process sets in motion a regenerative process wherein the influx of new bone cells causes formation of new, natural bone material that is not merely an extension of the degenerative bone in the surrounding area but is bone material substantially identical to normal bone of normal density.

Figure 10:
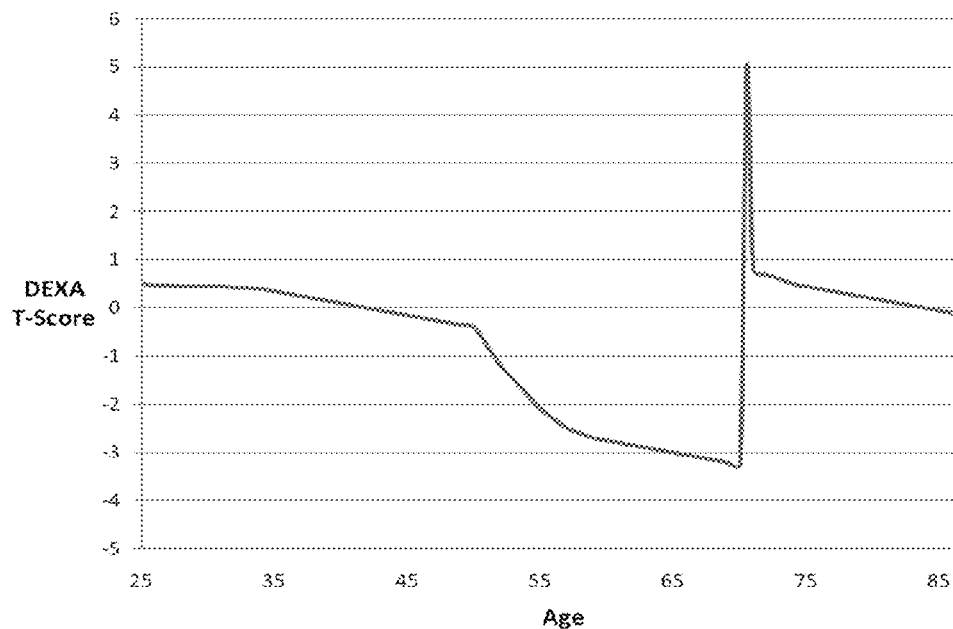
FIG. 10 is a graph showing bone remodeling in a localized area of a bone showing altering of the BMD from an osteoporotic model to a model substantially identical to normal bone.

This remodeling is graphically illustrated in FIG. 10, wherein the decline in BMD in a localized area of a bone in a Caucasian female is estimated. As seen therein, BMD in the localized area declines from a normal range around the age of 30, and the rate of decline increases around the time of menopause and then levels off to a less sharp decline. The point at age 70 on the graph represents the time of undergoing a procedure according to the present invention. The BMD at the localized area increase dramatically and re-sets to a normal range (i.e., around the same density at age 30). From that time forward, the new bone material in the localized area continues a natural decline in BMD associated with aging. Thus, the localized area of the bone has effectively been remodeled from an osteoporotic state to a normal state.

The exact values shown in FIG. 10 are only representative since the actual T-score values may vary from patient to patient. The overall remodeling effect, however, would be expected to be consistent from patient to patient. In other words, although the exact BMD values may be somewhat greater or lesser than illustrated, the remodeling would be consistent in the following: the bone would exhibit a declining density to the point of reaching an osteopenic or osteoporotic state; after implantation of a bone regenerative material according to the methods of the invention, there would be a rapid increase in BMD above a substantially normal range; the BMD would decline to a substantially normal range; and BMD would take up a rate of decline typically exhibited by healthy bone material. Importantly, when the rate of normal decline is again achieved after implantation, the decline begins from a point of BMD typically exhibited in a normal, healthy individual at peak BMD age. Thus, although BMD does continue to decline, the basis has been changed to a normal density range and not an osteopenic or osteoporotic density range. This is particularly important when the procedures of the invention are carried out on women that have already undergone menopause in that the rapid decline in BMD associated with menopause will not be able to affect the newly grown, dense bone. Depending upon the age of the female patient at the time of treatment and the life span of the individual, resetting the nature of the bone in the localized area can effectively alter the structure in the localized area such that the localized area of the bone never achieves an osteopenic or osteoporotic state again during the lifetime of the patient after treatment. This ability to remodel osteopenic and osteoporotic bone material to be substantially similar in structure to normal bone material is further illustrated in the Examples provided below.

In addition to causing remodeling of the area of the degenerative bone defined by the formed void, the invention also can cause remodeling of the degenerative bone material in substantially close proximity to the formed void. As described above in relation to FIG. 8, the provision of the bone regenerative material in the formed void can lead to a gradient effect wherein not only is new bone material generated in the void that was filled with the bone regenerative material, but new bone material also can be formed in the area of the bone adjacent the formed, filled void. Similarly, the invention can provide for remodeling of the degenerative bone material in a localized area of a bone to the extent that bone material having a T-score within the described range can be formed in the area of the bone adjacent the formed void. Thus, degenerative bone material in a localized area of a bone that was not cleared and/or removed to form the void also can undergo remodeling to be substantially normal. Specifically, newly grown bone material may be graded in structure such that the T-score of the bone material may increase from the area around the void to the area within the void.

Also as already discussed above, a localized area of a degenerative bone that is remodeled to be substantially identical to normal bone preferably maintains the characteristics of the remodeled state for an extended period of time. For example, the remodeled, localized area of the bone can remain substantially identical to normal bone for a time of at least about 1 year, at least about 2 years, at least about 3 years, at least about 4 years, at least about 5 years, or even longer.

The invention can be utilized in relation to existing surgical procedures, such as kyphoplasty or vertebroplasty. Unlike these existing procedures, the methods used according to the invention would be carried out on patients that are not currently suffering from a vertebral fracture or otherwise weakened vertebra. Rather, the present methods can be characterized as being carried out prophylactically (i.e., to prevent a later fracture in a degenerated bone). Specifically, in relation to the vertebrae, the surgical method may be carried out on an osteoporotic vertebra that is not fractured, but the surgical method used may be similar to a surgical method employed in a traditional kyphoplasty. In such embodiments, the methods of the invention may be as otherwise described herein and be specifically carried out on one or more vertebrae in a patient.

In other embodiments, the invention may be carried out on a vertebra that is already fractured. Rather than carrying out a traditional kyphoplasty, which would typically involve filling the fractured area with a cement material, such as poly(methyl methacrylate) (PMMA), the present invention can provide for expanding or increasing the fracture as necessary to form a void within the vertebra and filling the void with a bone regenerative material. In specific embodiments, the vertebra treated according to the invention is osteopenic or osteoporotic.

Thus, in certain embodiments, the invention can be described as providing a method of restoring vertebral body height or correcting angular deformity in a fractured vertebra (specifically a fractured, osteopenic or osteoporotic vertebra) by causing in-growth of new bone material that is substantially identical to normal bone. Specifically, the method may comprise forming a void in the area of the fracture by mechanically clearing damaged or degenerated bone material in and around the fracture and optionally removing a content of the cleared bone material. The method further can comprise at least partially filling the formed void with a bone regenerative material such that new bone material is generated within the void over time. Preferably, the new bone material that is formed has a T-score indicating that the new bone material is substantially identical to normal bone. In specific embodiments, the T-score of the new bone material can be greater than −1, at least −0.5, at least 0, at least 0.5, or at least 1.0 (or otherwise within a normal range as described herein). Moreover, the invention is advantageous in that the new bone material can remain substantially identical to normal bone for a time of at least about 1 year (or more, as otherwise disclosed herein). Such time can be measured from the time of new bone material generation in the area of the bone where the void was formed and filled with the bone regenerative material.

Although it is believed that the present invention provides distinct advantages over other, known methods and materials for treating osteoporosis and/or osteopenia, the present invention need not necessarily be utilized to the exclusion of other treatments. Specifically, the present methods of replacing degenerative bone material with newly grown bone material that is native to the patient and is substantially normal in bone quality may be used in conjunction with pharmaceutical interventions recognized in the art as beneficial for treating osteoporosis and/or osteopenia. For example, treatment of patients according to the invention may be carried out while the patient simultaneously is partaking of pharmaceutical treatments, including hormone therapies (e.g., estrogen, SERM's, calcitonin, and recombinants, such as rPTH), bisphosphonates, and antibodies (e.g., denosumab). Such pharmaceutical treatments may be carried out prior to, concurrently with, or after treatment according to the present invention. Specifically, such treatments could be stopped for a specific length of time prior to carrying out the inventive method. Likewise, such treatments could be started a specific length of time after carrying out the inventive method.

In another aspect, the present invention also provides materials that can be used in methods for replacing degenerated bone as described herein. Specifically, the various materials can be pre-packaged in kit form. Thus, the inventive methods, or specific steps in the methods, can be carried out using instruments from a kit comprising various components. Exemplary materials that may be provided in a kit according to the invention are described below.

A kit according to the invention preferably would include a drilling instrument, which could comprise a drill and/or a drill bit, such as a cannulated drill bit. For example, a 5.3 mm OD cannulated drill could be included. A kit also may include one or more of a guide wire, a syringe, means for delivering a bone regenerative material to a void, such as a large gauge injection needle, a working cannula, a suction device, an aspiration device, a tamp device, a curette, a reaming device, and means for bending an instrument (such as a needle or a tamp) to a defined angle. In some embodiment, the kit may include one or more tamp devices (e.g., a debridement probe) having a head with a defined geometry. In further embodiments, the kit may include a reaming device such as the X-REAM™ Percutaneous Expandable Reamer (available from Wright Medical Technology, Inc., Arlington, Tenn.) or a similar instrument of suitable dimensions for use according to the methods described herein. For example, any in situ expandable device suitable for debriding bone or surgically creating a defect could be used. In specific embodiments, the kit may include an amount of a bone regenerative material suitable for filling a void in a localized area of a bone.

Any materials useful for debridement of a bone can be included in the inventive kit. For example, in addition to curettes, rasps, trephines, and the like, one could use an expanding device to create a space (expansion through balloon, beaded bag, meshed bag, flexible wire, flexible and/or perforated tubes, expanding whisk, rotating wire, expanding blade, non-expanding flexible blade, or other similar devices). All of the foregoing could be manually powered, or mechanized. They could be constrained (e.g., a preformed blade stuck through an opening in a tube), or unconstrained (e.g., a blade that is deformed through an opening in the tube).

Figure 11:
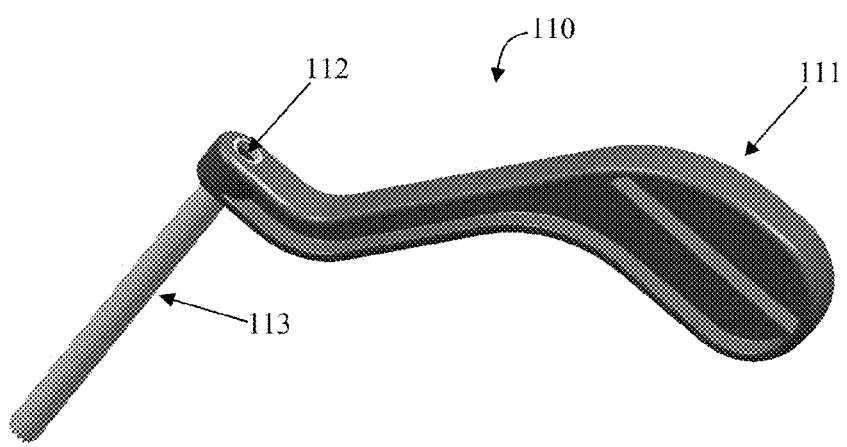
FIG. 11 is an illustration of a tissue protector instrument that may be used in carrying out a method according to an embodiment of the invention.
Figure 12:
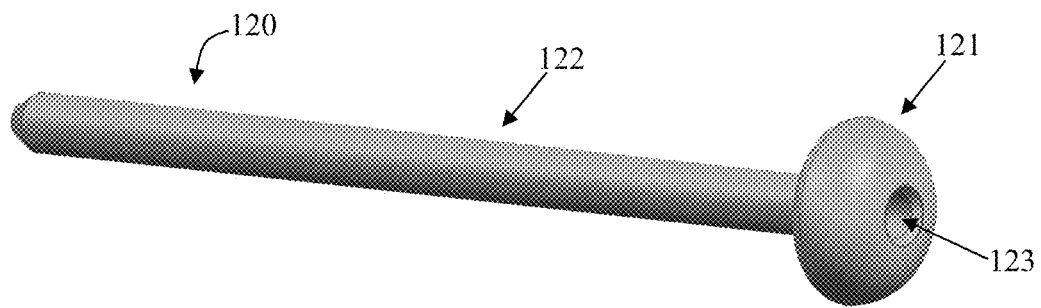
FIG. 12 is an illustration of a cannulated obdurator that may be used in carrying out a method according to an embodiment of the invention.
Figure 13:
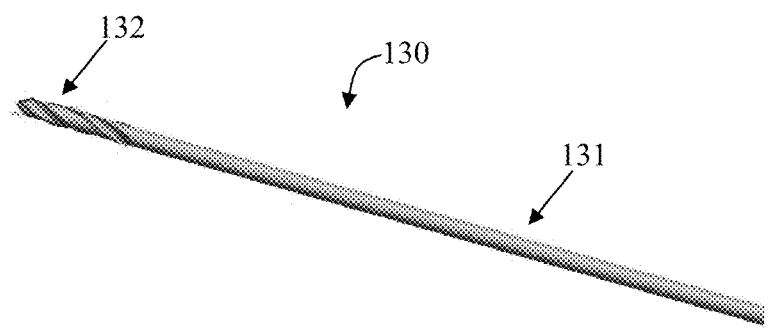
FIG. 13 is an illustration of a guidewire that may be used in carrying out a method according to an embodiment of the invention.
Figure 14:
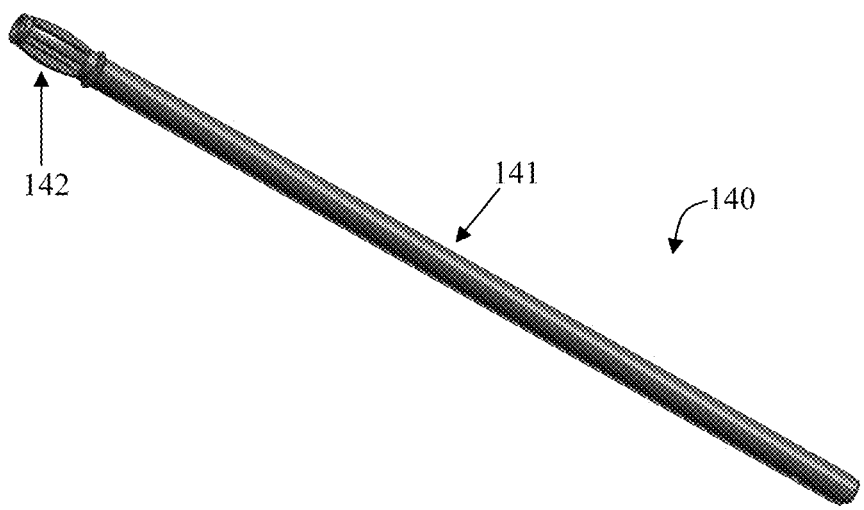
FIG. 14 is an enlarged illustration of the tip of a drill that may be used in carrying out a method according to an embodiment of the invention.
Figure 15:
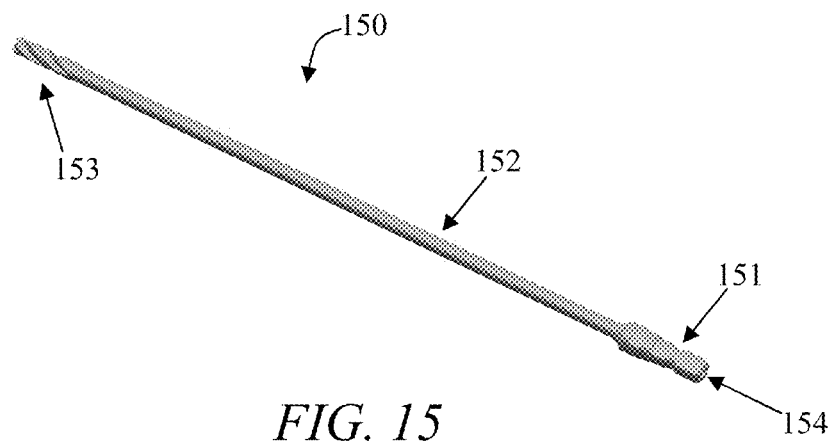
FIG. 15 is an illustration of a flexible working cannula that may be used in carrying out a method according to an embodiment of the invention.
Figure 16:
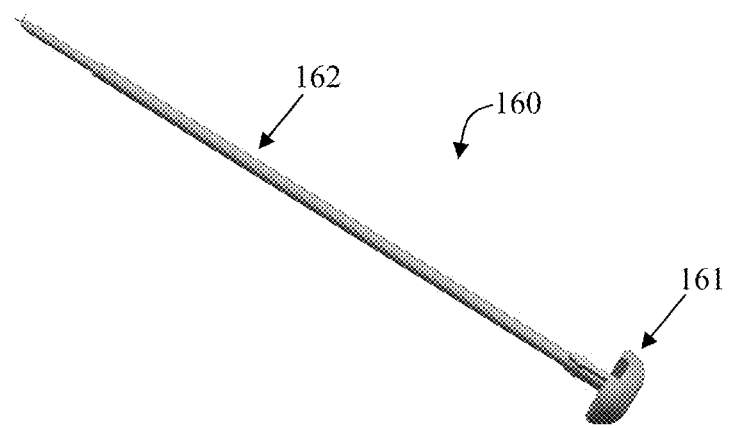
FIG. 16 is an illustration of a working cannula obdurator that may be used in carrying out a method according to an embodiment of the invention.
Figure 17:
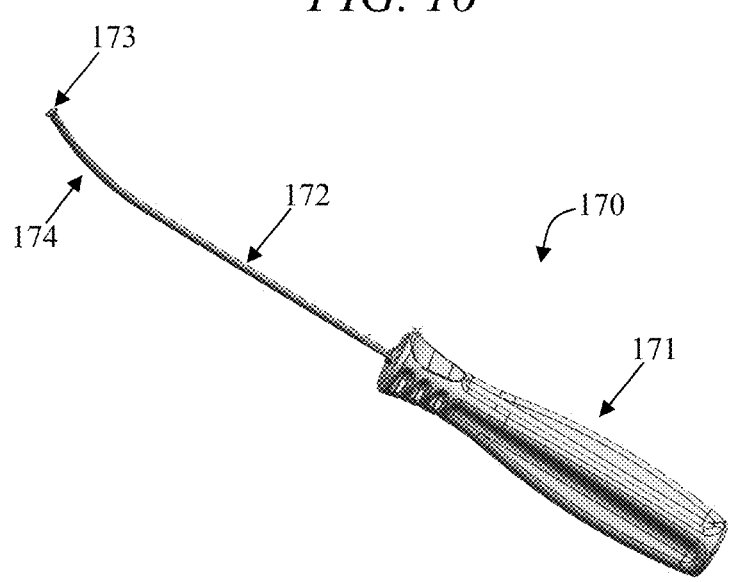
FIG. 17 is an illustration of a debridement probe that may be used in carrying out a method according to an embodiment of the invention.
Figure 18:
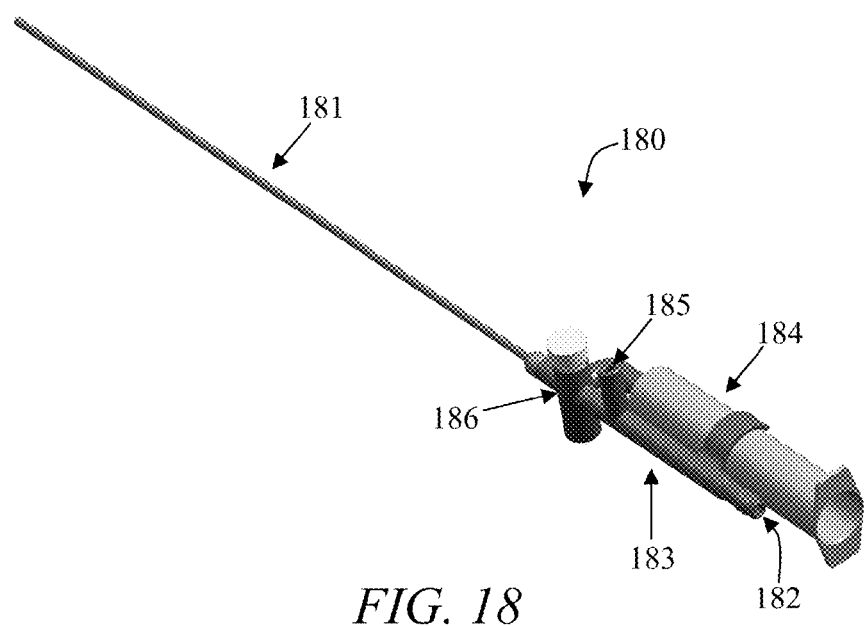
FIG. 18 is an illustration of a suction/irrigation instrument that may be used in carrying out a method according to an embodiment of the invention.
Figure 19:
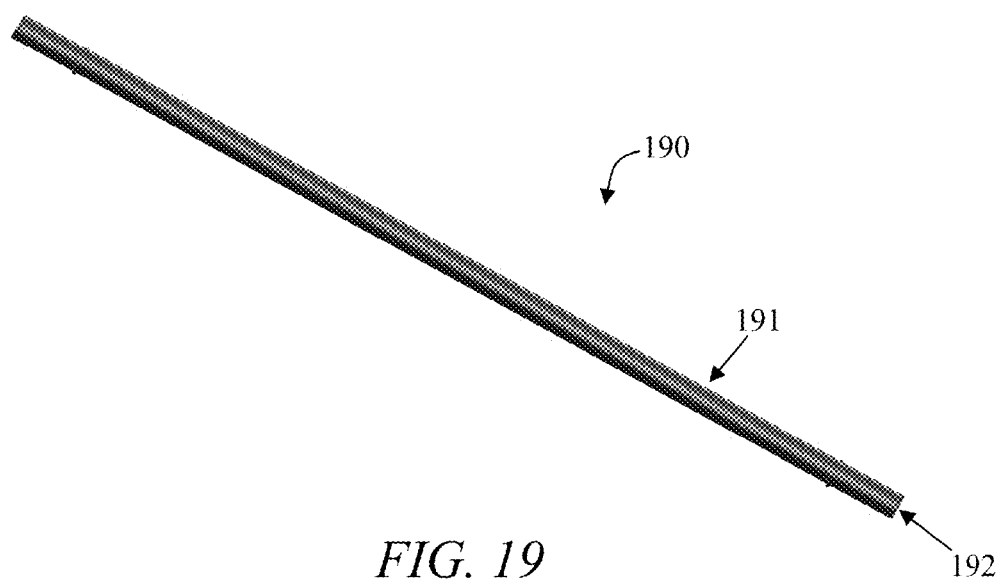
FIG. 19 is an illustration of a 180° working cannula that may be used in carrying out a method according to an embodiment of the invention.

Specific examples of instruments that may be useful in carrying out embodiments of the present invention, and thus may be included in a kit according to the invention, are illustrated in FIG. 11 through FIG. 19. FIG. 11 illustrates a tissue protector that functions to provide a safe passage for other instruments (e.g., a drilling instrument) from outside the body into the body by protecting surrounding soft tissues from damage. The tissue protector 110 includes a handle 111 and an elongated body 112 with an open channel 113 therein. FIG. 12 illustrates a cannulated obdurator, which can be used to centralize placement of a guidewire (and may be passed through the interior of the tissue protector). The obdurator 120 includes a flared head 121, an elongated body 122, and an open channel 123 therein. FIG. 13 illustrates the cutting head section of a guidewire, which facilitates cutting into the bone while maintaining the placement location in vivo. The guidewire 130 includes a body 131 (shown in part) and the cutting head 132, which is sufficient to cut into a bone without forming a substantial drilled passage. FIG. 14 illustrates a drill, which is used to create a passage or tunnel of defined dimension (e.g., 5.3 mm diameter) into the bone. The drill 140 includes a body 141 and a cutting head 142. FIG. 15 illustrates a flexible working cannula. Working cannulas function to provide safe passage of further working instruments (e.g., debridement tools and syringe needles) into the interior of the bone while protecting the surrounding tissues. The illustrated cannula 150 includes a head 151, which is shaped for attachment to further devices, a body 152, a cutting head 153, and an open channel 154 therein. FIG. 16 illustrates a further obdurator that may be used with a cannula, the obdurator 160 including a flared head 161 and an elongated body 16, and may include a central channel (not shown). FIG. 17 illustrates a debridement probe that is inserted into the bone to clear degenerated bone material and form a void within the bone. The probe 170 includes a handle 171, an elongated body 172, a head 173 (which may take on a particular dimension or shape for clearing of bone material), and a curved portion 174. The presence of the curved portion can be particularly advantageous to position the head 173 for void formation of desired shape and volume. The curved portion 174 may define an angle relative the body 172 of about 5° to about 90°, about 10° to about 75, about 10° to about 60, about 15° to about 50°, or about 15° to about 45°. FIG. 18 illustrates a suction/irrigation device 180, which includes an elongate body 181 with an open channel 182 therethrough. The device also includes a base 183 that accommodates an irrigation component (a syringe body 184, as illustrated) and a suction component (a port 185 as illustrated) that may be connected to a vacuum source (not illustrated). The device further includes a control valve 186 to control application of suction and/or irrigation through the channel 182. FIG. 19 illustrates another working cannula (a trough working cannula 190) that includes a body 191 with a channel 192 therethrough.

A kit according to the invention may include one or more or any combination of the illustrated instruments, or further instruments that may be useful in carrying out a method according to the invention. In certain embodiments, a kit would include all instruments and bone regeneration material necessary to perform an osteosupplementation procedure. This may include instruments necessary to provide for skin incision, bone void creation, debridement, mixing of the bone regeneration material, and delivery of the bone regeneration material. Various combinations of the following components particularly could be included into an osteosupplementation kit according to the invention: scalpel, tissue protector, cannulated obdurator, guidewire, drill, working cannula, debridement probe, suction/irrigation device, bone regenerative materials (including solid and liquid components for forming a flowable material prior to implantation into the formed void, preferably by injection), mixing apparatus (e.g., a mixing chamber), syringe, and delivery needle (or other instruments useful for delivering the bone regenerative material into the created void.

In some embodiments, a kit may include only a minimal content of components necessary to carry out the invention. For example, minimally, a kit could include a debridement probe (e.g., a probe of specific bent geometry—such as an angle within any of the ranges described herein) and/or a drill for forming a specific sized entry channel and/or the bone regenerative materials. In other embodiments, a cannulated obdurator also may be included. In yet further embodiments, a working cannula could be included. In still other embodiments, a suction/irrigation device could be included. In still other embodiments, a tissue protector could be provided. In yet another embodiment, a guidewire also could be included. In still other embodiments, a mixing apparatus may be included. In another embodiment, a syringe and delivery needle may be included. Even further instruments, as may be evident to the skilled person with the benefit of the present disclosure, could be included in a kit according to the present invention.

In addition to any of the above described components, a kit according to the invention can include an instruction set that instructs how to use the kit components to treat a patient suffering from a degenerative bone condition. For example, the instruction set may provide instructions for using a scalpel to make an access to the bone to be treated, using a tissue protector within the incision to protect surrounding tissue, using a guidewire or guide pin to form an initial entry path into the bone, using a drill to form a channel into the interior of the bone, using a debridement tool to clear degenerated bone material, using a suction tool to remove cleared bone material, mixing of the bone regenerative material (if necessary), using a syringe to inject the bone regenerative material into the formed void, using an irrigation device to clean the tissue area, and using closures to close the tissue access incision. Similar instructions could be included in relation to any combination of instruments included in a specific kit. Further, the instructions may be in any suitable form (e.g., written (such as a manual, pamphlet, one or more written sheets, etc.) or digital media (such as CD, DVD, flash drive, memory card, etc.).

EXPERIMENTAL

The present invention is more fully illustrated by the following examples, which are set forth to illustrate the present invention and provide full disclosure, and are not to be construed as limiting thereof.

Example 1

Resorption Characteristics of Tri-Phasic Bone Regenerative Material

An accelerated model illustrating the resorption characteristics of a tri-phasic bone regenerative material was carried out using pre-cast and weighed 4.8 mm×3.2 mm pellets of the bone regenerative material that is commercially available under the name PRO-DENSE®. The test was designed to illustrate the changes over time in the bone regenerative material for facilitating controlled in-growth of new bone material. The accelerated in vitro model is approximately six times faster than the resorption seen in vivo in a canine model, and the resorption rate of the in vitro model is even faster in relation to human models.

To begin the evaluation, the pellets were immersed in distilled water. For daily testing, the pellets were removed from the water, dried, and weighed to determine percent mass remaining. The pellets were placed in fresh aliquots of distilled water after measurements were taken. To analyze microscopically, the pellets were embedded, cross sectioned and analyzed using scanning electron microscopy (SEM) at 35× magnification.

The initial state of the bone regenerative material is shown in FIG. 7a. The pellet is shown at 4 days in vitro in FIG. 7b (which would be expected to correspond to the state at about 24 days in vivo). There is an initial burst of calcium sulfate dissolution from the surface of the pellet, which exposes an outer layer of fine brushite crystals and larger TCP granules (bright white in the SEM images). The brushite forms a diffusion barrier that slows the rate of $CaSO_4$ dissolution. At 8 days in vitro (approximately 48 days in vivo) the procession of dissolution is seen in FIG. 7c, and it is observed that the brushite crystals on the exterior of the pellet (those that were first exposed) become less dense, indicating that the brushite is also dissolving. FIG. 7d shows the pellet at 12 days in vitro (approximately 72 days in vivo), and it can be seen that the relatively dense region of brushite that surrounds the intact portion of the pellet moves inward as dissolution continues. Finally, complete calcium sulfate dissolution is seen in FIG. 7e as the TCP granules form an evenly distributed scaffold after the majority of the $CaSO_4$ and brushite have dissolved. It is likely that some of the brushite remains attached to the TCP and acts to hold the granules together.

Example 2

Comparative Fracture Resistance in Osteoporotic Bone Before and after Void Formation and Filling with Bone Regenerative Material To evaluate the effect on fracture susceptibility immediately after performing a procedure according to the invention, cadaver studies were carried out using ten matched pairs of osteopenic or osteoporotic proximal femora. Initial DEXA scans were carried out at the femoral neck and Ward's area, and the T-scores for all tested bones were less than or equal to −2.0, which was indicative of the bone material being in an osteopenic or osteoporotic condition at the time of the testing. The matched pairs were the right and left femur from the same cadaver. In each test, a defect was created in one femur and filled with PRO-DENSE® graft material. The radiographs in FIG. 20 and FIG. 21 show, respectively, insertion of a debridement probe used in creation of the void in the proximal femur and the graft material in place (dark area) filling the formed void. The contralateral femur was left intact as a control. After allowing time for the graft material to set, each proximal femur in the matched set was loaded in compression at 20 mm/sec until failure was reached.

Test results showed no significant difference in peak load between the proximal femur treated according to the invention and the control (intact) femur. The mean peak load observed across the ten pairs of matched cadaver femurs tested is shown in graph provided in FIG. 22. As seen therein, all proximal femurs fractured at a peak load of about 8,000 N. Thus, the tests indicated there was no clinical risk related to decreased strength in a proximal femur having undergone a procedure according to the invention wherein a void was formed and filled with a bone regenerative material. Specifically, this indicated that there was no increased risk of fracture associated with the inventive methods immediately after carrying out the procedure, even in the absence of any extraneous support materials, such as pin, inserts, or the like.

Example 3

In Vivo Canine Study Using Bone Regeneration Material in a Large, Critically Sized, Longitudinal Proximal Humerus Model A study was carried out to evaluate the 13 and 26 week in vivo performance of bone regeneration materials in a critically sized canine longitudinal proximal humerus defect model. The biologic response, namely new bone formation, implant degradation, and biocompatibility, were evaluated qualitatively through radiographs and histology slides.

In this study, 16 skeletally mature canine subjects each received bilateral longitudinal cylindrical defects (13 mm OD×50 mm) in their proximal humeri. All subjects received OSTEOSET® calcium sulfate bone graft substitute pellets (Wright Medical Technology, Inc., Arlington Tenn.) in one of the two defects. The contralateral defects were treated with either an injected bolus of flowable PRO-DENSE® graft material or preformed pellets of the PRO-DENSE® material, both of which are commercially available. Half of each experimental group underwent evaluation after 13 weeks and the other half after 26 weeks. An additional 10 humeri from five unoperated dogs were obtained for the purpose of generating comparative data on normal bone taken from the same location. All samples were tested for compressive strength and histomorphology.

A limited cranial approach to the greater tubercle of the left and right humerus was performed on each subject through incision and retraction of the cliedobrachialis muscle. Drilling and reaming were used to create the defect of the size noted above in each test site. The formed defects were then backfilled with one of the test materials, alternating materials between the left and right sides to randomize the defect site to the material used. Pellets were tightly packed into each defect with forceps. The bolus injectable was prepared by combining liquid and powder components in a vacuum bone cement mixing apparatus (Summit Medical; Gloucestershire, UK). After mixing for 30 seconds under a 20-23" Hg vacuum, the material was transferred to a 20 cm$^3$ syringe and the bolus (approximately 6 cm$^3$) was delivered to the defect through an 11-gauge, 6 cm$^3$, ported, jamshidi-type needle using a backfilling technique. The wounds were then closed.

Biomechanical testing was conducted to determine the ultimate compression strength and modulus of the newly formed bone using the mechanical test specimens obtained from test sites in the subjects. Testing was performed on an Instron Model 8874 servo-hydraulic mechanical testing system, equipped with a 1 kN Dynacell Dynamic Load Cell and Bluehill Materials Testing Software (system, load cell, and software: Instron Corp., Canton, Mass.). A compression subpress (Wyoming Test Fixtures, Inc., Laramie, Wyo., serial no. WTF-SP-9), ASTM D695 conformant, was modified such that the spherical cap was removed, and the loading rod was machined to screw into the actuator of the test frame. Testing also was carried out to evaluate the amount of new bone material formed in each test specimen. Immediately prior to testing, the specimen length and the diameter of each specimen at half the specimen length were determined (+/−0.01 mm).

Specimens were subjected to unconfined, uniaxial compression tests at a rate of 0.5 mm/min until obvious specimen failure was observed, a significant drop in the load curve, or 30% strain of the specimen was achieved. Specimen ultimate compressive strength and modulus were calculated from the resulting stress-strain curves by the software. Nine mechanical specimens from five additional dogs were cored and tested in the same manner for use as comparative "normal bone" specimens.

Stress vs. strain diagrams were produced for each specimen using the Bluehill Materials Testing Software, and the ultimate compressive strengths were determined as the stress at which the stress-strain diagram resulted in a slope of zero. Ultimate compressive strength (MPa) and modulus of elasticity, E (MPa) for the specimens are shown below in Table 1. Specimens where the OSTEOSET® material was used in two separate tests, and the average values obtained in each test (I and II) are included. Values for normal bone are included as a comparative. Table 2 similarly shows new bone and residual material area fraction at 13 and 26 weeks. These average values were determined through the standard point counting technique.

TABLE 1

| Test Group | Ultimate Compressive Strength (MPa) (SD) [n] | Modulus of Elasticity, E (MPa) (SD) [n] |
| --- | --- | --- |
| Normal Canine Bone | 1.38 (0.66) [8] | 117.04 (71.51) [8] |
| PRO-DENSE ® Flowable (13 wks) | 5.29 (2.61) [5] | 283 (217) [5] |
| PRO-DENSE ® Flowable (26 wks) | 2.19 (0.41) [5] | 150 (73.5) [5] |
| PRO-DENSE ® Pellets (13 wks) | 1.49 (0.85) [3] | 67.2 (50.5) [3] |
| PRO-DENSE ® Pellets (26 wks) | 1.73 (0.96) [3] | 118.4 (107.7) [3] |
| OSTEOSET ® Pellets I (13 wks) | 0.90 (0.44) [5] | 40.8 (35.6) [5] |

TABLE 1-continued

| Test Group | Ultimate Compressive Strength (MPa) (SD) [n] | Modulus of Elasticity, E (MPa) (SD) [n] |
| --- | --- | --- |
| OSTEOSET ® Pellets I (26 wks) | 0.47 (0.46) [4] | 15.8 (23.6) [5] |
| OSTEOSET ® Pellets II (13 wks) | 1.49 (na) [1] | 24.1 (30.9) [3] |
| OSTEOSET ® Pellets II (26 wks) | 0.73 (0.42) [3] | 44.1 (59.9) [3] |

TABLE 2

| Test Group | Area Fraction of New Bone (SD) [n] | Area Fraction of Residual Material (SD) [n] |
| --- | --- | --- |
| Normal Canine Bone | 0.145 (0.024) [5] | NA |
| PRO-DENSE ® Flowable (13 wks) | 0.394 (0.047) [5] | 0.065 (0.033) [5] |
| PRO-DENSE ® Flowable (26 wks) | 0.180 (0.034) [5] | 0.015 (0.020) [5] |
| PRO-DENSE ® Pellets (13 wks) | 0.200 (0.052) [3] | 0.025 (0.011) [3] |
| PRO-DENSE ® Pellets (26 wks) | 0.178 (0.049) [3] | 0.009 (0.000) [3] |
| OSTEOSET ® Pellets I (13 wks) | 0.186 (0.066) [3] | 0.008 (0.007) [3] |
| OSTEOSET ® Pellets I (26 wks) | 0.158 (0.055) [3] | 0.002 (0.003) [3] |
| OSTEOSET ® Pellets II (13 wks) | 0.173 (0.043) [5] | 0.000 (0.000) [5] |
| OSTEOSET ® Pellets II (26 wks) | 0.112 (0.026) [5] | 0.000 (0.000) [5] |

As seen from the above data, the flowable PRO-DENSE® material evidenced an effect on bone formation and mineralization at 13 weeks exceeding that seen for normal bone (5.29 MPa vs. 1.38 MPa). This phenomenon decreased by the 26 weeks point where the average values for compressive strength and modulus of elasticity more closely matched that of normal bone. This phenomenon of remodeling back to normal bone density is consistent with the bone density values in Table 2, wherein bone area fraction in the 13 weeks tests for the flowable PRO-DENSE® material was significantly higher than normal bone density, but the values in relation to the flowable PRO-DENSE® material were much closer to normal bone density at 26 weeks. These findings were consistent with high levels of radiodensity seen in the 13 weeks radiographs of the specimens treated using the flowable PRO-DENSE® material. The specimens treated with the pelletized PRO-DENSE® material did not demonstrate the same degree of bone formation seen in the defects treated with the flowable material. It is important to note, however, that the pelletized material still resulted in formation of bone with properties substantially similar to and even greater than the properties seen with the normal bone specimens at both the 13 week and 26 weeks time points.

The average values of the mechanical properties for the OSTEOSET® pellet treated defects were lower than those of normal bone; however, the differences were not determined to be statistically significant. It also should be noted that the relatively large standard deviations, as provided above, are very common with this type of mechanical testing.

Example 4

Generation of New, Dense Bone Material in a Created Void that is Filled with Bone Regeneration Material To evaluate formation of new bone growth in an osteoporotic patient, the left femur of an 80 year old human female was treated according to the present invention.

Figure 23:
FIG. 23 provides a radiograph of a proximal femur prior to injection of a bone regenerative material in a method according to one embodiment of the invention.
Figure 24:
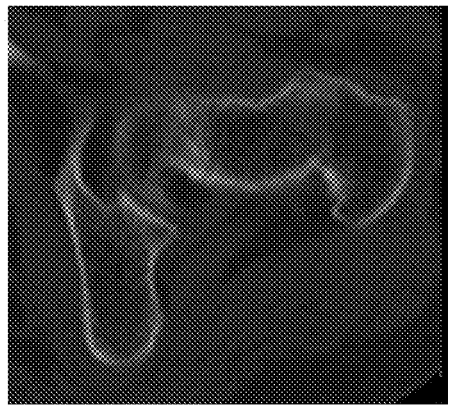
FIG. 24 provides a CT image of the same area of the proximal femur shown in FIG. 23 prior to injection of the bone regenerative material.
Figure 25:
FIG. 25 provides a radiograph of the proximal femur from FIG. 23 intra-operative during injection of a bone regenerative material according to the invention.

Specifically, a void was formed in the proximal femur and filled with PRO-DENSE® graft material. FIG. 23 provides a radiograph of the proximal femur prior to injection of the graft, and FIG. 24 provides a CT image of the same area of the proximal femur prior to injection. FIG. 25 provides a radiograph of the proximal femur intra-operative showing the graft material in place in the proximal femur.

The table below provides T-score and Z-score values for the left femur prior to undergoing the procedure. The table further provides the same values for the right femur (untreated) to be used as a comparative.

TABLE 3

(Time Zero)

| | Left Femur (pre-treatment) | | Right Femur (control) | |
|---|---|---|---|---|
| Region | T-Score | Z-Score | T-Score | Z-Score |
| Neck | −2.7 | −0.4 | −2.8 | −0.5 |
| Trochanter | −2.7 | −0.9 | −2.9 | −1.1 |
| Intertrochanter | −3.4 | −1.5 | −3.5 | −1.7 |
| Total Hip | −3.3 | −1.3 | −3.5 | −1.4 |
| Ward's Area | −3.1 | −0.1 | −2.7 | 0.3 |

Post surgery, the patient was evaluated at multiple intervals to determine changes in density in the localized area of the bone treated according to the invention and changes with time in the control. Table 4 below shows test values at one week post treatment. As seen therein, the treated femur already exhibits dramatic improvements in density while the control femur exhibits osteoporotic values similar to the pre-treatment values.

TABLE 4

(One Week Post Treatment DEXA Scores)

| | Left Femur | | Right Femur (control) | |
|---|---|---|---|---|
| Region | T-Score | Z-Score | T-Score | Z-Score |
| Neck | −1.1 | 1.2 | −3.0 | −0.6 |
| Trochanter | 0.1 | 1.9 | −2.9 | −1.1 |
| Intertrochanter | −0.8 | 0.7 | −3.6 | −1.7 |
| Total Hip | −0.8 | 1.3 | −3.6 | −1.5 |
| Ward's Area | 7.0 | 10 | −3.0 | 0.0 |

Figure 26:
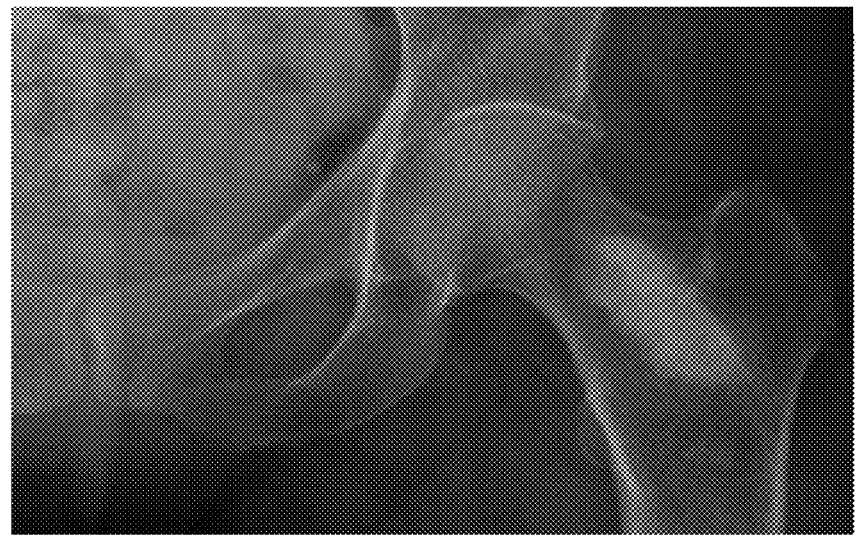
FIG. 26 provides a radiograph of the left femur from FIG. 23 at 6 weeks post treatment in a method according to one embodiment of the invention.

FIG. 26 provides a radiograph of the treated, left femur at 6 weeks post treatment. As seen therein, the graft is beginning to be resorbed by the body as the bone in the localized area remodels. Table 5 provides the test values from the DEXA scans at 6 weeks post treatment.

TABLE 5

(Six Week Post Treatment DEXA Scores)

| | Left Femur | | Right Femur (control) | |
|---|---|---|---|---|
| Region | T-Score | Z-Score | T-Score | Z-Score |
| Neck | 0.2 | 2.5 | −2.8 | −0.4 |
| Trochanter | −0.3 | 1.5 | −2.8 | −1.0 |
| Intertrochanter | −1.5 | 0.3 | −3.5 | −1.7 |
| Total Hip | −1.1 | 1 | −3.5 | −1.4 |
| Ward's Area | 5.9 | 8.9 | −2.8 | 0.2 |

Figure 27:
FIG. 27 provides a CT image of the left femur from FIG. 23 at 12 weeks post treatment in a method according to one embodiment of the invention.

FIG. 27 provides a CT image of the treated, left femur at 12 weeks post treatment. The presence of the graft material (light colored mass) is evident and shows further resorption. Table 6 provides the DEXA scan values at 12 weeks post treatment, and Table 7 provides the DEXA scan values at 18 weeks post treatment.

TABLE 6

(12 Week Post Treatment DEXA Scores)

| | Left Femur | | Right Femur (control) | |
|---|---|---|---|---|
| Region | T-Score | Z-Score | T-Score | Z-Score |
| Neck | −0.2 | 2.2 | −3.2 | −0.9 |
| Trochanter | −0.4 | 1.4 | −3.1 | −1.3 |
| Intertrochanter | −2.0 | −0.2 | −3.8 | −2.0 |
| Total Hip | −1.6 | 0.5 | −3.8 | −1.7 |
| Ward's Area | 4.3 | 7.3 | −3.2 | −0.2 |

TABLE 7

(18 Week Post Treatment DEXA Scores)

| | Left Femur | | Right Femur (control) | |
|---|---|---|---|---|
| Region | T-Score | Z-Score | T-Score | Z-Score |
| Neck | −0.7 | 1.6 | −2.8 | −0.4 |
| Trochanter | 0.9 | 0.9 | −3.0 | −1.2 |
| Intertrochanter | −2.0. | −0.2 | −3.7 | −1.9 |
| Total Hip | −1.7 | 0.4 | −3.7 | −1.6 |
| Ward's Area | 2.9 | 5.9 | −2.9 | 0.1 |

Figure 28:
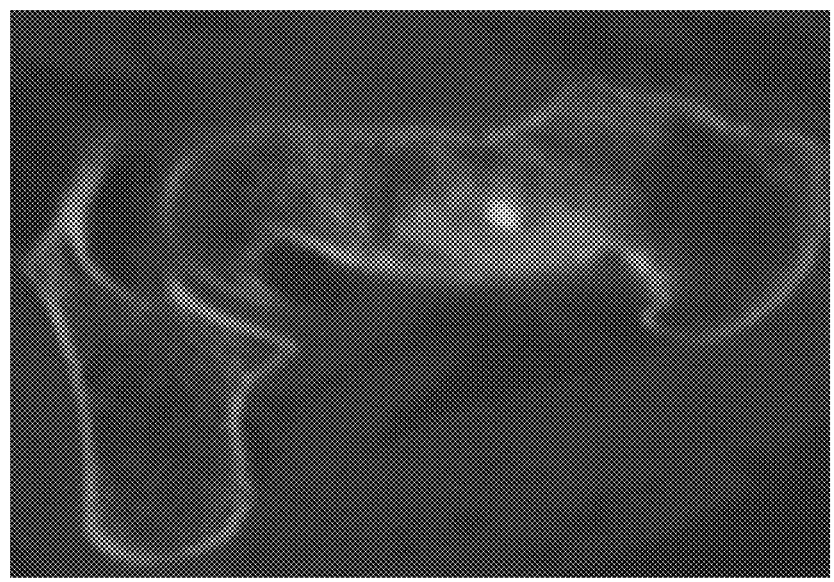
FIG. 28 provides a CT image of the treated, left femur from FIG. 23 at 24 weeks post treatment.

FIG. 28 provides a CT image of the treated, left femur at 24 weeks post treatment. The presence of the graft material (light colored mass) is significantly reduced as the graft material continues to be resorbed and replaced by dense bone material. Table 8 provides the DEXA scan values at 24 weeks post treatment, and Table 9 provides the DEXA scan values at 12 months post treatment.

TABLE 8

(24 Week Post Treatment DEXA Scores)

| | Left Femur | | Right Femur (control) | |
|---|---|---|---|---|
| Region | T-Score | Z-Score | T-Score | Z-Score |
| Neck | −0.9 | 1.5 | −2.9 | −0.6 |
| Trochanter | −0.7 | 1.1 | −3.1 | −1.3 |
| Intertrochanter | −2.2 | −0.3 | −3.8 | −2.0 |
| Total Hip | −1.8 | 0.3 | −3.8 | −1.7 |
| Ward's Area | 1.8 | 4.8 | −3.2 | −0.2 |

TABLE 9

(12 Month Post Treatment DEXA Scores)

| Region | Left Femur T-Score | Right Femur (control) T-Score |
|---|---|---|
| Neck | −1.0 | −3.0 |
| Trochanter | −1.2 | −3.1 |
| Intertrochanter | −2.7 | −4.0 |
| Ward's Area | 1.3 | −3.2 |

Example 5

Increases in BMD in Localized Areas of
Osteoporotic Bone Following Void Formation and
Filling with Bone Regenerative Material Testing was carried out on 12 human patients, all of whom were deemed to be osteoporotic according to the World Health Organization (WHO) definition. In each patient, one femur was treated according to the present invention, and the contralateral side remained untreated for the purpose of comparison.

First, to obtain a baseline, BMD was measured in both hips via DEXA. Thereafter, in the test site in the single hip of each patient, a void was formed in the proximal femur by removing a section of the osteoporotic bone, and the void was filled with PRO-DENSE® graft material similar to the manner illustrated in Example 4. The patients carried out normal daily activities with follow-up scans taken at 1, 6, 12, 18, 24, 52, 78, and 104 weeks. Note that all 12 patients were evaluated up to 24 weeks, eight patients were tested up to 52 weeks, three patients were tested up to 78 weeks, and two patients were tested for the full 104 weeks.

Figure 29:
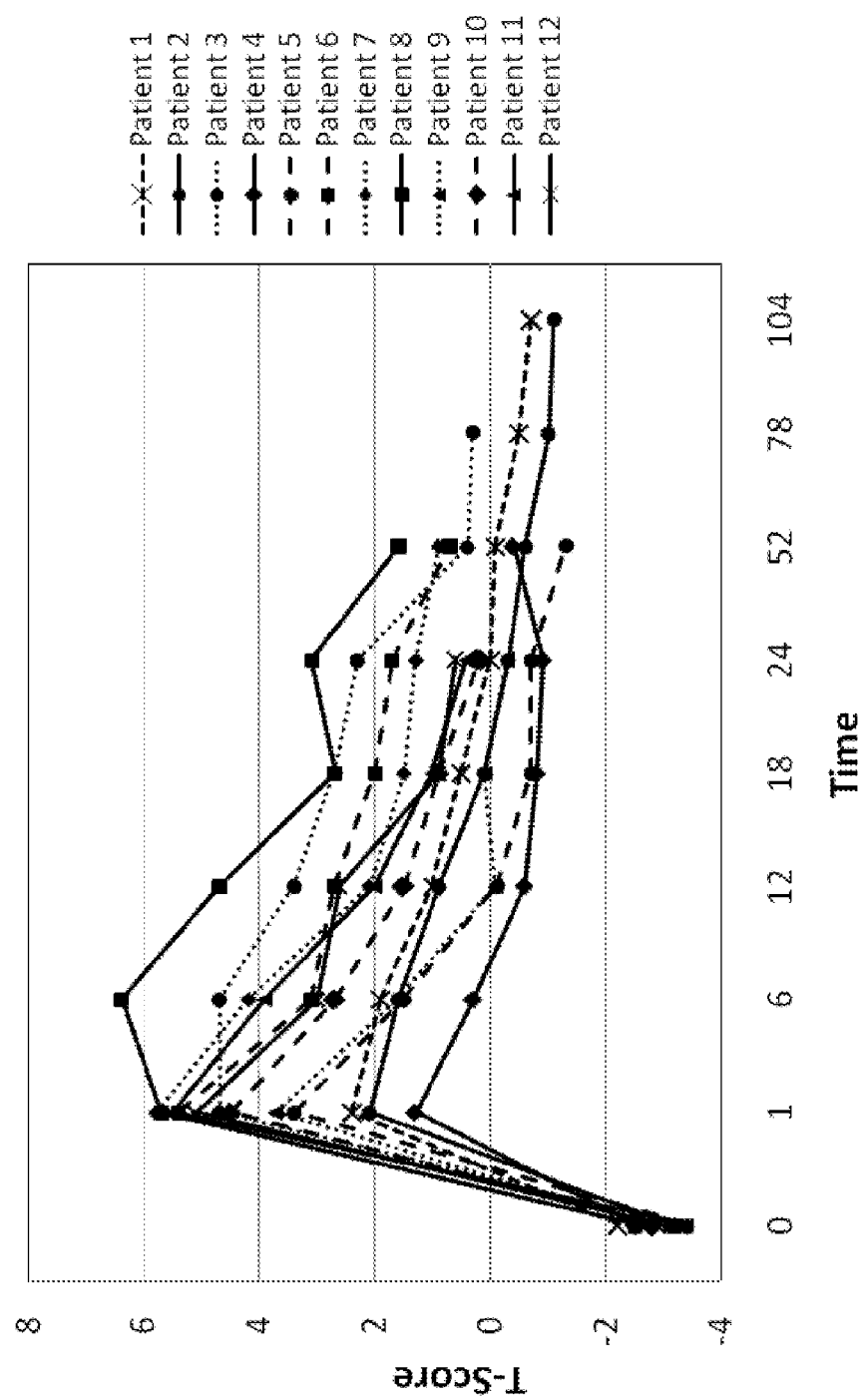
FIG. 29 is a graph providing data over the course of up to two years showing average T-scores at the femoral neck in the treated hip of patients that were treated according to certain embodiments of the invention.
Figure 30:
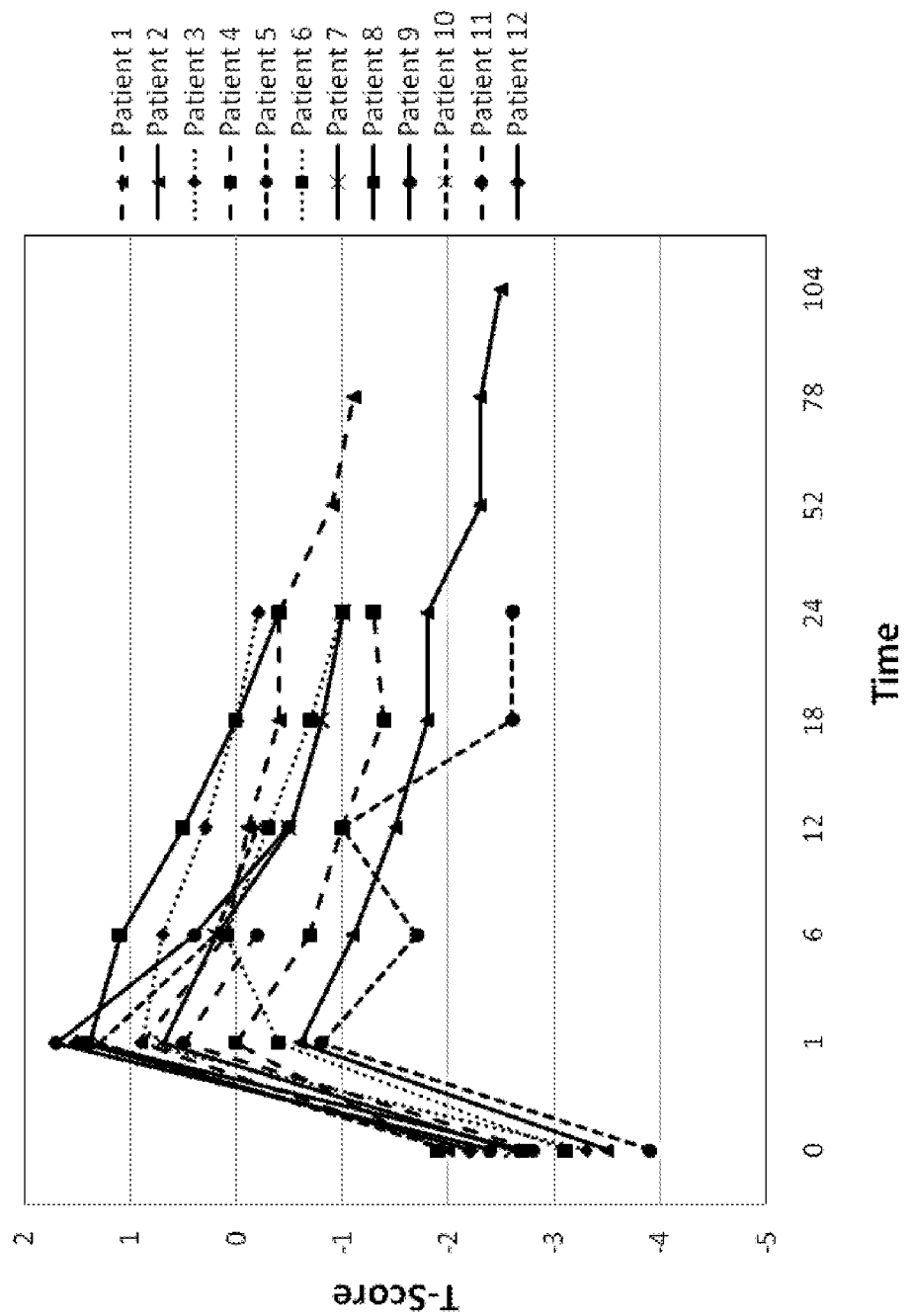
FIG. 30 is a graph providing data over the course of up to two years showing average T-scores of the total hip in the treated hip of patients that were treated according to certain embodiments of the invention.
Figure 31:
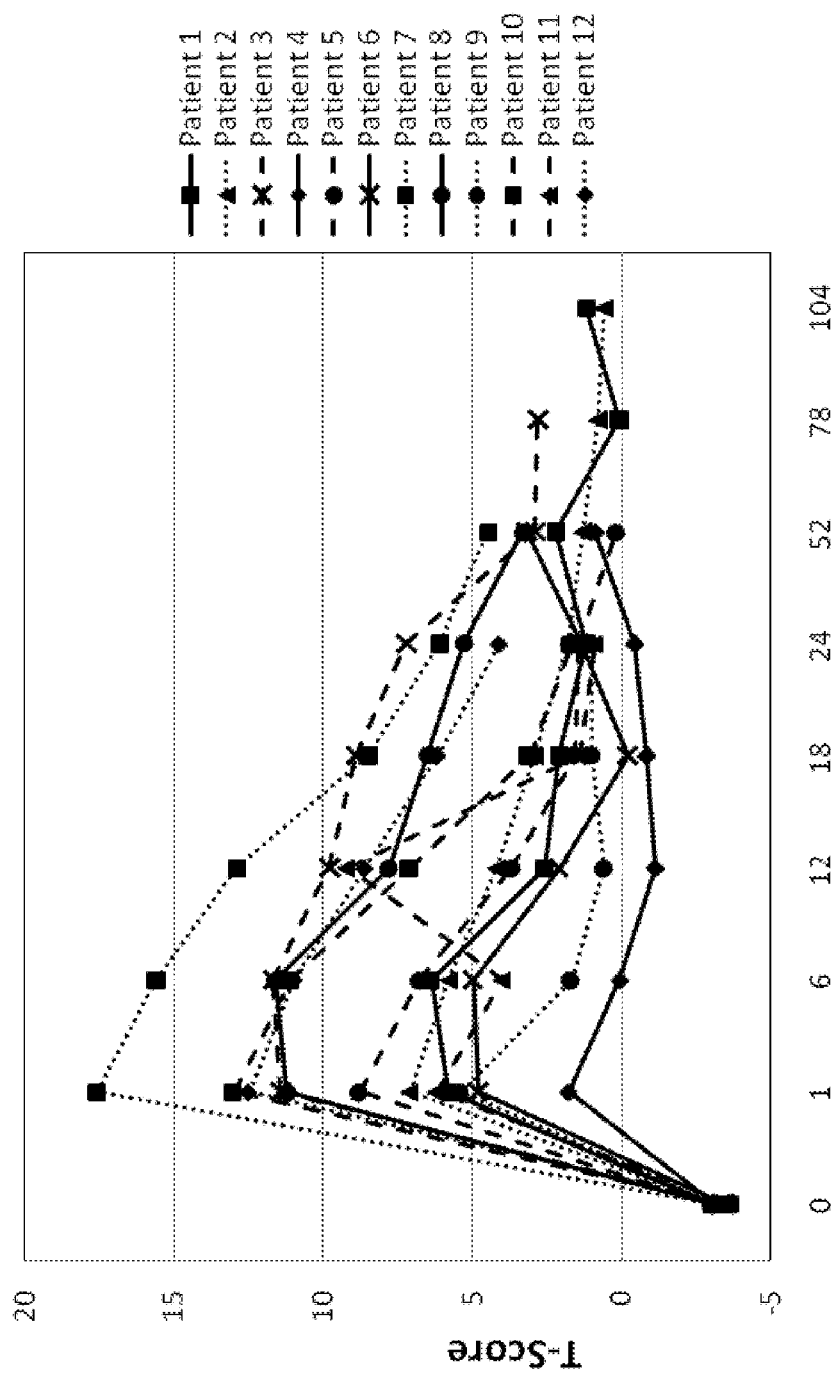
FIG. 31 is a graph providing data over the course of up to two years showing average T-scores of the Ward's triangle area in the treated hip of patients that were treated according to certain embodiments of the invention.

In each follow-up examination (as well as in the baseline measurement), DEXA scan T-scores for each patient were recorded for the femoral neck and for the total hip. As can be seen in reference to FIG. 29, T-Scores at the femoral neck for all patients were less than −2 at baseline; however, each patient exhibited a significant increase in T-score at the one-week mark (ranging from about 1 to almost 6). After this initial rapid increase, T-scores for each patient gradually returned to a normal range for healthy bone (using the average 30 year old as a reference). Within as little as 12 weeks, a few patients had T-scores drop to near or slightly below zero. Even for patients tested out to 104 weeks, T-scores continued to be near normal (although below zero). Similar trends were seen in relation to T-scores in the total hip, as shown in FIG. 30. Although the rapid increase in T-score was not as great as in the femoral neck, initial increases were roughly proportional (i.e., each patient exhibiting an increase of about three points or greater one week after undergoing the procedure). Again, T-scores in the total hip decreased with progression of the test period; however, the final score taken for each patient shows a remodeling to a condition that is significantly improved from the baseline score. Even greater improvements were seen in the Ward's area of the treated hips. As seen in FIG. 31, within one week, T-scores for most patients rose to the range of 5 to as much as 17. Again, the practice of the invention in this area of the hip of the treated patients again resulted in remodeling of the bone to be of a normal quality (i.e., T-score of great than zero in this patients).

Figure 32:
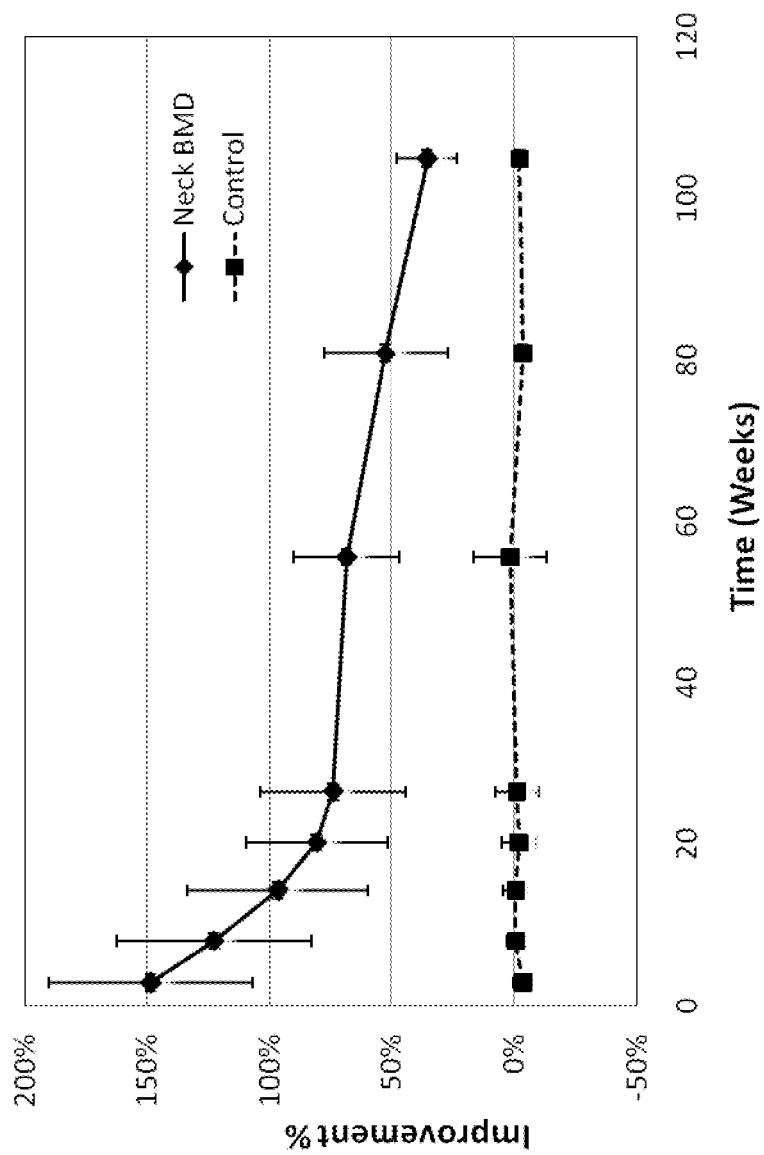
FIG. 32 is a graph providing data over the course of up to two years showing the average percent improvement in bone mineral density (BMD) of the femoral neck in the treated hip of patients that were treated according to certain embodiments of the present invention in reference to the BMD of the femoral neck of the untreated, contralateral hip in the same patients.

The effective, significant increase in bone quality at the treated site after undergoing a replacement procedure according to the invention is further illustrated in FIG. 32, which shows average improvement in BMD at the femoral neck across the patient population at the various intervals. In addition to the T-scores (which illustrate the absolute change in bone quality from osteoporotic bone to normal bone), the comparative mean changes shown in FIG. 32 confirm that the inventive procedures can remodel the basic bone structure of the treated area by removing bone of low BMD and facilitating growth of new bone that has a significantly greater BMD. As seen in FIG. 32, within one week after undergoing the inventive procedure, BMD relative to the control (which is the average BMD from the contralateral, untreated hip in each patient) had increased by approximately 150%. Thereafter, up to about 24 weeks, the relative increase in BMD at the femoral neck shows a relatively rapid remodeling toward the BMD of normal bone (BMD 120% greater than control at 6 weeks, 96% greater than control at 12 weeks, and 74% greater than control at 24 weeks). From this point forward, the BMD began to slowly decrease in a more normalized manner. At the two-year evaluation, the two patients remaining in the study still exhibited a mean BMD increase in the femoral neck of 35% relative to the control.

Figure 33:
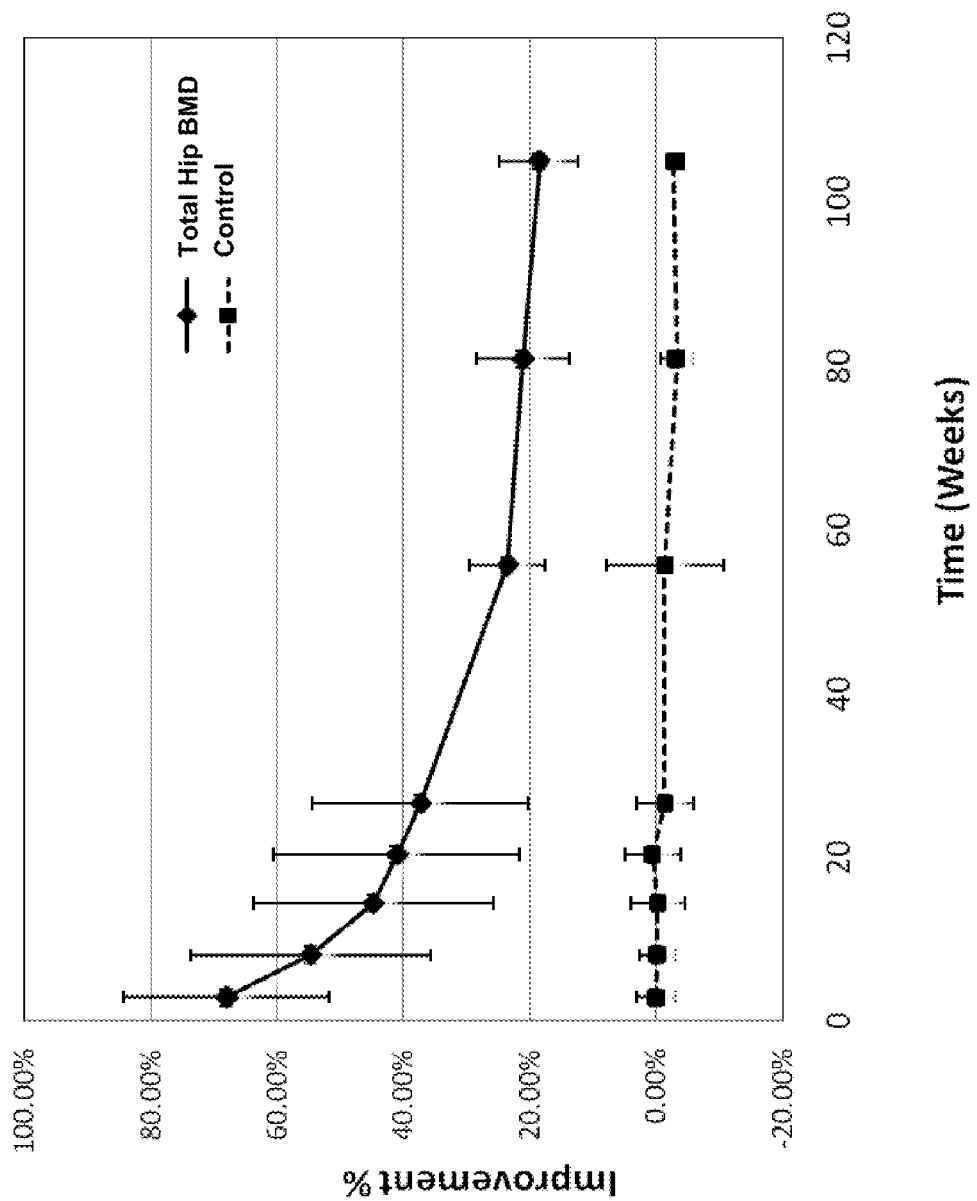
FIG. 33 is a graph providing data over the course of up to two years showing the average percent improvement in bone mineral density (BMD) of the total hip in the treated hip of patients that were treated according to certain embodiments of the present invention in reference to the BMD of the total hip of the untreated, contralateral hip in the same patients.

Similar results are seen in FIG. 33, which shows average improvement in BMD in the total across the patient population at the various intervals. As seen therein, within one week after undergoing the inventive procedure, BMD relative to the control (which is the average BMD from the contralateral, untreated hip in each patient) had increased by approximately 68%. Thereafter, up to about 24 weeks, the relative increase in BMD across the total hip shows a relatively rapid remodeling toward the BMD of normal bone (BMD 54% greater than control at 6 weeks, 45% greater than control at 12 weeks, and 36% greater than control at 24 weeks). From this point forward, the BMD began to slowly decrease in a more normalized manner. At the two-year evaluation, the two patients remaining in the study still exhibited a mean BMD increase across the total hip of 18% relative to the control. Because of this increase in BMD throughout the testing period, it would be expected that the treated area of the bone would exhibit increased compressive strength (as evidenced in the canine study described above) and would have an increased resistance to fracture because of the increased BMD and increased compressive strength. There were no appreciable changes in BMD measurements from baseline in the untreated sides (although FIG. 33 suggests a gradual decrease in BMD across the total hip in the untreated sides from 20 weeks forward).

Figure 34:
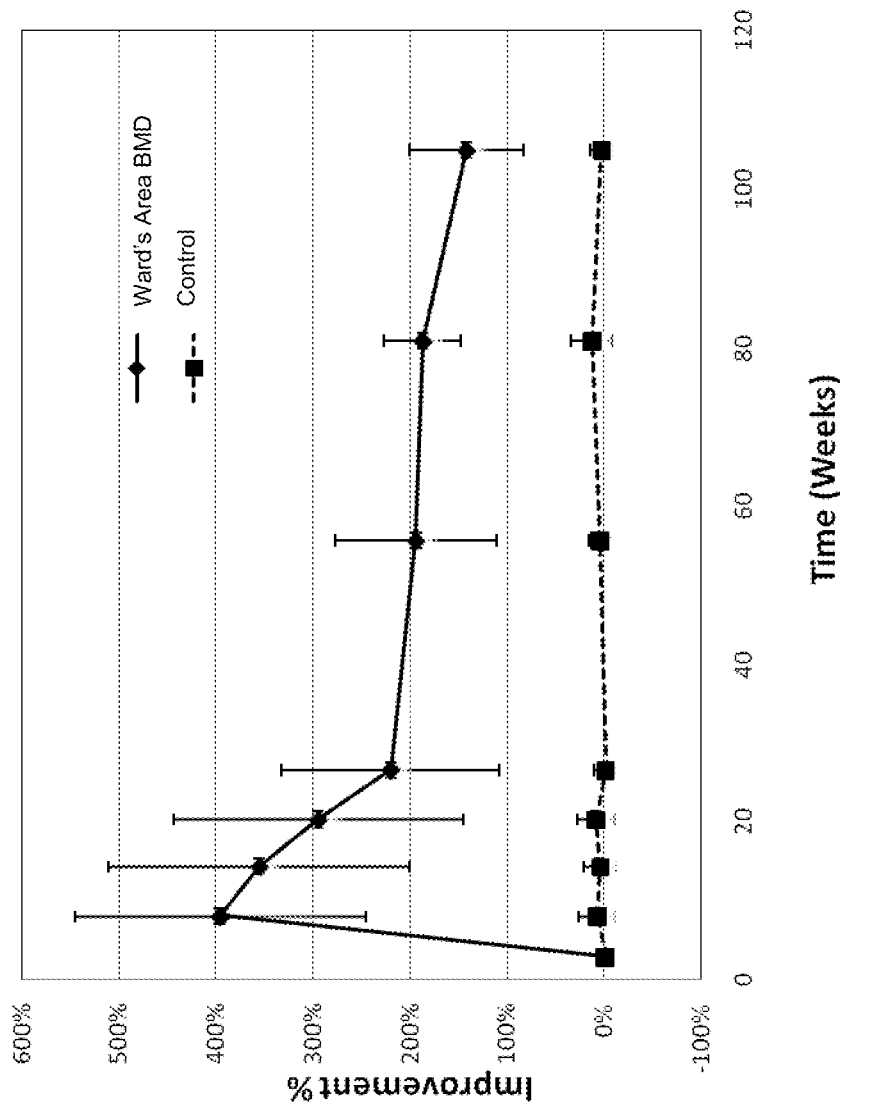
FIG. 34 is a graph providing data over the course of up to two years showing the average percent improvement in bone mineral density (BMD) of the Ward's triangle area in the treated hip of patients that were treated according to certain embodiments of the present invention in reference to the BMD of the total hip of the untreated, contralateral hip in the same patients.

Again, even greater results were seen in relation to BMD increases in the Ward's area, as illustrated in FIG. 34. Within one week after treatment according to the invention, average BMD had risen by 400%. A gradual reduction is seen over time—355% greater BMD at 6 weeks, 295% greater BMD ad 12 weeks, and 220% greater BMD at 24 weeks. From the period cover 52 weeks after treatment to 104 weeks after treatment, BMD for the treated hips in the Ward's area ranged from about 140% to about 200% greater than in the control hip.

Many modifications and other embodiments of the invention will come to mind to one skilled in the art to which this invention pertains having the benefit of the teachings presented in the foregoing descriptions and associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method of treating a human patient suffering from a degenerative bone condition, the degenerative bone condition being either osteoporosis or osteopenia, comprising:
   forming a void in a localized area of a bone of a human patient that has been diagnosed with the degenerative bone condition, the localized area being intact bone prior to the forming step; and
   filling at least a portion of the formed void with a bone regenerative material, which comprises calcium phosphate, calcium sulfate, demineralized bone matrix (DBM), or a combination thereof, wherein the calcium phosphate, calcium sulfate, DBM, or the combination thereof is in an amount effective to facilitate formation of new, non-degenerated bone material into and throughout at least the portion of the void that has been filled with the bone regenerative material, wherein the bone regenerative material does not include a TGF-β isoform in an amount sufficient to facilitate formation of new, non-degenerated bone material into and throughout the portion of the void, wherein the bone regenerative material is flowable when it is filled into the formed void, and wherein the bone for void formation is selected from a group consisting of hip, femur, radius, ulna, humerus, tibia, and a vertebra that is located between a first immediately adjacent intact vertebra on one side of the vertebra and a second immediately adjacent intact vertebra on the other side of the vertebra.

2. The method of claim 1, wherein the bone regenerative material further comprises an osteoinductive material, osteoconductive material, osteogenic material, osteopromotive material, anti-osteoporotic material, or osteophilic material.

3. The method of claim 1, wherein the bone regenerative material comprises calcium sulfate.

4. The method of claim 3, wherein the bone regenerative material further comprises calcium phosphate.

5. The method of claim 4, wherein the bone regenerative material further comprises tricalcium phosphate granules.

6. The method of claim 1, wherein the bone regenerative material comprises a material exhibiting a multi-phasic resorption profile in vivo.

7. The method of claim 1, wherein the bone regenerative material comprises a material exhibiting a bi-phasic resorption profile in vivo.

8. The method of claim 1, wherein the bone regenerative material comprises a material exhibiting a tri-phasic resorption profile in vivo.

9. The method of claim 1, wherein the bone regenerative material hardens in vivo.

10. The method of claim 1, wherein the newly formed, non-degenerated bone material has a T-score measured by Dual Energy X-ray Absorptiometry (DEXA) that is greater than 0.

11. The method of claim 1, wherein the new bone material has a T-score measured by Dual Energy X-ray Absorptiometry (DEXA) that is greater than −1.0.

12. The method of claim 1, wherein the new bone material has a T-score measured by Dual Energy X-ray Absorptiometry (DEXA) that is greater than −0.5.

13. The method of claim 1, wherein the bone regenerative material facilitates formation of new bone material in the area of the bone adjacent the formed void, the new bone material in the area of the adjacent bone having a T-score measured by Dual Energy X-ray Absorptiometry (DEXA) that is greater than 0.

14. The method of claim 1, wherein the BMD in the localized area of the bone is increased such that a T-score measured by Dual Energy X-ray Absorptiometry (DEXA) for the newly formed, non-degenerated bone material is greater than the T-score of the bone prior to void formation.

15. The method of claim 14, wherein the T-score of the bone prior to void formation is less than −1.0 and the newly formed, nondegenerated bone material has a T-score of greater than −1.0.

16. The method of claim 14, wherein the T-score of the newly formed, nondegenerated bone material is at least 0.5 units greater than the T-score of the bone prior to void formation.

17. The method of claim 14, wherein the T-score of the bone prior to void formation is less than −1.0 and the newly formed, nondegenerated bone material has a T-score of at least −0.5.

18. The method of claim 14, wherein the T-score of the bone prior to void formation is less than −1.0 and the newly formed, nondegenerated bone material has a T-score of at least 0.

19. The method of claim 14, wherein the increase in BMD in the localized area of the bone is maintained for a time of at least 1 year measured from the time of new bone material formation.

20. The method of claim 1, wherein, after filling the at least portion of the formed void with the bone regenerative material, new bone material is formed within the void over time and at least a portion of the bone regenerative material is resorbed.

21. The method of claim 20, wherein a BMD profile is created in the localized area of a bone such that a T-score, as measured by Dual Energy X-ray Absorptiometry (DEXA), increases from an initial score of less than −1.0, as measured prior to forming the void, to a maximum score of at least 5.0 within a time of about 1 week to about 18 weeks from the time of filling the at least portion of the formed void with the bone regenerative material and decreases over time to a score of about −1.0 to about 2.0.

22. The method of claim 21, wherein the T-score decreases over time to a score of about −0.5 to about 2.0.

23. The method of claim 22, wherein the T-score decreases to a score of about −0.5 to about 2.0 within a time of about 6 weeks to about 12 months after achieving the maximum T-score.

24. The method of claim 21, wherein the BMD profile in the localized area of the bone is such that T-score remains in the range substantially corresponding to normal bone of about −1.0 to about 2.0 for a time of at least 1 year after the normal range is achieved.

25. The method of claim 1, wherein the localized area of the degenerative bone is remodeled, to be substantially identical to normal bone in that whereby the bone material in the localized area before forming the void has a T-score, as measured by Dual Energy Xray Absorptiometry (DEXA), of less than −1.0 indicating bone degeneration, and new bone material present after remodeling has a T-score of greater than −1.0 indicating the bone in the localized area has been remodeled to be substantially identical to normal bone.

26. The method of claim 25, wherein the new bone material present after remodeling has a T-score of at least −0.5.

27. The method of claim 25, wherein the new bone material present after remodeling has a T-score of at least 0.

28. The method of claim 25, wherein the new bone material present after remodeling has a T-score of about −0.5 to about 2.

29. The method of claim 1, wherein the method restores vertebral body height or corrects angular deformity in a fractured vertebra that is osteopenic or osteoporotic by causing in-growth of new bone material that has a T-score, as measured by Dual Energy X-ray Absorptiometry (DEXA), of greater than −1.0.

30. The method of claim 29, wherein the T-score of the new bone material is at least −0.5.

31. The method of claim 1, wherein the method steps are carried out using instruments from a kit comprising a drill arranged for forming a channel of a defined diameter through a portion of the bone, a debridement probe, and an amount of the bone regenerative material suitable for filling the at least portion of the formed void in the localized area of the bone.

32. The method of claim 31, wherein the method steps are carried out according to an instruction set included with the kit that instructs how to use the kit components to treat the patient suffering from the degenerative bone condition.

33. The method of claim 1, wherein the bone regenerative material further includes a biologically active agent.

34. The method of claim 1, wherein the bone regenerative material comprises a mixture of a calcium sulfate dehydrate phase characterized by a first in vivo resorption rate, a brushite phase characterized by a second in vivo resorption rate slower than the first in vivo resorption rate, and a β-tricalcium phosphate granule phase characterized by a third in vivo resorption rate slower than the second in vivo resorption rate.

35. The method of claim 1, wherein the bone regenerative material is formed from a particulate composition comprising:
   i) an a-calcium sulfate hemihydrate powder at a concentration of at least about 50 weight percent based on the total weight of the particulate composition; and
   ii) a combination of two calcium phosphate powders capable of reacting to form brushite in the presence of an aqueous solution.

36. The method of claim 35, wherein the a-calcium sulfate hemihydrate is present in the particulate composition at a concentration of at least about 70 weight percent based on the total weight of the particulate composition.

37. The method of claim 35, wherein the particulate composition further comprises β-tricalcium phosphate granules.

38. The method of claim 37, wherein the β-tricalcium phosphate granules are present in the particulate composition at a concentration of about 8 to about 12 weight percent based on the total weight of the particulate composition.

39. The method of claim 1, wherein the bone for void formation is selected from a group consisting of a hip bone, innominate bone, coxal bone, and a portion of the femur including a head, neck, greater trochanter, lesser trochanter or Ward's area of a femur.

40. The method of claim 1, wherein the bone regenerative material consists essentially of calcium sulfate, calcium phosphate, and tricalcium phosphate granules and exhibits a tri-phasic profile in vivo.

41. The method of claim 1, wherein the step of forming a void comprises drilling or channeling into the interior of the localized area of the bone.

42. The method of claim 1, wherein the step of forming a void comprises breaking apart the bone materials at the localized area of the bone.

43. The method of claim 1, wherein step of forming a void comprises removing at least a portion of the bone material at the localized area of the bone.

* * * * *